US009487536B2

(12) United States Patent
Bommagani et al.

(10) Patent No.: US 9,487,536 B2
(45) Date of Patent: Nov. 8, 2016

(54) MELAMPOMAGNOLIDE B DERIVATIVES

(71) Applicants: Board of Trustees of the University of Arkansas, Little Rock, AR (US); The Regents of the University of Colorado, Aurora, CO (US)

(72) Inventors: Shobanbabu Bommagani, Little Rock, AR (US); Peter Crooks, Little Rock, AR (US); Narsimha Reddy Penthala, Little Rock, AR (US); Venumadhav Janganati, Little Rock, AR (US); Craig T. Jordan, Aurora, CO (US); Jessica Ponder, Aurora, CO (US)

(73) Assignees: BOARD OF TRUSTEES OF THE UNIVERSITY OF ARKANSAS, Little Rock, AR (US); REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

(21) Appl. No.: 14/676,537

(22) Filed: Apr. 1, 2015

(65) Prior Publication Data

US 2015/0203508 A1 Jul. 23, 2015

Related U.S. Application Data

(63) Continuation-in-part of application No. 14/537,389, filed on Nov. 10, 2014.

(60) Provisional application No. 61/901,714, filed on Nov. 8, 2013.

(51) Int. Cl.
*C07D 493/04* (2006.01)
(52) U.S. Cl.
CPC .................. *C07D 493/04* (2013.01)
(58) Field of Classification Search
IPC .................................................. C07D 493/04
See application file for complete search history.

(56) References Cited

U.S. PATENT DOCUMENTS

| 7,312,242 | B2 | 12/2007 | Crooks et al. | |
| 7,678,904 | B2 | 3/2010 | Crooks et al. | |
| 8,884,027 | B2* | 11/2014 | Crooks | C07D 493/04 544/153 |
| 2012/0122943 | A1* | 5/2012 | Crooks | C07D 519/00 514/387 |
| 2015/0133444 | A1 | 5/2015 | Janganati et al. | |
| 2015/0203508 | A1 | 7/2015 | Bommagani et al. | |
| 2016/0083397 | A1 | 3/2016 | Penthala et al. | |

FOREIGN PATENT DOCUMENTS

| WO | 2008/022104 A1 | 2/2008 |
| WO | 2008022104 A1 | 2/2008 |
| WO | 2012145678 A1 | 10/2012 |
| WO | 2014/172608 A2 | 10/2014 |
| WO | 2014172607 A1 | 10/2014 |

OTHER PUBLICATIONS

Acton et al., "Anticancer Specificity of Some Ellipticinium Salts against Human Brain Tumors in Vitro," Journal of Medicinal Chemistry, 1994, pp. 2185-2189, vol. 37, No. 14.
Bork et al., "Sesquiterpene lactone containing Mexican Indian medicinal plants and pure sesquiterpene lactones as potent inhibitors of transcription factor NF-kB," FEBS Letters, 1997, pp. 85-90, vol. 402.
Boyd et al., "Some Practical Considerations and Applications of the National Cancer Institute In Vitro Anticancer Drug Discovery Screen," Drug Development Research, 1995, pp. 91-109, vol. 34.
Dai et al., "The NF (Nuclear factor)-kB inhibitor parthenolide interacts with histone deacetylase inhibitors to induce MKK7/JNK1-dependent apoptosis in human acute myeloid leukaemia cells," British Journal of Haematology, 2010, pp. 70-83, vol. 151.
de Groot et al., "Synthesis and Biological Evaluation of 2' -Carbamate-Linked and 2'-Carbonate-Linked Prodrugs of Paclitaxel: Selective Activation by the Tumor-Associated Protease Plasmin," J. Med. Chem., 2000, pp. 3093-3102, vol. 43, No. 16.
Dell'Agli et al., "Inhibition of NF-kB and metalloproteinase-9 expression and secretion by pathenolide derivatives," Bioorganic & Medicinal Chemistry Letters, 2009, pp. 1858-1860, vol. 19.
Deschler et al., "Acute Myeloid Leukemia: Epidemiology and Etiology," Cancer, 2006, pp. 2099-2107, vol. 107, No. 9.
El-Feraly, "Melampolides From Magnolia Grandiflora," Phytochemistry, 1984, pp. 2372-2374, vol. 23, No. 10.
Estey et al., "Acute myeloid leukaemia," Lancet, 2006, pp. 1894-1907, vol. 368.
Ghantous et al., "What made sesquiterpene lactones reach cancer clinical trials?" Drug Discovery Today, 2010, pp. 668-678, vol, 15, Nos. 15/16.
Gopal et al., "Parthenolide Specifically Depletes Histone Deacetylase 1 Protein and Induces Cell Death through Ataxia Telangiectasia Mutated," Chemistry & Biology, 2007, pp. 813-823, vol. 14.
Guzman et al., "The sesquiterpene lactone parthenolide induces apoptosis of human acute myelogenous leukemia stem and progenitor cells," Blood, 2005, pp. 4163-4169, vol. 105, No. 11.
Guzman et al., "Feverfew: weeding out the root of leukaemia," Expert Opin. Biol. Ther., 2005, pp. 1147-1152, vol. 5, No. 9.
Guzman et al., "An orally bioavailable parthenolide analog selectively eradicates acute myelogenous leukemia stem and progenitor cells," Blood, 2007, pp. 4427-4435, vol. 110, No. 13.
Hall et al., "Anti-Inflammatory Activity of Sesquiterpene Lactones and Related Compounds," Journal of Pharmaceutical Sciences, 1979, pp. 537-542, vol. 68, No. 5.
Hassane et al., "Chemical genomic screening reveals synergism between parthenolide and inhibitors of the PI-3 kinase and mTOR pathways," Blood, 2010, pp. 5983-5990, vol. 116, No. 26.
Hehner et al., "Sesquiterpene Lactones Specifically Inhibit Activation of NF-kB by Preventing the Degradation of IkB-α and IkB-β," The Journal of Biological Chemistry, 1998, pp. 1288-1297, vol. 273, No. 3.
Heptinstall et al., "Inhibition of Platelet Behaviour by Feverfew: a Mechanism of Action Involving Sulphydryl Groups," Folia Haematol. Int. Mag. KIM. Morphol. Blutforsch, 1988, pp. 447-449, vol. 115, No. 4.
Hewamana et al., "The NF-kB subunit Rel A is associated with in vitro survival and clinical disease progression in chronic lymphocytic leukemia and represents a promising therapeutic target," Blood, 2008, pp. 4681-4689, vol. 111, No. 9.
International Search Report and Written Opinion from related International Application No. PCT/US2014/34605, dated Nov. 7, 2014; 11 pgs.

(Continued)

*Primary Examiner* — Shirley V Gembeh
(74) *Attorney, Agent, or Firm* — Polsinelli PC

(57) ABSTRACT

The present disclosure provides derivatives of melampomagnolide B (MMB), including carbonates, carbamates, thiocarbamates, ester and amide derivatives of MMB. These derivatives are useful for treating cancer in humans.

7 Claims, 23 Drawing Sheets

(56) References Cited

OTHER PUBLICATIONS

Kim et al., "Resistance of cholangiocarcinoma cells to parthenolide-induced apoptosis by the excretory—secretory products of Clonorchis sinensis," Parasitol Res., 2009, pp. 1011-1016, vol. 104.
Kim et al., "Myeloperoxidase Expression as a Potential Determinant of Parthenolide-Induced Apoptosis in Leukemia Bulk and Leukemia Stem Cells," The Journal of Pharmacology and Experimental Therapeutics, 2010, pp. 389-400, vol. 335, No. 2.
Knight, "Feverfew: Chemistry and Biological Activity," Natural Product Reports, 1995, pp. 271-276, vol. 12.
Kolev et al., "Discovery of potent parthenolide-based antileukemic agents enabled by late-stage P450-mediated C—H functionalization," ACS Chem. Biol., 2014, pp. 164-173, vol. 9, No. 1.
Lowenberg et al., "Mitoxantrone Versus Daunorubicin in Induction-Consolidation Chemotherapy—The Value of Low-Dose Cytarabine for Maintenance of Remission, and an Assessment of Prognostic Factors in Acute Myeloid Leukemia in the Elderly: Final Report of the Leukemia Cooperative Group of the European Organization for the Research and Treatment of Cancer and the Dutch-Belgian Hemato-Oncology Cooperative Hovon Group Randomized Phase III Study AML-9," Journal of Clinical Oncology, 1998, pp. 872-881, vol. 16, No. 3.
Macias et al., "Potential Allelopathic Activity of Several Sesquiterpene Lactone Models," Phytochemistry, 1992, pp. 1969-1977, vol. 31, No. 6.
Nasim et al., "Antileukemic activity of aminoparthenolide analogs," Bioorganic & Medicinal Chemistry Letters, 2008, pp. 3870-3873, vol. 18.
Nasim et al., "Melampomagnolide B: a new antileukemic sesquiterpene," Bioorganic & Medicinal Chemistry, 2011, pp. 1515-1519, vol. 19.
Neelakantan et al., "Aminoparthenolides as novel anti-leukemic agents: Discovery of the NF-kB inhibitor, DMAPT (LC-1)," Bioorganic & Medicinal Chemistry Letters, 2009, pp. 4346-4349, vol. 19.
Nozaki et al., "Repression of GADD153/CHOP by NF-kB: a possible cellular defense against endoplasmic reticulum stress-induced cell death," Oncogene, 2001, pp. 2178-2185, vol. 20.
Oka et al., "Sesquiterpene lactone parthenolide suppresses tumor growth in a xenograft model of renal cell carcinoma by inhibiting the activation of NF-kB," Int. J. Cancer, 2007, pp. 2576-2581, vol. 120.
Pei et al., "Targeting Aberrant Glutathione Metabolism to Eradicate Human Acute Myelogenous Leukemia Cells," The Journal of Biological Chemistry, 2013, pp. 33542-33558, vol. 288, No. 47.
Penthala et al., "Heck products of parthenolide and melampomagnolide-B as anticancer modulators that modify cell cycle progression," European Journal of Medicinal Chemistry, 2014, pp. 517-525, vol. 85.
Pfaffenrath et al., "The efficacy and safety of Tanacetum parthenium (feverfew) in migraine prophylaxis—a double-blind, multicentre, randomized placebo-controlled dose-response study," Cephalalgia, 2002, pp. 523-532, vol. 22.
PUBCHEM-CID: 44255396 Create Date: Nov. 16, 2009; 3 pgs.
Ralstin et al., "Parthenolide Cooperates with NS398 to Inhibit Growth of Human Hepatocellular Carcinoma Cells through Effects on Apoptosis and G0-G1 Cell Cycle Arrest," Mol. Cancer Res., 2006, pp. 387-399, vol. 4, No. 6.
Riganti et al., "Artemisinin induces doxorubicin resistance in human colon cancer cells via calcium-dependent activation of HIF-1a and P-glycoprotein overexpression," British Journal of Pharmacology, 2009, pp. 1054-1066, vol. 156.
Saadane et al., "Parthenolide inhibits ERK and AP-1 which are dysregulated and contribute to excessive IL-8 expression and secretion in cystic fibrosis cells," Journal of Inflammation, 2011, pp. 1-15, vol. 8, No. 26.
Sharma et al., "Theoretical and Experimental Studies on a/e-Hybrid Peptides: Design of a 14/12-Helix from Peptides with Alternating (S)-C-Linked Carbo-e-amino Acid [(S)-e-Caa(x)] and L-Ala," Journal of Organic Chemistry, 2009, pp. 6703-6713, vol. 74, No. 17.
Sharma et al., "Synthesis and Structure of a/s-Hybrid Peptides—Access to Novel Helix Patterns in Foldamers," Chem. Eur. J., 2009, pp. 5552-5566, vol. 15.
Skalska et al., "Modulation of Cell Surface Protein Free Thiols: A Potential Novel Mechanism of Action of the Sesquiterpene Lactone Parthenolide," PLoS One, 2009, e8115, 8 pgs., vol. 4, No. 12.
Staab, "Syntheses Using Heterocyclic Amides (Azolides)," Angew. Chem. internat. Edit., 1962, pp. 351-367, vol. 1, No. 7.
Sugimoto et al., "Activation of Dithiocarbamate by 2-Halothiazolium Salts," J. Org. Chem., 1988, pp. 2263-2267, vol. 53, No. 10.
Sweeney et al., "Nuclear Factor-kB Is Constitutively Activated in Prostate Cancer In vitro and is Overexpressed in Prostatic Intraepithelial Neoplasia and Adenocarcinoma of the Prostate," Clinical Cancer Research, 2004, pp. 5501-5507, vol. 10.
Tazzari et al., "Multidrug resistance-associated protein 1 expression is under the control of the phosphoinositide 3 kinase/Akt signal transduction network in human acute myelogenous leukemia blasts," Leukemia, 2007, pp. 427-438, vol. 21.
Wen et al., "Oxidative Stress-mediated Apoptosis: The Anticancer Effect of the Sesquiterpene Lactone Parthenolide," The Journal of Biological Chemistry, 2002, pp. 38954-38964, vol. 277, No. 41.
Won et al., "Parthenolide sensitizes ultraviolet (UV)-B-induced apoptosis via protein kinase C-dependent pathways," Carcinogenesis, 2005, pp. 2149-2156, vol. 26, No. 12.
Woods et al., "Fluorinated Amino-Derivatives of the Sesquiterpene Lactone, Parthenolide, as 19F NMR Probes in Deuterium-Free Environments," Journal of Medicinal Chemistry, 2011, pp. 7934-7941, vol. 54.
Yip-Schneider et al., "Parthenolide and sulindac cooperate to mediate growth suppression and inhibit the nuclear factor-kB pathway in pancreatic carcinoma cells," Molecular Cancer Therapeutics, 2005, pp. 587-594, vol. 4, No. 4.
Office Action from related U.S. Appl. No. 14/537,389, dated Oct. 5, 2015; 10 pgs.
International Search Report related to PCT/US2015/063792, dated Feb. 5, 2016, 10 pages.
Office Action related to U.S. Appl. No. 14/537,389 dated Oct. 5, 2015, 10 pages.
Office Action from related U.S. Appl. No. 14/537,389, dated Mar. 11, 2016, 8 pgs.

* cited by examiner

MELAMPOMAGNOLIDE B DERIVATIVES

CROSS REFERENCE TO RELATED APPLICATIONS

This application is a continuation-in-part of U.S. non-provisional application Ser. No. 14/537,389, filed Nov. 10, 2014, which claims the priority of U.S. provisional application No. 61/901,714, filed Nov. 8, 2013, which are hereby incorporated by reference in their entirety.

GOVERNMENTAL RIGHTS

This invention was made with government support under Grant No. CA158275 awarded by the National Institutes of Health (NIH). The government has certain rights to the invention.

FIELD OF THE INVENTION

This disclosure generally relates to a series of melampomagnolide B (MMB) derivatives, including carbamate, thiocarbamate, carbonate, ester and amide derivatives of MMB. These compounds exhibit potent anticancer activity.

BACKGROUND OF THE INVENTION

Parthenolide (PTL), an abundant sesquiterpene lactone found in the medicinal herb feverfew (*Tanacetum parthenium*), has undergone intense pharmacological research, especially for its antileukemic properties. Initial biomechanistic studies of PTL and its derivatives indicate that the compound promotes apoptosis by inhibiting the NF-kB transcription factor complex, thereby downregulating anti-apoptotic genes under NF-kB control. PTL and its derivatives may also interfere with glutathione function, specifically glutathione's ability to sequester reactive oxygen species. In culture, PTL induces robust apoptosis of primary acute myeloid leukemia (AML) cells. To overcome poor water-solubility, PTL may be derivatized with an alkylamino, which can convert into water-soluble salts. A series of fluorinated amino derivatives of PTL exhibit activity in antiproliferative assays in HL-60 (human promyelocytic leukemia) cells. PTL has also been the source of several antileukemic compounds arising from chemical modification of the PTL molecule.

Melampomagnolide B (MMB), a melampolide originally isolated from *Magnolia grandiflora*, is an antileukemic sesquiterpene with properties similar to those of PTL. MMB has been synthesized via selenium oxide oxidation of the C10 methyl group of PTL, resulting in a concomitant conversion of the geometry of the C9-C10 double bond from trans to the cis geometry. MMB contains a primary OH group, providing a point of attachment for derivatives with increased water solubility, bioavailability, and tissue targeting. Phase 1 clinical data from dimethylaminoparthenolide (DMAPT), a synthetic aminoparthenolide derivative, indicated improved bioavailability and longer in vivo half-lifes for PTL and MMB derivatives with increased water solubility.

SUMMARY OF THE INVENTION

Briefly, therefore, one aspect of the present disclosure encompasses compounds comprising Formula (I):

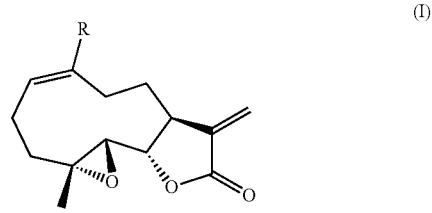

(I)

wherein:

R is selected from the group consisting of

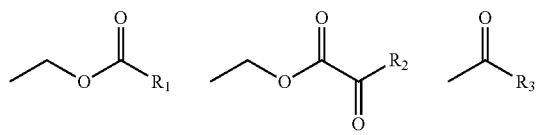

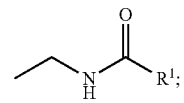

wherein:

$R_1$ is selected from the group consisting of substituted indoles, substituted heterocyclic aromatic, aromatic and aliphatic derivatives;

$R_2$ is selected from the group consisting of substituted indoles; and $R_3$ is selected from the group consisting of substituted amines.

Another aspect of the disclosure provides a process for preparing a compound comprising Formula (I). The process comprises (a) contacting a compound comprising MMB with a compound selected from the group consisting of: (i) a compound comprising a carboxylic acid; and (ii) a compound comprising an acyl chloride; (b) contacting a compound comprising melampomagnolic acid with a compound comprising a heterocyclic amine; or (c) contacting a compound comprising an amine derivative of MMB with a compound comprising a carboxylic acid to form a compound comprising Formula (I):

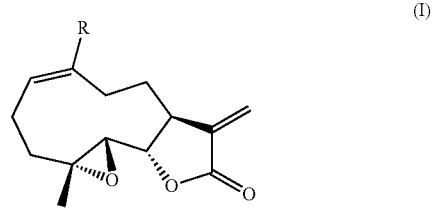

(I)

wherein:
R is selected from the group consisting of

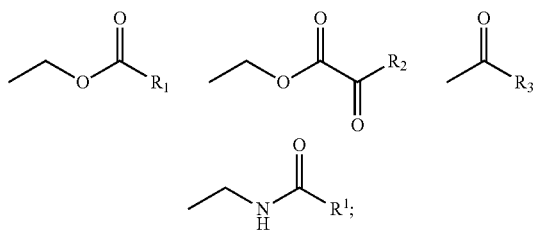

wherein:
R₁ is selected from the group consisting of substituted indoles, substituted heterocyclic aromatic, aromatic and aliphatic derivatives;
R₂ is selected from the group consisting of substituted indoles; and
R₃ is selected from the group consisting of substituted amines.

Yet another aspect of the disclosure provides a method for inhibiting growth of a cancer cell. The method comprises contacting the cancer cell with an amount of a compound comprising Formula (I), or a salt thereof, effective to inhibit growth of the cancer cell.

Other features and iterations of the invention are described in more detail below.

BRIEF DESCRIPTION OF THE FIGURES

The application file contains at least one drawing executed in color. Copies of this patent application publication with color drawing(s) will be provided by the Office upon request and payment of the necessary fee.

(FIG. 17A) Leukeima; (FIG. 17B) Non-Small Cell Lung Cancer; (FIG. 17C) Colon Cancer; (FIG. 17D) CNS Cancer; (FIG. 17E) Melanoma; (FIG. 17F) Ovarian Cancer; (FIG. 17G) Renal Cancer; (FIG. 17H) Prostate Cancer; and (FIG. 17I) Breast Cancer.

FIG. 19A shows leukemia, NSCLC, colon cancer and CNS cancer and FIG. 19B shows melanoma, ovarian cancer, renal cancer, prostate cancer and breast cancer.

FIG. 20A shows leukemia, NSCLC, colon cancer and CNS cancer and FIG. 20B shows melanoma, ovarian cancer, renal cancer, prostate cancer and breast cancer.

DETAILED DESCRIPTION OF THE INVENTION

Figure 1:
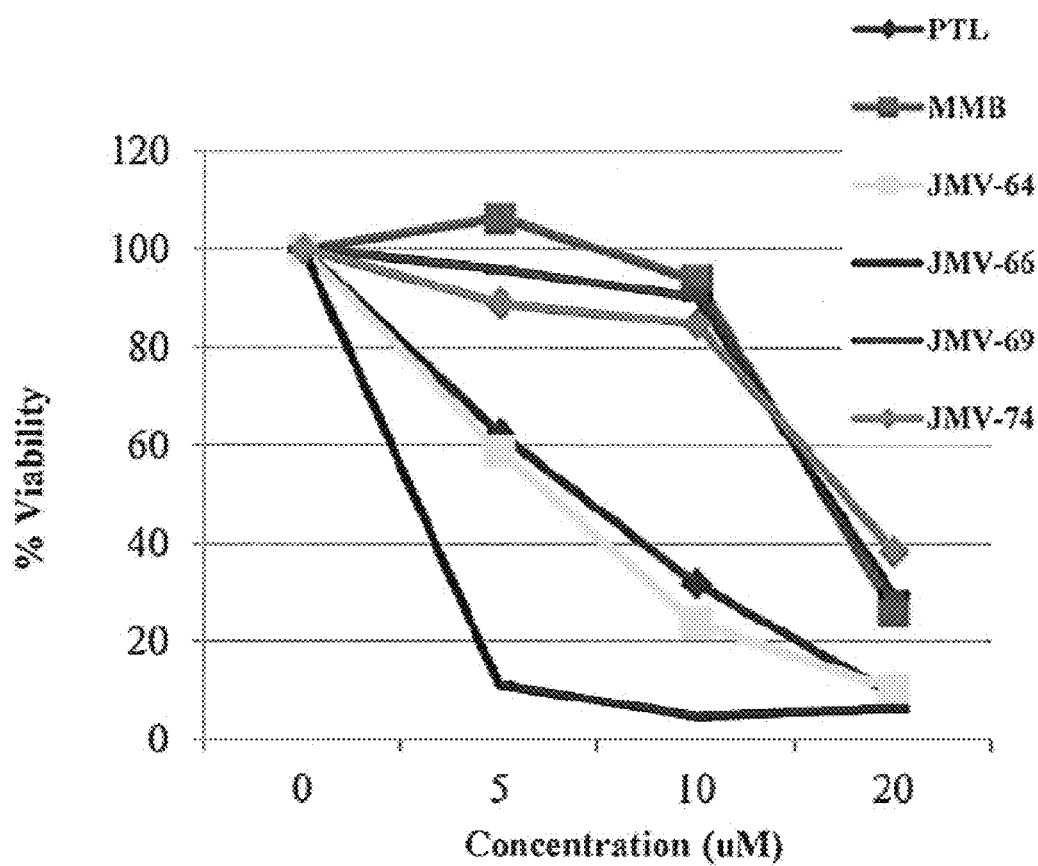
FIG. 1 shows the antileukemic activity of PTL, MMB, JMV 64, JMV 66, JMV 69, and JMV 74 against the AML 052308 cell line as a function of concentration (µM) and percentage of cell viability.
Figure 2:
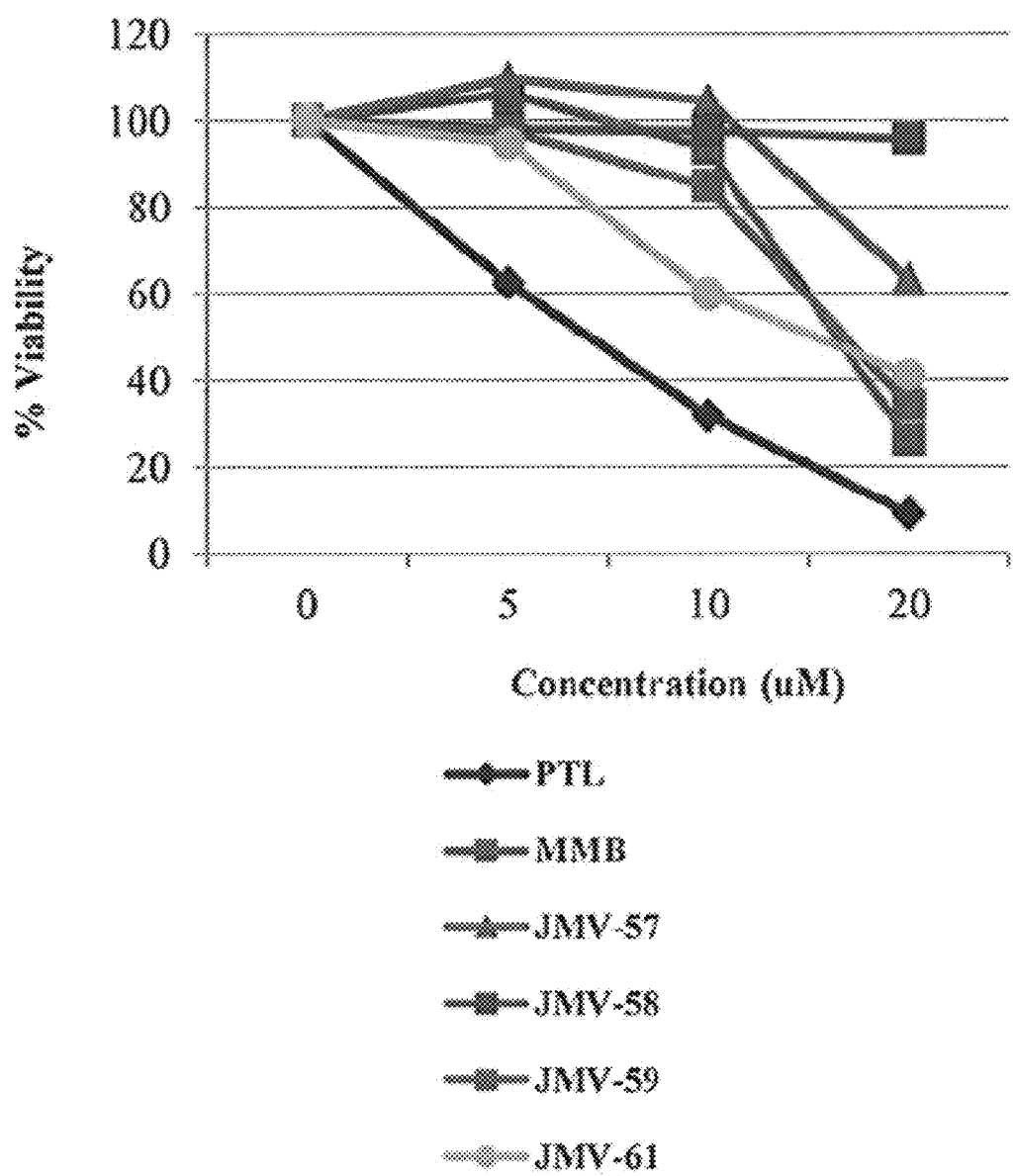
FIG. 2 shows the antileukemic activity of PTL, MMB, JMV 57, JMV 58, JMV 59, and JMV 61 against the AML 052308 cell line as a function of concentration (µM) and percentage of cell viability.
Figure 3:
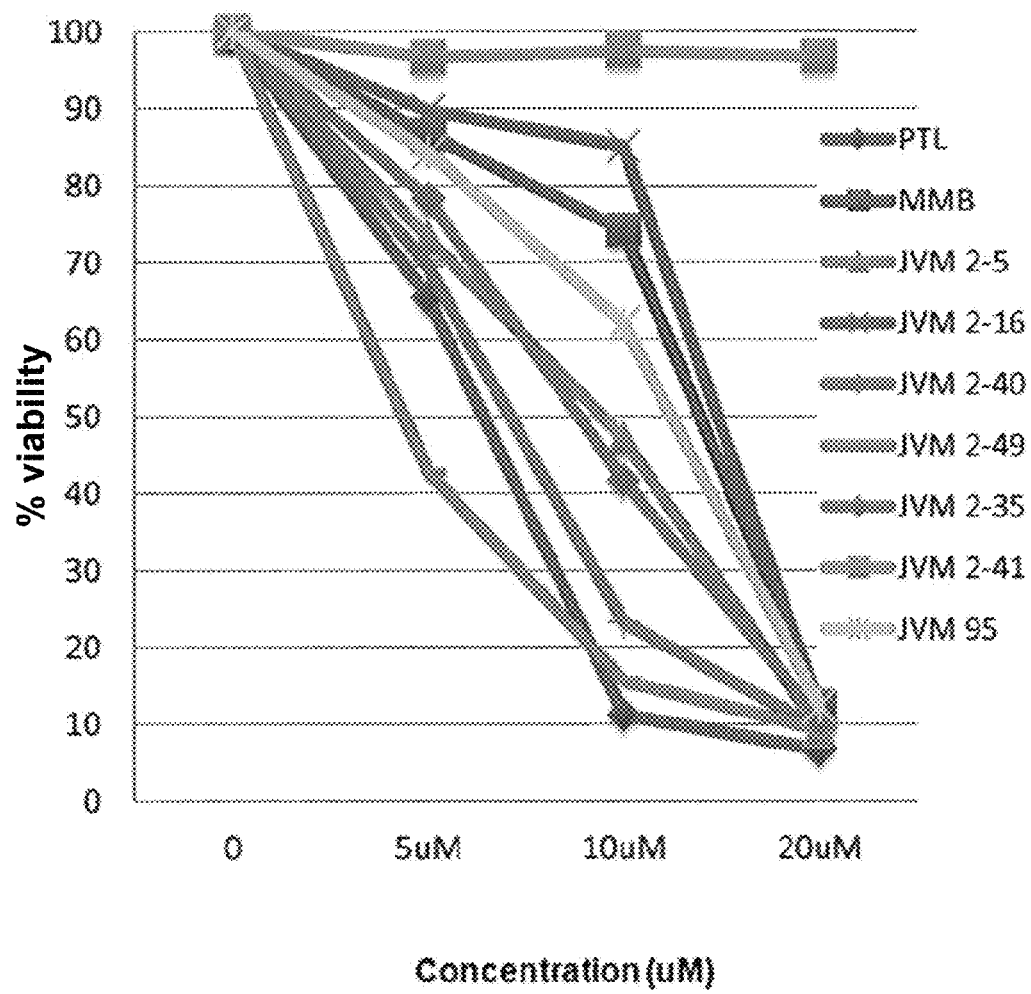
FIG. 3 shows the 24-hour M9's percentage of live cells relative to untreated cells for PTL, MMB, JMV 2-5, JMV 2-16, JMV 2-40, JMV 2-49, JVM 2-35, JVM 2-41, and JVM 95 as a function of concentration (µM).
Figure 4:
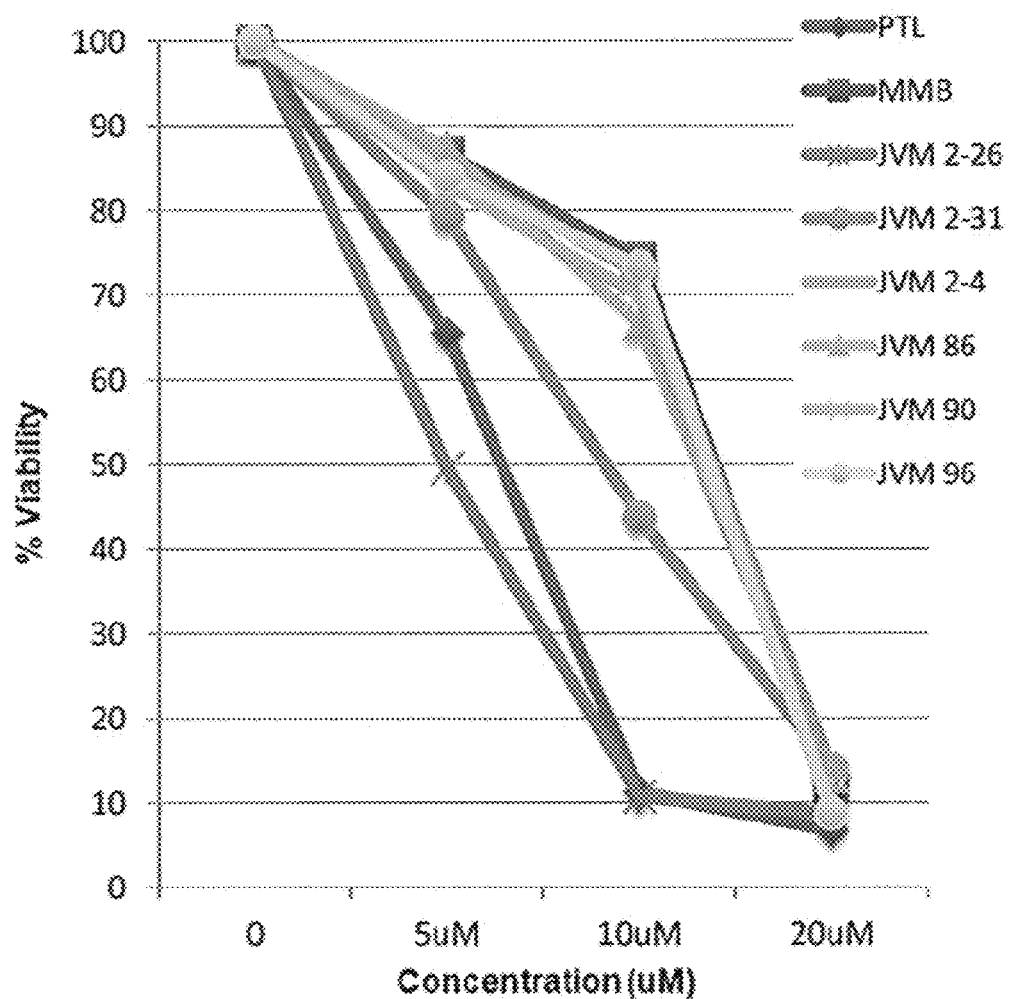
FIG. 4 shows the 24-hour M9's percentage of live cells relative to untreated cells for PTL, MMB, JMV 2-26, JMV 2-31, JMV 2-4, JMV 86, JVM 90, and JVM 96 as a function of concentration (µM).
Figure 5:
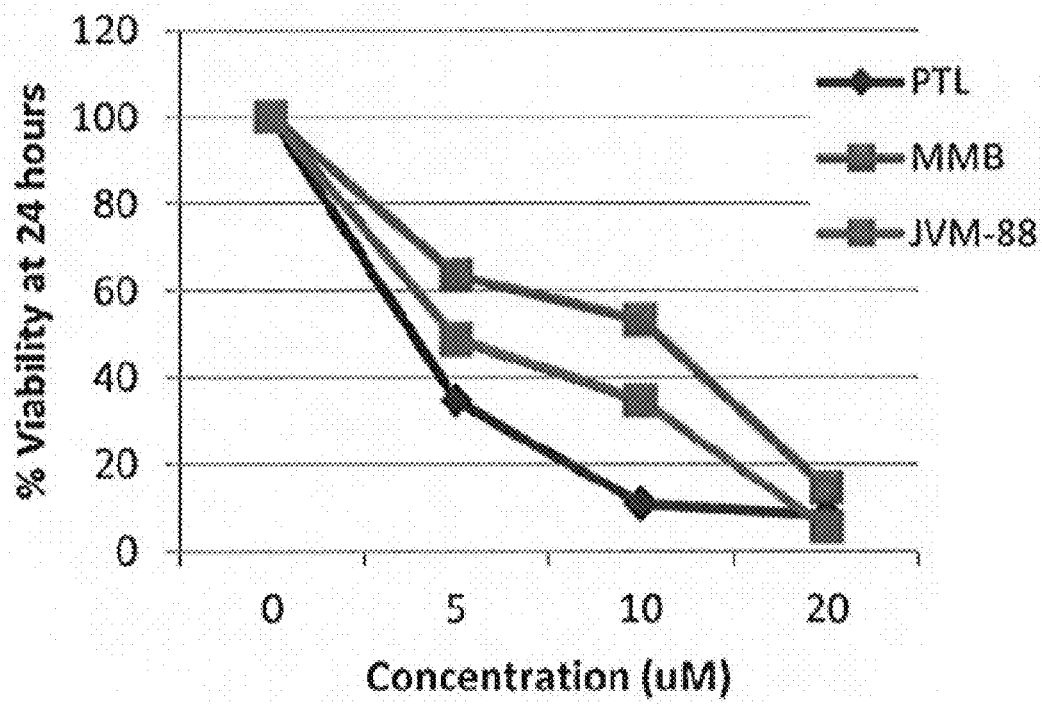
FIG. 5 shows the antileukemic activity of PTL, MMB, and JMV 88 against the M9 ENL cell line as a function of concentration (µM) and percentage of cell viability at 24 hours.
Figure 6:
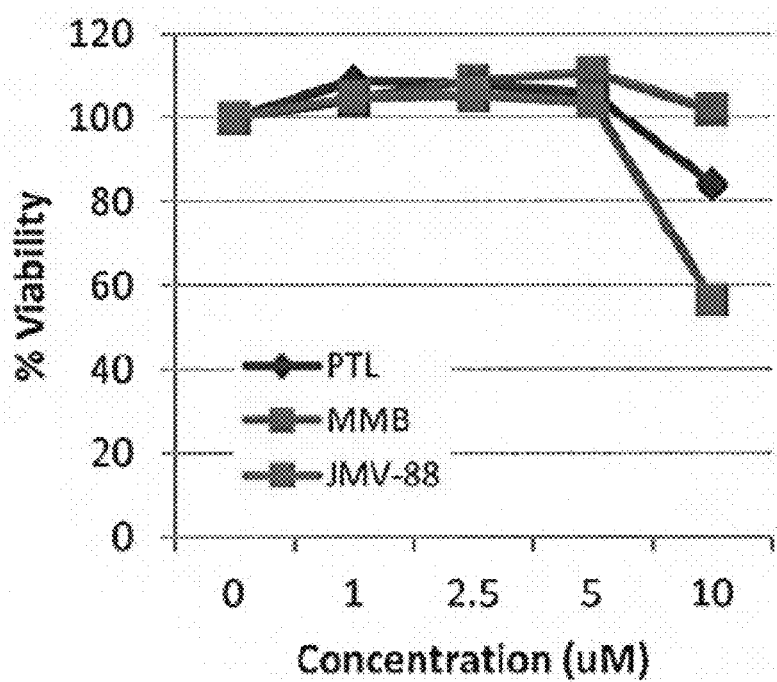
FIG. 6 shows the antileukemic activity of PTL, MMB, and JMV 88 against the AML 123009 cell line as a function of concentration (µM) and percentage of cell viability.
Figure 7:
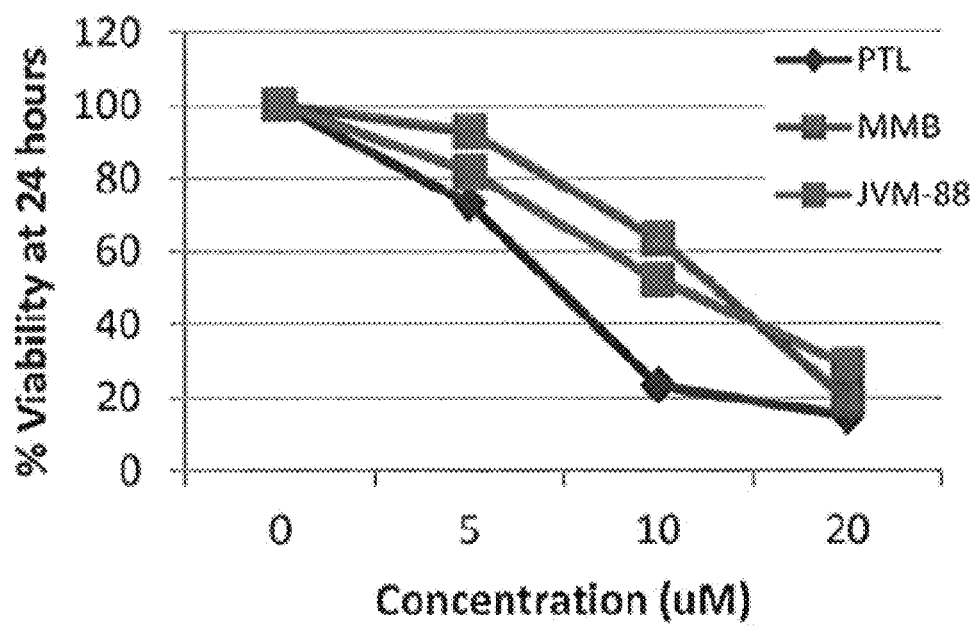
FIG. 7 shows the antileukemic activity of PTL, MMB, and JMV 88 against the AML 100510 cell line as a function of concentration (µM) and percentage of cell viability at 24 hours.

Provided herein are carbamate, thiocarbamate, and carbonate conjugates of MMB, which may be synthesized via an intermediate prepared by reacting MMB with carbonyldimidazole to afford MMB triazole (JVM 2-16, Example 10). This triazole intermediate may be reacted with various heterocyclic amines, including, for example, imidazole, morpholine, piperidine, pyrrolidine, triazole, and pyridine, to afford the corresponding carbamate conjugate. To prepare carbonate conjugates of MMB, MMB triazole may be reacted with hydroxyl-containing compounds, including methanol, ethanol, N,N-dimethylethanolamine, morpholinoethanol, and piperidinopropanol. A thiocarbamate conjugate (JVM-66, Example 6) may be synthesized by reacting MMB with thiocarbonyldiimidazole. Also provided herein are carbamate and carbonate conjugates of MMB, which may be synthesized via an intermediate prepared by reacting MMB with p-nitrophenylchloroformate to afford an ester of MMB. This ester derivative may be reacted with various heterocyclic amines, including, for example, imidazole, morpholine, piperidine, pyrrolidine, triazole, and pyridine, or hydroxyl-containing compounds, including methanol, ethanol, N,N-dimethylethanolamine, morpholinoethanol, and piperidinopropanol to afford the corresponding carbamate or carbonate conjugate.

Also provided herein are a series of novel ester and amide conjugates of MMB. Various heterocyclic carboxylate conjugates of MMB may be prepared from substituted indole, benzothiophene, benzofuran, nicotinic, thiophene, aromatic and aliphatic carboxylic acids. MMB may be reacted with various heterocyclic carboxylic acids in the presence of standard EDCI coupling conditions to furnish the respective MMB conjugates. Additionally, a variety of substituted heterocyclic aromatic and aliphatic amide conjugates of MMB were prepared by reaction of the appropriate amine with melampomagnolic acid, an oxidation product of MMB, or the appropriate carboxylic acid with an amine derivative of MMB. Melampomagnolic acid may be reacted with various heterocyclic amines under the same standard coupling conditions affording the corresponding MMB amide conjugates. Alternatively, an amine derivative of MMB may be reacted with various heterocyclic carboxylic acids under the same standard coupling conditions affording the corresponding MMB amide conjugates. Further, MMB may be reacted with various substituted heterocyclic 2-(1H-indo-3-yl)-2-oxoacetyl chlorides in the presence of triethylamine to afford the corresponding MMB ester conjugates.

These compounds were tested for anticancer activity against primary and non-primary AML cell lines and various solid tumor cell lines. Several compounds were efficient anticancer agents against the AML cell lines and various solid tumor cell lines. Notably, the compounds were significantly more potent than the parent compounds PTL and MMB.

In general, the compounds detailed herein include compounds comprising a melampomagnolide B (MMB) structure as diagrammed below. For the purposes of illustration, the ring atoms of MMB are numbered as shown below:

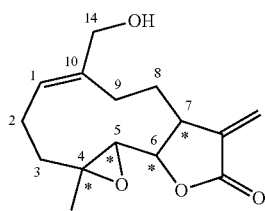 [SMILES: C=C1C(=O)OC2C1CC/C(CO)=C\CCC1(C)OC21]

MMB compounds have asymmetric centers. In particular, the MMB compounds may have at least four chiral carbons (designated by asterisks in the diagram above); namely, C4, C5, C6, and C7.

I. Compounds Comprising Formulas (I), (II), (III), (IV), (V), (VI), (VII) or (VIII)

In an aspect, provided herein are compounds comprising Formula (I):

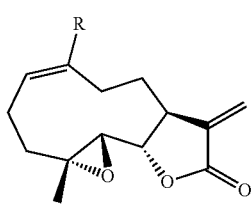

(I)

wherein:
R is selected from the group consisting of

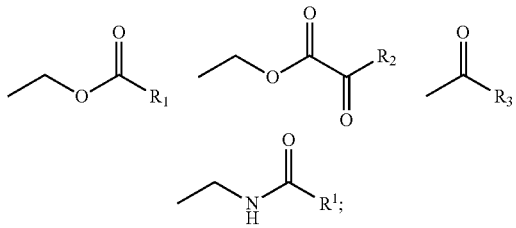

wherein:
$R_1$, $R_2$ and $R_3$ are independently selected from the group consisting of $-NR_6R_7$, $-OR_6$, $-O$-alkyl-$NR_6R_7$, $-SR_6$, $-S$-alkyl-$NR_6R_7$, alkyl-$C(O)NR_6R_7$, and -alkyl-$R_8$, substituted indoles, substituted heterocyclic aromatic, aromatic and aliphatic derivatives, and substituted amines;

$R_6$ is selected from the group consisting of hydrocarbyl, substituted hydrocarbyl, and $R_8$;

$R_7$ is selected from the group consisting of hydrogen, hydrocarbyl, and substituted hydrocarbyl;

$R_8$ is an optionally substituted nitrogen-containing heterocyclic ring;

one or more of $R_6$ and $R_7$ may form part of a ring or ring system chosen from the group consisting of heterocyclic, substituted heterocyclic, and combinations thereof; and when $R_7$ is hydrogen, $R_6$ is selected from the group consisting of alkyl, $R_8$, and substituted hydrocarbyl having at least one hydroxyl or $R_8$.

In some embodiments, $R_1$, $R_2$ and $R_3$ are selected from the group consisting of alkoxy, alkylamino, dialkylamino, dialkylaminoalkoxy, heterocyclylalkoxy, hydroxyalkylamino, heterocyclylamino, and heterocyclylalkylamino. In some embodiments, $R_1$, $R_2$ and $R_3$ may be selected from the group consisting of methylamino, dimethylamino, hydroxyhexylamino, hydroxyethylamino, pyrrolyl, pyrrolidinyl, pyridinyl, piperdinyl, pyrazinyl, piperazinyl, pyrimidinyl, imidazolyl, triazolyl, hydroxypiperdinyl, difluoropiperdinyl, triazolylamino, methylthiotriazolylamino, morpholinyl, morpholinylethylamino, pyridinylmethylamino, piperdinylethylamino, pyridinylethylamino, morpholinylpropylamino, imidiazolylpropylamino, methoxy, dimethylaminoethoxy, piperdinylpropoxy, piperdinylethoxy, pyrrolidinylethoxy, morpholinylethyoxy, piperidinylethoxyhydroxyethylthio, and piperdinylethyl. In other embodiments, $R_1$, $R_2$ and $R_3$ may be selected from the group consisting of imidazolylpropylaminocarbonylethylcarbonyl, difluoropiperinylcarbonylethylcarbonyl, methylthio-triazolylaminocarbonylethylcarbonyl, chloropyridinylmethylaminocarbonylethylcarbonyl, methylpiperdinylcarbonylethylcarbonyl, and methylpiperazinylcarbonylethylcarbonyl.

In certain embodiments, $R_1$ is selected from the group consisting of substituted indoles, substituted heterocyclic aromatic, aromatic and aliphatic derivatives.

In certain embodiments, $R_2$ is selected from the group consisting of substituted indoles.

In certain embodiments, $R_3$ is selected from the group consisting of substituted amines.

In another aspect, provided herein are a compound comprising Formula (II) or (III):

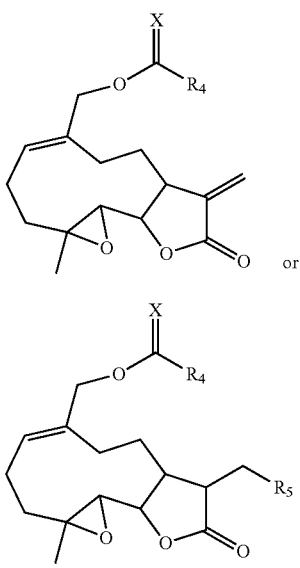

(II)

or

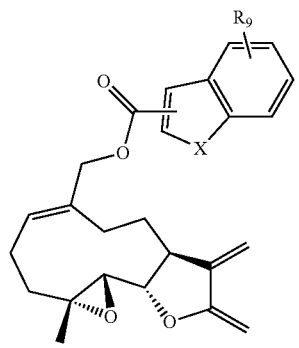

(III)

wherein:

X is O or S;

$R_4$ and $R_5$ are independently selected from the group consisting of $-NR_6R_7$, $-OR_6$, $-O$-alkyl-$NR_6R_7$, $-SR_6$, $-S$-alkyl-$NR_6R_7$, alkyl-$C(O)NR_6R_7$, and -alkyl-$R_8$;

$R_6$ is selected from the group consisting of hydrocarbyl, substituted hydrocarbyl, and $R_8$;

$R_7$ is selected from the group consisting of hydrogen, hydrocarbyl, and substituted hydrocarbyl;

$R_8$ is an optionally substituted nitrogen-containing heterocyclic ring;

one or more of $R_6$ and $R_7$ may form part of a ring or ring system chosen from the group consisting of heterocyclic, substituted heterocyclic, and combinations thereof; and when $R_7$ is hydrogen, $R_6$ is selected from the group consisting of alkyl, $R_8$, and substituted hydrocarbyl having at least one hydroxyl or $R_8$.

In an exemplary embodiment of a compound comprising Formula (II), X is O; $R_4$ is $NR_6R_7$; and $R_6$, $R_7$ and $R_8$ are as described above.

In some embodiments, $R_4$ and $R_5$ may be selected from the group consisting of alkoxy, alkylamino, dialkylamino, dialkylaminoalkoxy, heterocyclylalkoxy, hydroxyalkylamino, heterocyclylamino, and heterocyclylalkylamino. In some exemplary embodiments, $R_4$ and $R_5$ may be selected from the group consisting of methylamino, dimethylamino, hydroxyhexylamino, hydroxyethylamino, pyrrolyl, pyrrolidinyl, pyridinyl, piperdinyl, pyrazinyl, piperazinyl, pyrimidinyl, imidazolyl, triazolyl, hydroxypiperdinyl, difluoropiperdinyl, triazolylamino, methylthiotriazolylamino, morpholinyl, morpholinylethylamino, pyridinylmethylamino, piperdinylethylamino, pyridinylethylamino, morpholinylpropylamino, imidiazolylpropylamino, methoxy, dimethylaminoethoxy, piperdinylpropoxy, piperdinylethoxy, pyrrolidinylethoxy, morpholinylethyoxy, piperidinylethoxyhydroxyethylthio, and piperdinylethyl. In other exemplary embodiments, $R_4$ and $R_5$ may be independently selected from the group consisting of imidazolyl-propylaminocarbonylethylcarbonyl, difluoropiperinylcarbonylethylcarbonyl, methylthio-triazolylaminocarbonylethylcarbonyl, chloropyridinylmethylaminocarbonylethylcarbonyl, methylpiperdinylcarbonylethylcarbonyl, and methylpiperazinylcarbonylethylcarbonyl. In a particular embodiment, $R_4$ may be $R_8$, and $R_5$ may be dialkylamino. In still other embodiments, one or more $R_4$, $R_5$, $R_6$, $R_7$, or $R_8$ may be substituted with at least one selected from the group consisting of methyl, ethyl, propyl, cyano, $C_1$-$C_3$-alkylamino, carboxyl, hydroxyl, trifluoromethyl, thio, alkylthio, and halogen.

In another aspect, provided herein are compounds comprising Formula (IV):

(IV)

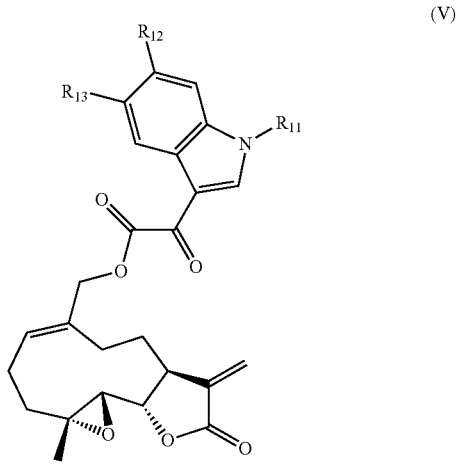

wherein:

X is selected from the group consisting of S, O, NH, $NR_{10}$;

$R_9$ is selected from the group consisting of OMe, Cl, Br and F; and $R_{10}$ is selected from the group consisting of H, $CH_3$, benzyl, substituted benzyl, benzoyl, substituted benzoyl, and benzylsulfonyl and substituted benzylsulfonyl.

In still another aspect, provided herein are compounds comprising Formula (V):

(V)

wherein:

$R_{11}$ is selected from the group consisting of H, $CH_3$, benzyl, substituted benzyl, benzoyl, substituted benzoyl, and benzylsulfonyl and substituted benzylsulfonyl; and $R_{12}$ and $R_{13}$ are independently selected from the group consisting of H, F, Cl, Br, $OCH_3$, CN, $CH_3$, $NO_2$ and $COOCH_3$.

In still another aspect, provided herein are compounds comprising Formula (VI):

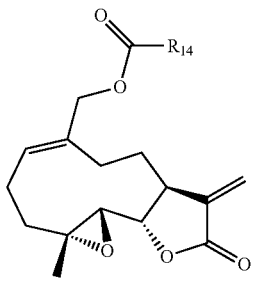

(VI)

wherein:
R$_{14}$ is selected from the group consisting of 2-thiophenyl, 3-thiophenyl, 2-pyrazine, 3-pyrazine, 2-amino nicotinic acid, indole-3-acetic acid, indole-3-acrylic acid.

In still another aspect, provided herein are compounds comprising Formula (VII):

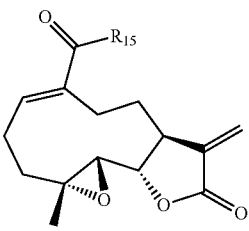

(VII)

wherein:
R$_{15}$ is selected from the group consisting of:

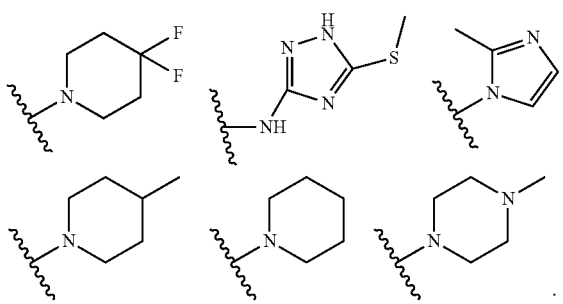

In yet still another aspect, provided herein are compounds comprising Formula (VIII):

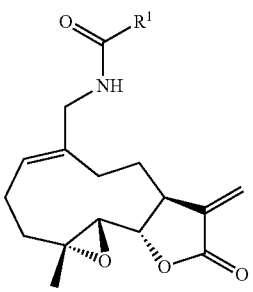

(VIII)

wherein:
R$_1$ is selected from the group consisting of R$_1$ is selected from the group consisting of substituted indoles, substituted heterocyclic aromatic, aromatic and aliphatic derivatives.

(a) Downstream Applications

In some embodiments, the compound comprising Formula (I), (II), (III), (IV), (V), (VI), (VII) or (VIII) may be converted into a pharmaceutically acceptable salt. "Pharmaceutically acceptable salts" are salts commonly used to form alkali metal salts and to form addition salts of free acids or free bases. The nature of the salt may vary, provided that it is pharmaceutically acceptable.

Suitable pharmaceutically acceptable acid addition salts of compounds comprising Formula (I), (II), (III), (IV), (V), (VI), (VII) or (VIII) may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, aliphatic, heterocyclic, carboxylic and sulfonic classes of organic acids, examples of which are oxalic, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with the any compound comprising Formula (I), (II), (III), (IV), (V), (VI), (VII) or (VIII).

(b) Stereochemistry

The compounds comprising Formula (I), (II), (III), (IV), (V(VI), (VII) or (VIII) may independently have an optical activity of (–) or (+). In particular, the configuration of C4, C5, C6, and C7, respectively, may be RRRR, RRSR, RRRS, RRSS, RSRR, RSSR, RSRS, RSSS, SRRR, SRSR, SRRS, SRSS, SSRR, SSSR, SSRS, or SSSS.

II. Processes for Preparing Compounds Comprising Formula (I), (II), (III), (IV), (V), (VI), (VII) or (VIII)

In particular, provided herein are processes for preparing a compound comprising Formula (II) or (III). In general, the process comprises contacting MMB with an appropriate reagent to form a compound comprising Formula (II) or (III).

In an aspect, provided herein are processes for preparing a compound comprising Formula (II) or (III). The process comprises (a) contacting MMB with a triazole reagent to form a triazole intermediate. The process continues with (b) contacting the triazole intermediate with a compound comprising formula R$^4$—H to form a compound comprising Formula (II) or (III).

In another aspect, provided herein are processes for preparing a carbamate or carbonate compound comprising Formula (II). The process comprises (a) contacting MMB with p-nitrophenylchloroformate to form an ester derivative of MMB. The process continues with (b) contacting the ester derivative of MMB with a compound comprising formula R⁴—H to form a compound comprising Formula (II).

In still another aspect, provided herein are processes for preparing an amide compound comprising Formula (II). The process comprises (a) contacting MMB with an acid anhydride to form a carboxylic acid derivative. The process continues with (b) contacting the carboxylic acid derivative with a compound comprising formula R⁴—H to form a compound comprising Formula (II).

In still yet another aspect, provided herein are processes for preparing a compound comprising Formula (I), (II), (IV) or (VI). The process generally comprises (a) contacting MMB with a carboxylic acid to form a compound comprising Formula (I), (II), (IV) or (VI). Optionally, prior to step (a), an ester may be converted into the corresponding carboxylic acid prior to conjugation with MMB.

In a different aspect, provided herein are processes for preparing a compound comprising Formula (I), (II), (V) or (VI). The process generally comprises (a) contacting MMB with an acyl chloride to form a compound comprising Formula (I), (II), (V) or (VI). Optionally, prior to step (a), a compound may be converted into the corresponding acyl chloride prior to conjugation with MMB.

In certain aspects, provided herein are processes for preparing a compound comprising Formula (I) or (VII). The process generally comprises (a) contacting melampomagnolic acid with a heterocyclic amine to form a compound comprising Formula (I) or (VII).

In other aspects, provided herein are processes for preparing a compound comprising Formula (I) or (VIII). The process generally comprises (a) contacting an amine derivative of MMB with a carboxylic acid to form a compound comprising Formula (I) or (VIII).

(a) Carbamate and Carbonate Derivatives of MMB Via a Triazole Intermediate

Carbamate derivatives may be synthesized using, for example, phosgene, acid chlorides, carbamoyl chloride, or 1,1-carbonyldiimidazole (CDI). In some embodiments, CDI may form a carbamate ester on MMB. CDI advantageously provides easy handling, low expense, and relatively low toxicity. In particular embodiments, imidazole carboxylic esters may be formed by reaction of CDI with MMB. In this reaction imidazole, while a byproduct, also participated in an unexpected Michael addition reaction with the MMB exocyclic double bond of the carbamate product (Scheme 1).

Scheme 1. Synthesis of imidazole carbamate derivative of MMB

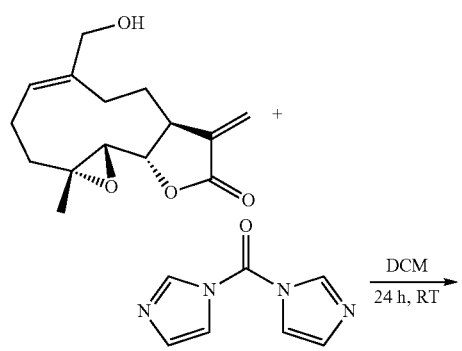

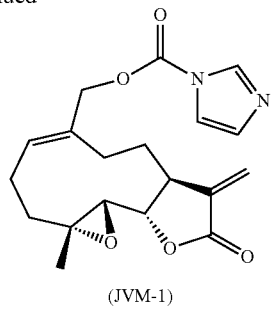

(JVM-1)

Thiocarbamate derivatives of MMB may be formed by reacting MMB with thiocarbonyl diimidazole dissolved in dichloromethane. If the reaction is maintained for 3-4 h, the major product was the Michael adduct JVM 66A. If the reaction is run for a shorter time (e.g., 1 hour), the thiocarbamate (JVM 66) was the major product (Scheme 2). A detailed synthesis of JVM 66 is provided below at Example 6.

Scheme 2. Synthesis of thiocarbamate derivatives of MMB

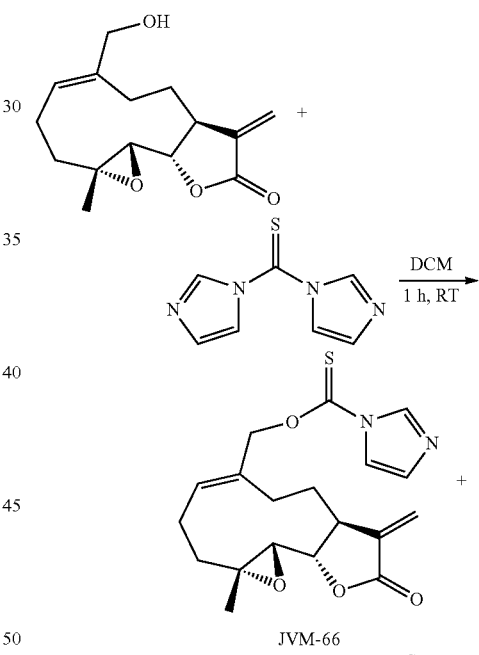

JVM-66

JVM-66A

The triazole derivative of MMB (JVM 2-16) was prepared by reacting MMB with carbonylditriazole (CTD) dissolved in dichloromethane. The triazole byproduct does not participate in a Michael addition reaction because triazole has only weak nucleophilic properties. The triazole intermediate (JVM 2-16) reacted with various heterocyclic amines and alcohols to form a variety of carbamate and carbonate derivatives (Scheme 3). A detailed synthesis of JVM 2-16 is provided below at Example 10.

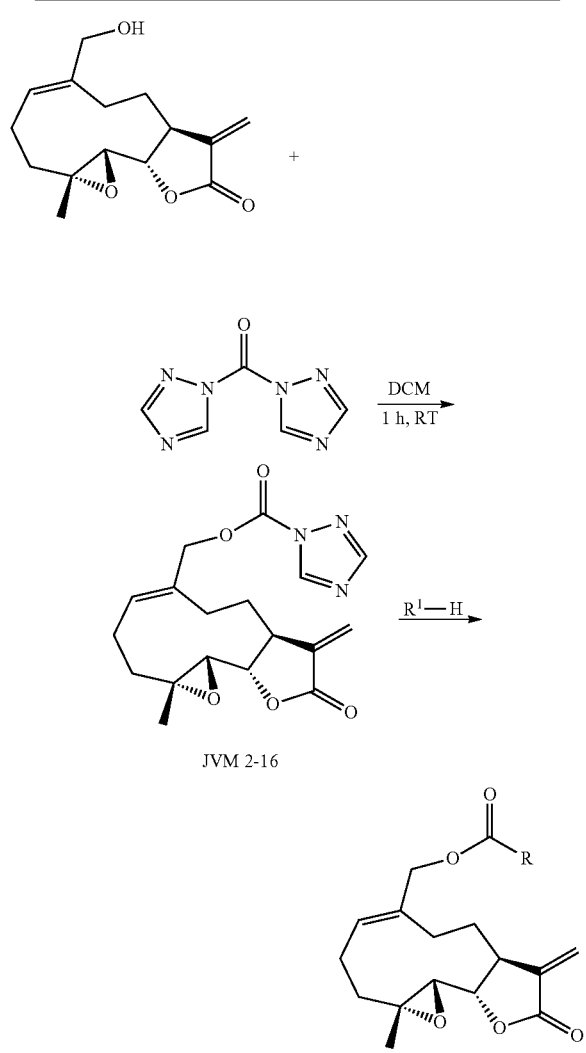

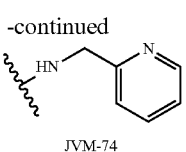

In still other embodiments, the triazole intermediate (JVM 2-16) may be reacted with mercaptoethanol in the presence of triethylamine to afford JVM 2-41. A detailed synthesis of JVM 2-41 is provided below at Example 15.

In particular, provided herein are processes for preparing a compound comprising Formula (II) or (III). The process comprises (a) contacting MMB with a triazole reagent to form a triazole intermediate. The process continues with (b)

contacting the triazole intermediate with a compound comprising formula $R^4$—H to form a compound comprising Formula (II) or (III). This process is illustrated according to the following reaction scheme:

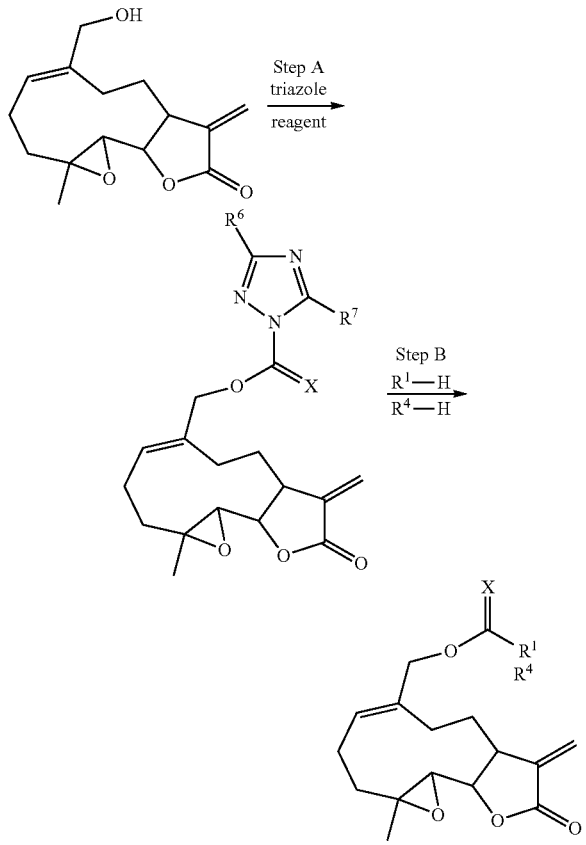

wherein:

X is O or S, $R_4$ is selected from the group consisting of —$NR_6R_7$, —$OR_6$, —O-alkyl-$NR_6R_7$, —$SR_6$, —S-alkyl-$NR_6R_7$, alkyl-C(O)$NR_6R_7$, and -alkyl-$R_8$;

$R_6$ is selected from the group consisting of hydrocarbyl, substituted hydrocarbyl, and $R_8$;

$R_7$ is selected from the group consisting of hydrogen, hydrocarbyl, and substituted hydrocarbyl;

$R_8$ is an optionally substituted nitrogen-containing heterocyclic ring;

one or more of $R_6$ and $R_7$ may form part of a ring or ring system chosen from the group consisting of heterocyclic, substituted heterocyclic, and combinations thereof; and when $R_7$ is hydrogen, $R_6$ is selected from the group consisting of alkyl, $R_8$, and substituted hydrocarbyl having at least one hydroxyl or $R_8$.

(i) Step (a)—Reaction Mixture

Step (a) of the process comprises contacting MMB with a triazole reagent to form a triazole intermediate. The process commences with the formation of a reaction mixture comprising MMB, which is detailed above, the triazole reagent, and optionally a solvent system.

The triazole reagent may be any compound which reacts with a hydroxyl group to provide a triazolyl carbamate. Non-limiting examples of suitable triazole reagents include carbonylditriazole (such as 1,1'-carbonyl-di-(1,2,4-triazole) and thiocarbonylditriazole. Another possible synthetic approach to the synthesis of the imidazole carbamate analog of MMB is by utilizing carbonyldiimidazole as a reagent instead of carbonylditriazole.

The amounts of triazole reagent that are contacted with MMB may vary. In general, the mole to mole ratio of MMB to triazole agent may range from about 1:0.2 to about 1:15. In certain embodiments, the mole to mole ratio of MMB to the triazole reagent may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB to the triazole reagent may range from about 1:0.7 to about 1:3.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-di methylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

In general, the volume to mass ratio of the solvent to MMB ranges from about 1:1 to about 100:1. In various embodiments, the volume to mass ratio of the solvent to MMB may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB may range from about 20:1 to about 30:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount MMB, and a significantly increased amount of the triazole intermediate compared to the amounts of each present at the beginning of the reaction. Typically, the amount MMB remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 5 minutes to about 15 minutes. In other embodiments, the reaction may be allowed to proceed about 45 minutes to about 75 minutes. In still other embodiments, the reaction may be allowed to proceed about 18 hours to about 36 hours.

Generally, the triazole intermediate is not isolated and step (b) of the process proceeds in the same reaction pot or reactor. In some embodiments, the triazole intermediate may be isolated from the reaction mixture using techniques known to those of skill in the art. Non-limiting examples of suitable techniques include precipitation, extraction, evaporation, distillation, chromatography, and crystallization.

The yield of the triazole intermediate can and will vary. Typically, the yield of the triazole intermediate may be at least about 40%. In one embodiment, the yield of the triazole intermediate may range from about 40% to about 60%. In another embodiment, the yield of the triazole intermediate may range from about 60% to about 80%. In a further embodiment, the yield of the triazole intermediate may range from about 80% to about 90%. In still another embodiment, the yield of the triazole intermediate may be greater than about 90%, or greater than about 95%.

(iii) Step (b)—Reaction Mixture

Step (b) of the process continues with (b) contacting the triazole intermediate with a compound comprising formula $R^4$—H to form a compound comprising Formula (I) or (II). The process commences with the formation of a reaction mixture comprising the triazole intermediate, which is detailed above, a compound comprising the formula $R^4$—H, and optionally a solvent system.

In some embodiments, the compound comprising formula $R^4$—H may be selected from the group consisting of imidazole, benzimidazole, morpholine, piperidine, pyrrole, pyrrolidine, triazole, tetrazole, piperazine, pyridine, pyrazoloimidazole, methanol, ethanol, N,N-dimethylethanolamine, morpholinoethanol, and piperidinopropanol.

The amounts of the compound comprising formula $R^4$—H that are contacted with the triazole intermediate may vary. In general, the mole to mole ratio of the triazole intermediate to the compound comprising formula $R^4$—H may range from about 1:0.2 to about 1:15. In certain embodiments, the mole to mole ratio of the triazole intermediate to the compound comprising formula $R^4$—H may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the triazole intermediate to the compound comprising formula $R^4$—H may range from about 1:0.7 to about 1:3.

Contact with the compound comprising formula $R^4$—H generally is conducted in the presence of a solvent or solvent system. Suitable solvents are detailed above in Section II(a)(i). In exemplary embodiments, the solvent may be dichloromethane, chloroform, or combinations thereof. In general, the volume to mass ratio of the solvent to the triazole intermediate ranges from about 1:1 to about 100:1. In various embodiments, the volume to mass ratio of the solvent to the triazole intermediate may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the triazole intermediate may range from about 20:1 to about 30:1.

(iv) Step (b)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. Typically, the amount of the triazole intermediate remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 20 minutes to about 40 minutes. In other embodiments, the reaction may be allowed to proceed about 8 hours to about 12 hours.

The yield of the compound comprising Formula (II) or (III) can and will vary. Typically, the yield of the compound comprising Formula (II) or (III) may be at least about 40%. In one embodiment, the yield of the compound comprising Formula (II) or (III) may range from about 40% to about 60%. In another embodiment, the yield of the compound comprising Formula (II) or (III) may range from about 60% to about 80%. In a further embodiment, the yield of the compound comprising Formula (II) or (III) may range from about 80% to about 90%. In still another embodiment, the yield of the compound comprising Formula (II) or (III) may be greater than about 90%, or greater than about 95%.

(b) Carbamate and Carbonate Derivatives of MMB Via an Ester Derivative

In still yet other embodiments, MMB (3) may be reacted with p-nitrophenylchloroformate (4) in the presence of triethylamine to form the p-nitrophenyloxycarbonyl ester of MMB (5). The p-nitrophenyloxycarbonyl ester of MMB may then be reacted with various primary and secondary heterocyclic amines to afford carbamate analogs of MMB (6) (Scheme 4).

Scheme 4. Synthesis of carbamoylated MMB analogs 6a-6g:

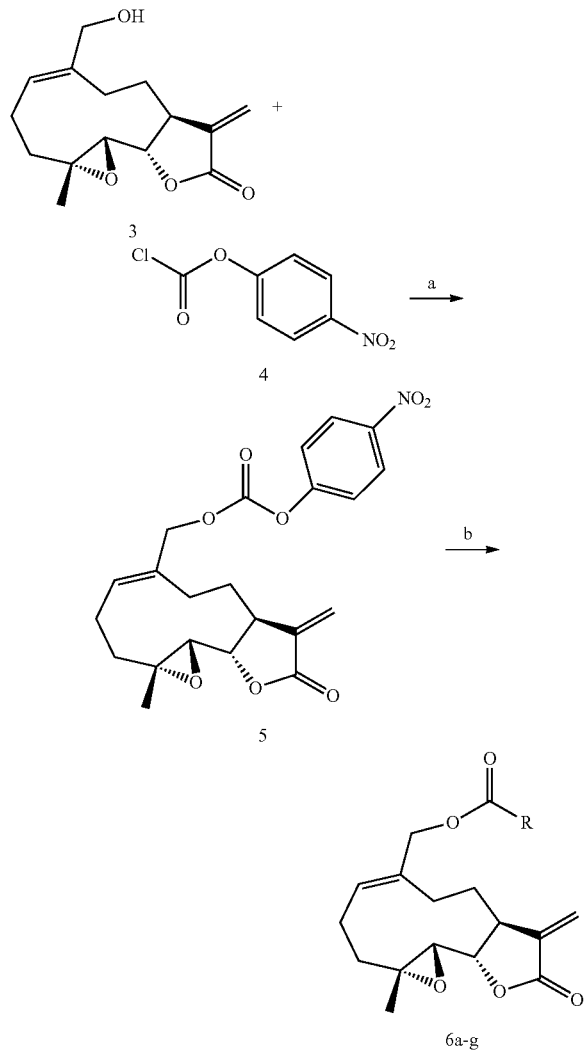

Reagents and conditions: (a) CH$_2$Cl$_2$, triethylamine, rt, 24 h; (b) CH$_2$Cl$_2$, heterocyclic amines, rt, 5-12 h.

In particular, provided herein are processes for preparing a carbamate or carbonate compound comprising Formula (II) or (III). The process comprises (a) contacting MMB (3) with p-nitrophenylchloroformate to form an ester derivative of MMB (e.g. (5)). The process continues with (b) contacting the ester derivative of MMB with a compound comprising formula $R^4$—H to form a compound comprising Formula (II) or (III).

(i) Step (a)—Reaction Mixture

Step (a) of the process comprises contacting MMB with p-nitrophenylchloroformate to form an ester derivative of MMB (e.g. (5)). The process commences with the formation of a reaction mixture comprising MMB, which is detailed above, p-nitrophenylchloroformate, and optionally a solvent system.

The amounts of p-nitrophenylchloroformate that are contacted with MMB may vary. In general, the mole to mole ratio of MMB to p-nitrophenylchloroformate may range from about 1:0.2 to about 1:15. In certain embodiments, the mole to mole ratio of MMB to p-nitrophenylchloroformate may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB to p-nitrophenylchloroformate may range from about 1:0.7 to about 1:3. In an exemplary embodiment, the mole to mole ratio of MMB to p-nitrophenylchloroformate may be about 1:0.7.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-di methylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, NaBO$_3$), di- and tri-basic phosphate salts, (such as, for example, Na$_2$HPO$_4$ and NaPO$_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In a specific embodiment, the proton acceptor is triethylamine. The amount of proton acceptor included in the reaction can and will vary, but can be readily determined by a person of ordinary skill in the art.

In general, the volume to mass ratio of the solvent to MMB ranges from about 1:1 to about 100:1. In various embodiments, the volume to mass ratio of the solvent to MMB may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB may range from about 20:1 to about 30:1. In other exemplary embodiments, the volume to mass ratio of the solvent to MMB may range from about 10:1 to about 20:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of MMB, and a significantly increased amount of the carboxylic acid derivative compared to the amounts of each present at the beginning of the reaction. Typically, the amount of MMB remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 5 minutes to about 15 minutes. In other embodiments, the reaction may be allowed to proceed about 45 minutes to about 75 minutes. In still other embodiments, the reaction may be allowed to proceed about 18 hours to about 36 hours. In an exemplary embodiment, the reaction may be allowed to proceed about 24 hours.

Generally, the ester derivative is not isolated and step (b) of the process proceeds in the same reaction pot or reactor. In some embodiments, the ester derivative may be isolated from the reaction mixture using techniques known to those of skill in the art. Non-limiting examples of suitable techniques include precipitation, extraction, evaporation, distillation, chromatography, and crystallization.

The yield of the ester derivative can and will vary. Typically, the yield of the ester derivative may be at least about 40%. In one embodiment, the yield of the ester derivative may range from about 40% to about 60%. In another embodiment, the yield of the ester derivative may range from about 60% to about 80%. In a further embodiment, the yield of the ester derivative may range from about 80% to about 90%. In still another embodiment, the yield of the ester derivative may be greater than about 90%, or greater than about 95%.

(iii) Step (b)—Reaction Mixture

Step (b) of the process continues with (b) contacting the ester derivative with a compound comprising formula $R^4$—H to form a compound comprising Formula (II) or (III). The process commences with the formation of a reaction mixture comprising the ester derivative, which is detailed above, a compound comprising the formula $R^4$—H, and optionally a solvent system.

In some embodiments, the compound comprising formula $R^4$—H may be selected from the group consisting of imidazole, benzimidazole, morpholine, piperidine, pyrrole, pyrrolidine, triazole, tetrazole, piperazine, pyridine, pyrazoloimidazole, methanol, ethanol, N,N-dimethylethanolamine, morpholinoethanol, and piperidinopropanol.

The amounts of the compound comprising formula $R^4$—H that are contacted with the ester derivative may vary. In general, the mole to mole ratio of the ester derivative to the compound comprising formula $R^4$—H may range from about 1:0.2 to about 1:15. In certain embodiments, the mole to mole ratio of the ester derivative to the compound comprising formula $R^4$—H may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the ester derivative to the compound comprising formula $R^1$—H may range from about 1:0.7 to about 1:3. In an exemplary, the mole to mole ratio of the ester derivative to the compound comprising formula $R^4$—H may be about 1:1.

Contact with the compound comprising formula $R^4$—H generally is conducted in the presence of a solvent or solvent system. Suitable solvents are detailed above in Section II(b)(i). In exemplary embodiments, the solvent may be dichloromethane, chloroform, or combinations thereof. In general, the volume to mass ratio of the solvent to the ester derivative ranges from about 1:1 to about 100:1. In various embodiments, the volume to mass ratio of the solvent to the ester derivative may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the ester derivative may range from about 20:1 to about 30:1. In another exemplary embodiment, the volume to mass ratio of the solvent to the ester derivative may range from about 10:1 to about 20:1.

(iv) Step (b)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. Typically, the amount of the ester derivative remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 20 minutes to about 40 minutes. In other embodiments, the reaction may be allowed to proceed about 5 hours to about 18 hours. In exemplary embodiments, the reaction may be allowed to proceed about 5 hours to about 12 hours.

The yield of the compound comprising Formula (II) or (III) can and will vary. Typically, the yield of the compound comprising Formula (II) or (III) may be at least about 40%. In one embodiment, the yield of the compound comprising Formula (II) or (III) may range from about 40% to about 60%. In another embodiment, the yield of the compound comprising Formula (II) or (III) may range from about 60% to about 80%. In a further embodiment, the yield of the compound comprising Formula (II) or (III) may range from about 80% to about 90%. In still another embodiment, the yield of the compound comprising Formula (II) or (III) may be greater than about 90%, or greater than about 95%.

(c) Amide Derivatives of MMB Via an Acid Anhydride

In other embodiments, MMB may be reacted with succinic anhydride in presence of triethylamine to afford a carboxylic acid derivative of MMB, JVM 67. The MMB carboxylic acid derivative may be reacted with heterocyclic amines to afford the corresponding amide derivatives of MMB (Scheme 5). A detailed synthesis of JVM 67 is provided below at Example 7.

Scheme 5. Synthesis of amide derivatives of MMB

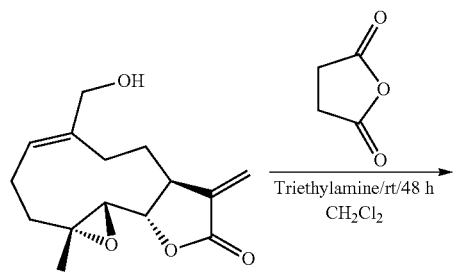

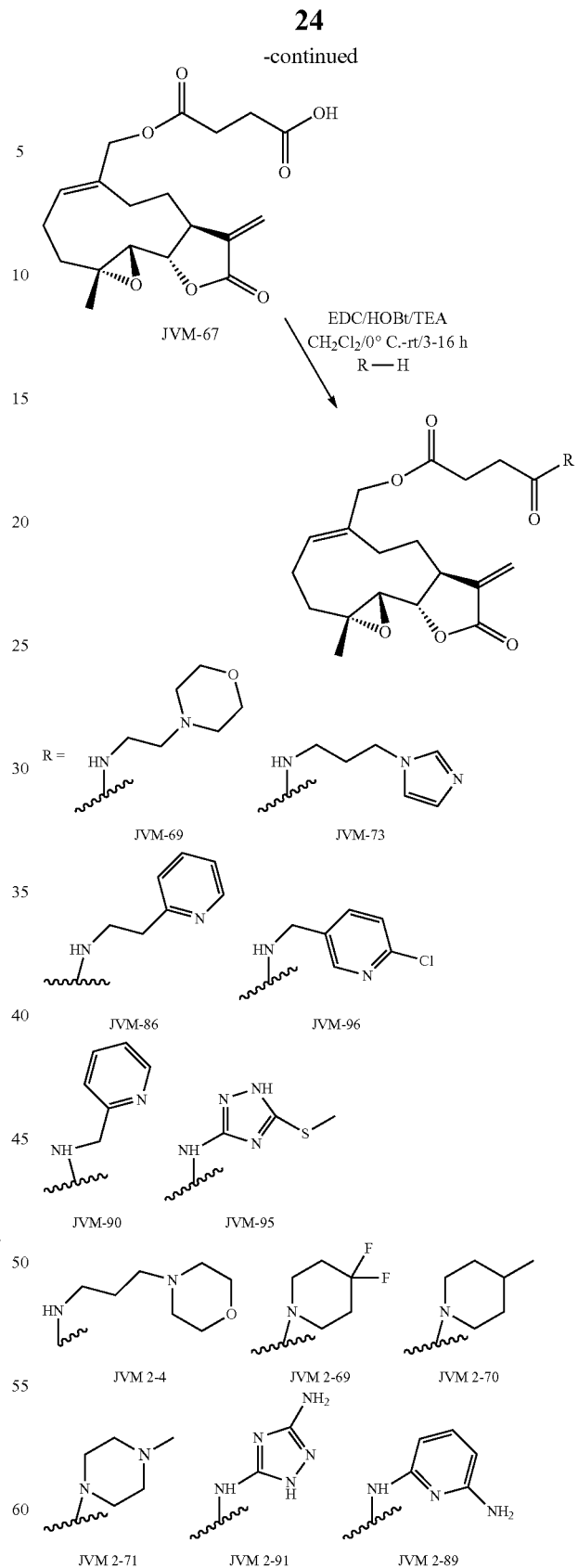

In particular, provided herein are processes for preparing an amide compound comprising Formula (II) or (III). The process comprises (a) contacting MMB with an acid anhydride to form a carboxylic acid derivative. The process continues with (b) contacting the carboxylic acid derivative with a compound comprising formula $R^4$—H to form a compound comprising Formula (II) or (III).

(i) Step (a)—Reaction Mixture

Step (a) of the process comprises contacting MMB with an acid anhydride to form a carboxylic acid derivative. The process commences with the formation of a reaction mixture comprising MMB, which is detailed above, the acid anhydride, and optionally a solvent system.

The acid anhydride may be any compound which reacts with a hydroxyl group to provide a carboxylic acid derivative. A suitable acid anhydride is a compound that has two acyl groups bonded to the same oxygen atom. In a preferred embodiment, the acid anhydride is a cyclic anhydride. Non-limiting examples of suitable acid anhydrides include succinic anhydride, maleic anhydride, itaconic anhydride, citraconic anhydride and 2-pentendioic anhydride. In an exemplary embodiment, the acid anhydride is succinic anhydride.

The amounts of acid anhydride that are contacted with MMB may vary. In general, the mole to mole ratio of MMB to acid anhydride may range from about 1:0.2 to about 1:15. In certain embodiments, the mole to mole ratio of MMB to acid anhydride may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB to acid anhydride may range from about 1:0.7 to about 1:3. In an exemplary embodiment, the mole to mole ratio of MMB to acid anhydride may range from about 1:1.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-di methylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In a specific embodiment, the proton acceptor is triethylamine. The amount of proton acceptor included in the reaction can and will vary, but can be readily determined by a person of ordinary skill in the art.

In general, the volume to mass ratio of the solvent to MMB ranges from about 1:1 to about 100:1. In various embodiments, the volume to mass ratio of the solvent to MMB may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB may range from about 20:1 to about 30:1. In other exemplary embodiments, the volume to mass ratio of the solvent to MMB may range from about 10:1 to about 20:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of MMB, and a significantly increased amount of the carboxylic acid derivative compared to the amounts of each present at the beginning of the reaction. Typically, the amount of MMB remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 5 minutes to about 15 minutes. In other embodiments, the reaction may be allowed to proceed about 45 minutes to about 75 minutes. In still other embodiments, the reaction may be allowed to proceed about 36 hours to about 48 hours.

Generally, the carboxylic acid derivative is not isolated and step (b) of the process proceeds in the same reaction pot or reactor. In some embodiments, the carboxylic acid derivative may be isolated from the reaction mixture using techniques known to those of skill in the art. Non-limiting examples of suitable techniques include precipitation, extraction, evaporation, distillation, chromatography, and crystallization.

The yield of the carboxylic acid derivative can and will vary. Typically, the yield of the carboxylic acid derivative may be at least about 40%. In one embodiment, the yield of the carboxylic acid derivative may range from about 40% to about 60%. In another embodiment, the yield of the carboxylic acid derivative may range from about 60% to about 80%. In a further embodiment, the yield of the carboxylic acid derivative may range from about 80% to about 90%. In still another embodiment, the yield of the carboxylic acid derivative may be greater than about 90%, or greater than about 95%.

(iii) Step (b)—Reaction Mixture

Step (b) of the process continues with (b) contacting the carboxylic acid derivative with a compound comprising formula $R^4$—H to form a compound comprising Formula (II) or (III). The process commences with the formation of a reaction mixture comprising the carboxylic acid derivative, which is detailed above, a compound comprising the formula $R^4$—H, and optionally a solvent system.

In some embodiments, the compound comprising formula $R^4$—H may be selected from the group consisting of imidazole, benzimidazole, morpholine, piperidine, pyrrole, pyrrolidine, triazole, tetrazole, piperazine, pyridine, pyrazoloimidazole, methanol, ethanol, N,N-dimethylethanolamine, morpholinoethanol, and piperidinopropanol.

The amounts of the compound comprising formula $R^4$—H that are contacted with the carboxylic acid derivative may vary. In general, the mole to mole ratio of the carboxylic acid derivative to the compound comprising formula $R^4$—H may range from about 1:0.2 to about 1:15. In certain embodiments, the mole to mole ratio of the carboxylic acid derivative to the compound comprising formula $R^1$—H may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the carboxylic acid derivative to the compound comprising formula $R^4$—H may range from about 1:0.7 to about 1:3.

Contact with the compound comprising formula $R^4$—H generally is conducted in the presence of a solvent or solvent system. Suitable solvents are detailed above in Section II(c)(i). In exemplary embodiments, the solvent may be dichloromethane, chloroform, or combinations thereof. Additionally, a proton acceptor is generally added to facilitate the reaction. Suitable proton acceptors are detailed above in Section II(c)(i). In a specific embodiment, the proton acceptor is triethylamine. Further, peptide coupling agents may also be added to the reaction. Non-limiting examples of suitable peptide coupling agents include EDC (1-Ethyl-3-(3-dimethylaminopropyl)carbodiimide)), HOBt (Hydroxybenzotriazole), DCC (N,N'-Dicyclohexylcarbodiimide), HATU ((1-[Bis(dimethylamino)methylene]-1H-1,2,3-triazolo[4,5-b]pyridinium 3-oxid hexafluorophosphate)), HBTU (O-(Benzotriazol-1-yl)-N,N,N',N'-tetramethyluronium Hexafluorophosphate), and TBTU (O-(Benzotriazol-1-yl)-N,N,N',N'-tetramethyluronium tetrafluoroborate). In an exemplary embodiment, EDC (1-Ethyl-3-(3-dimethylaminopropyl)carbodiimide)) and HOBt (Hydroxybenzotriazole) are added to the reaction.

In general, the volume to mass ratio of the solvent to the carboxylic acid derivative ranges from about 1:1 to about 100:1. In various embodiments, the volume to mass ratio of the solvent to the carboxylic acid derivative may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the carboxylic acid derivative may range from about 20:1 to about 30:1. In another exemplary embodiment, the volume to mass ratio of the solvent to the carboxylic acid derivative may range from about 10:1 to about 20:1.

(iv) Step (b)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. In other embodiments, the reaction may be conducted at a temperature from about 0° C. to about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. Typically, the amount of the carboxylic acid derivative remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 3 hours to about 16 hours.

The yield of the compound comprising Formula (II) or (III) can and will vary. Typically, the yield of the compound comprising Formula (II) or (III) may be at least about 40%. In one embodiment, the yield of the compound comprising Formula (II) or (III) may range from about 40% to about 60%. In another embodiment, the yield of the compound comprising Formula (II) or (III) may range from about 60% to about 80%. In a further embodiment, the yield of the compound comprising Formula (II) or (III) may range from about 80% to about 90%. In still another embodiment, the yield of the compound comprising Formula (II) or (III) may be greater than about 90%, or greater than about 95%.

(d) Ester Derivatives of MMB Via Carboxylic Acids

Ester derivatives of MMB may be synthesized from the reaction of various organic carboxylic acids with MMB in the presence of EDCI (1-Ethyl-3-(3-dimethylaminopropyl) carbodiimide) in dichloromethane. The reaction may occur at about room temperature for about 8 hours to furnish the corresponding MMB ester conjugate (Scheme 6).

Scheme 6

(VI)

In one embodiment, the carboxylic acid utilized in Scheme 6 may result in the synthesis of simple and substituted indole, benzothiophene, and benzofuran carboxylate ester conjugates of MMB. For example, the carboxylic acid may be 5-methoxyindole-2-carboxylic acid, 5-chloro-indole-2-carboxylic acid, 5-fluorindole-2-carboxylic acid, indole-3-acetic acid, indole-3-acrylic acid, indomethacin, benzothiophene-2-carboxylic acid, 3-chlorobenzothiopene-2-carboxylic acid, benzofuran-2-carboxylic acid. Specifically, these organic acids may be converted into their corresponding MMB ester conjugates: BS-2-01, 2-30, 2-68, 2-32, 2-04, 2-71, 2-65, 2-64, 2-63 (below).

In another embodiment, the carboxylic acid utilized in Scheme 6 may result in the synthesis of MMB ester conjugates of various heterocyclic carboxylic acids. For example, the carboxylic acid may be 2-aminonicotinic acid, pyrazine-2-carboxylic acid, 5-methylthiophene-2-carboxylic acid, and acetic acid. Specifically, these organic acids may be converted into their corresponding MMB ester conjugates: BS-2-66, 2-67, 2-78, 2-59 (below).

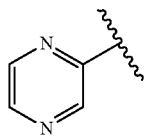

BS-2-67

In still another embodiment, the methyl esters of a carboxylic acid may be treated with aqueous sodium hydroxide (NaOH) in methanol to afford the corresponding carboxylic acid prior to conjugation with MMB. For example, the methyl esters of 5-indole carboxylic acid and 6-indole carboxylic acid may be treated with aqueous NaOH in methanol to afford the corresponding indole carboxylic acids prior to conjugation with MMB utilizing the conditions of Scheme 6 to afford the respective MMB ester conjugates (Scheme 7).

include 5-methoxyindole-2-carboxylic acid, 5-chloro-indole-2-carboxylic acid, 5-fluorindole-2-carboxylic acid, indole-3-acetic acid, indole-3-acrylic acid, indomethacin, benzothiophene-2-carboxylic acid, 3-chlorobenzothiopene-2-carboxylic acid, and benzofuran-2-carboxylic acid. In other embodiments, a carboxylic acid may be various heterocyclic carboxylic acids. Non-limiting examples of various heterocyclic carboxylic acids include 2-aminonicotinic acid, pyrazine-2-carboxylic acid, 5-methylthiophene-2-carboxylic acid, acetic acid, 5-(2-oxohexahydro-1H-thienol[3,4-d]imidazol-4-yl)pentanoic acid, and 12-(5-(2-oxohexahydro-1H-thieno[3,4-d]imidazol-4-yl)pentan-amido) dodecanoic acid.

The amounts of carboxylic acid that are contacted with MMB may vary. In general, the mole to mole ratio of MMB to carboxylic acid may range from about 1:0.2 to about 1:15. In certain embodiments, the mole to mole ratio of MMB to carboxylic acid may range from about 1:0.2 to about 1:0.7, Scheme 7: Synthesis of indole carboxylate esters of MMB

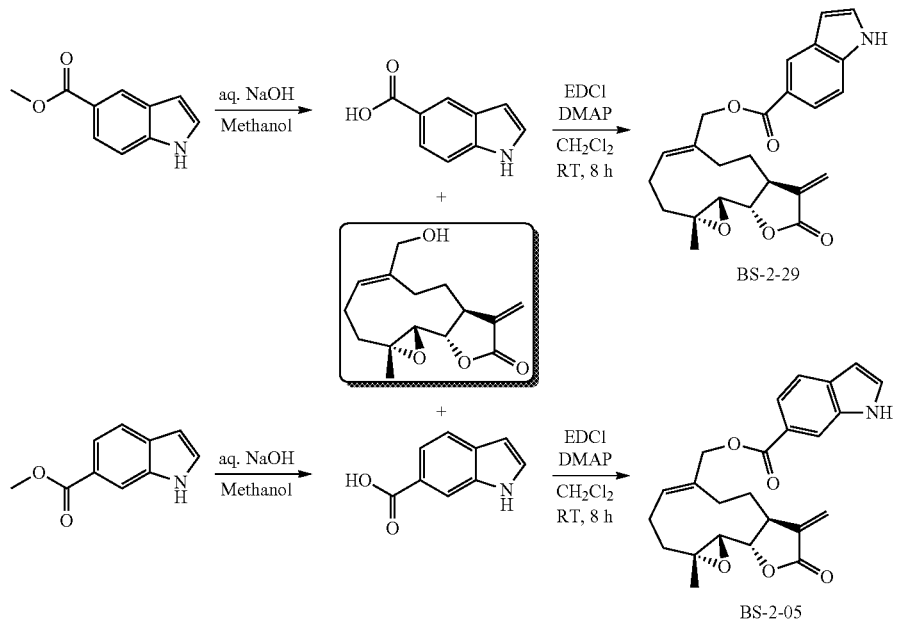

In particular, provided herein are processes for preparing a compound comprising Formula (I), (II), (IV) or (VI). The process generally comprises (a) contacting MMB with a carboxylic acid to form a compound comprising Formula (I), (II), (IV) or (VI). Optionally, prior to step (a), an ester may be converted into the corresponding carboxylic acid prior to conjugation with MMB.

(i) Step (a)—Reaction Mixture

Step (a) of the process comprises contacting MMB with a carboxylic acid to form an ester derivative of MMB. The process commences with the formation of a reaction mixture comprising MMB, a carboxylic acid, and optionally a solvent system.

The carboxylic acid may be any compound which comprises a carboxylic acid group (—COOH). In certain embodiments, a carboxylic acid may be simple and substituted indole, benzothiophene, and benzofuran carboxylic acids. Non-limiting examples of simple and substituted indole, benzothiophene, and benzofuran carboxylic acids from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB to carboxylic acid may range from about 1:0.7 to about 1:3. In an exemplary embodiment, the mole to mole ratio of MMB to carboxylic acid may be about 1:0.7.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-di methylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

Further, peptide coupling agents may also be added to the reaction. A peptide coupling agent may be used as a carboxyl activating agent for the coupling of primary amines to yield amide bonds. Non-limiting examples of suitable peptide coupling agents include EDCI (1-Ethyl-3-(3-dimethylaminopropyl)carbodiimide)), HOBt (Hydroxybenzotriazole), DCC (N,N'-Dicyclohexylcarbodiimide), HATU ((1-[Bis(dimethylamino)methylene]-1H-1,2,3-triazolo[4,5-b]pyridinium 3-oxid hexafluorophosphate)), HBTU (O-(Benzotriazol-1-yl)-N,N,N',N'-tetramethyluronium Hexafluorophosphate), and TBTU (O-(Benzotriazol-1-yl)-N,N,N',N'-tetramethyluronium tetrafluoroborate). In an exemplary embodiment, EDCI (1-Ethyl-3-(3-dimethylaminopropyl)carbodiimide)) is added to the reaction.

Additionally, a nucleophilic catalyst may be added to the reaction. A nucleophilic catalyst may be used for a variety of reactions such as esterifications with anhydrides, the Baylis-Hillman reaction, hydrosilylations, tritylation, the Steglich rearrangement, and Staudinger synthesis of β-lactams. Non-limiting examples of suitable nucleophilic catalysts include 4-Dimethylaminopyridine (DMAP) and N-Hydroxybenzotriazole (HOBt). In an exemplary embodiment DMAP is added to the reaction.

In general, the volume to mass ratio of the solvent to MMB ranges from about 1:1 to about 100:1. In various embodiments, the volume to mass ratio of the solvent to MMB may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB may range from about 20:1 to about 30:1. In other exemplary embodiments, the volume to mass ratio of the solvent to MMB may range from about 10:1 to about 20:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of MMB, and a significantly increased amount of the compound comprising Formula (I), (II), (IV) or (VI) compared to the amounts of each present at the beginning of the reaction. Typically, the amount of MMB remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 6 hours to about 12 hours. In other embodiments, the reaction may be allowed to proceed about 6 hours to about 10 hours. In still other embodiments, the reaction may be allowed to proceed about 8 hours.

The yield of the compound comprising Formula (I), (II), (IV) or (VI) can and will vary. Typically, the yield of the compound comprising Formula (I), (II), (IV) or (VI) may be at least about 40%. In one embodiment, the yield of the compound comprising Formula (I), (II), (IV) or (VI) may range from about 40% to about 60%. In another embodiment, the yield of the compound comprising Formula (I), (II), (IV) or (VI) may range from about 60% to about 80%. In a further embodiment, the yield of the compound comprising Formula (I), (II), (IV) or (VI) may range from about 80% to about 90%. In still another embodiment, the yield of the compound comprising Formula (I), (II), (IV) or (VI) may be greater than about 90%, or greater than about 95%.

(iii) Optional Step

Optionally, prior to step (a), an ester is converted into the corresponding carboxylic acid prior to conjugation with MMB. An ester may be any ester of a carboxylic acid described in Section II(d)(i) above. Methods to convert an ester to a carboxylic acid are known in the art. An aqueous acid such as $H_2SO_4$ or an aqueous base such as NaOH and heat may be used for the conversion. In certain embodiments, this conversion may occur via reaction of a methyl ester with aqueous sodium hydroxide (NaOH) in methanol to afford the corresponding carboxylic acid. In a specific embodiment, the methyl esters of 5-indole carboxylic acid and 6-indole carboxylic acid may be treated with aqueous NaOH in methanol to afford the corresponding indole carboxylic acid.

(e) Ester Derivatives of MMB Via Chlorides

Ester derivatives of MMB may be synthesized from the reaction of various acyl chlorides with MMB in the presence of triethylamine and dichloromethane. The reaction may occur at about room temperature for about 1-18 hours to furnish the corresponding MMB ester conjugate (Scheme 8).

Scheme 8

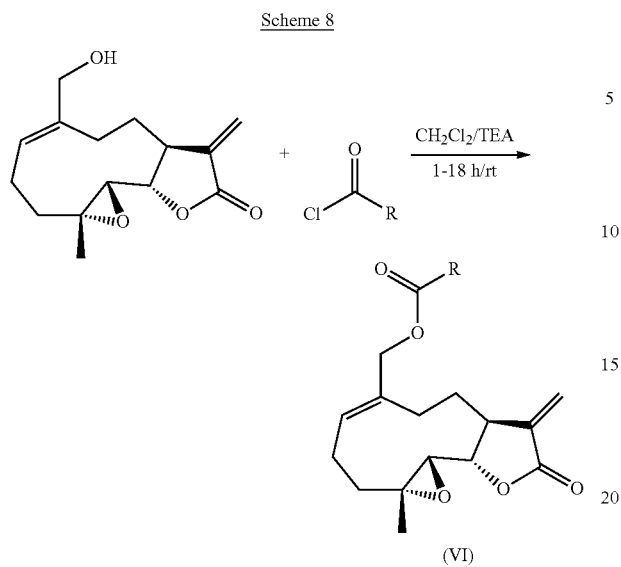

(VI)

In one embodiment, ester conjugates may be synthesized by the reaction of MMB with substituted benzoyl and naphthoyl chlorides in the presence of triethylamine as base and dichloromethane as solvent in ambient temperature for 6-18 h. Specifically, these chlorides were converted into their corresponding MMB ester conjugates (below).

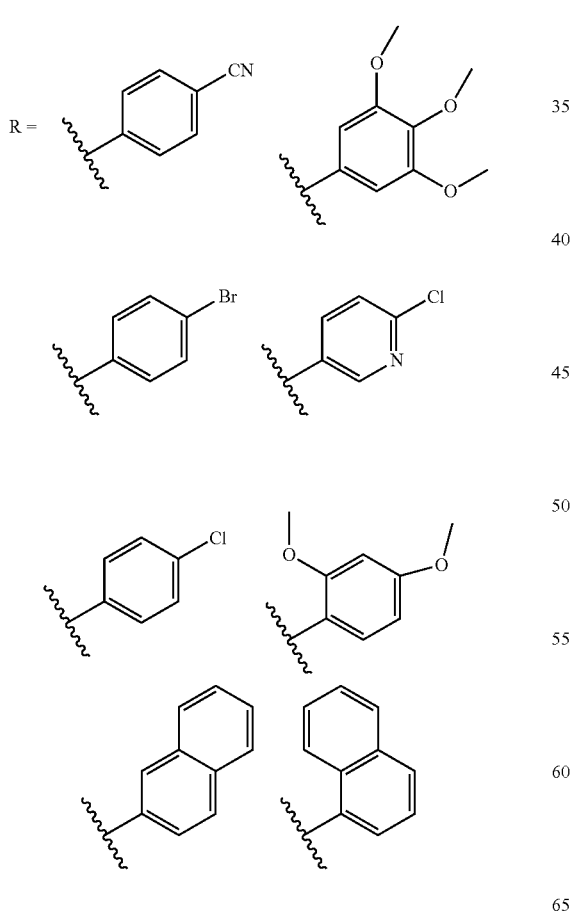

In an exemplary embodiment, MMB esters of the invention may be:

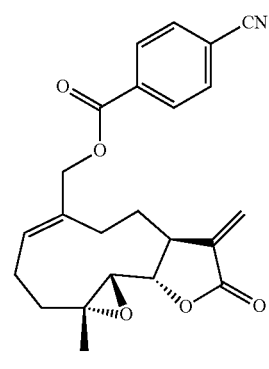

JVM 3-39

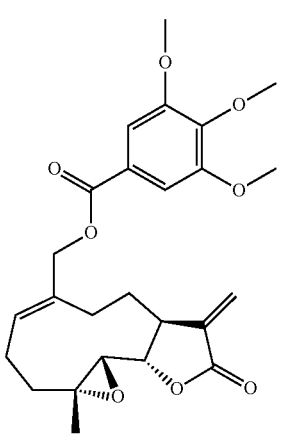

JVM 3-22

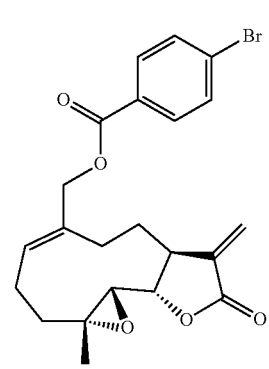

JVM 3-30

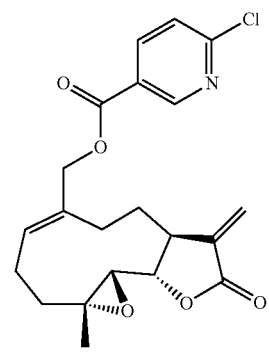

JVM 3-40

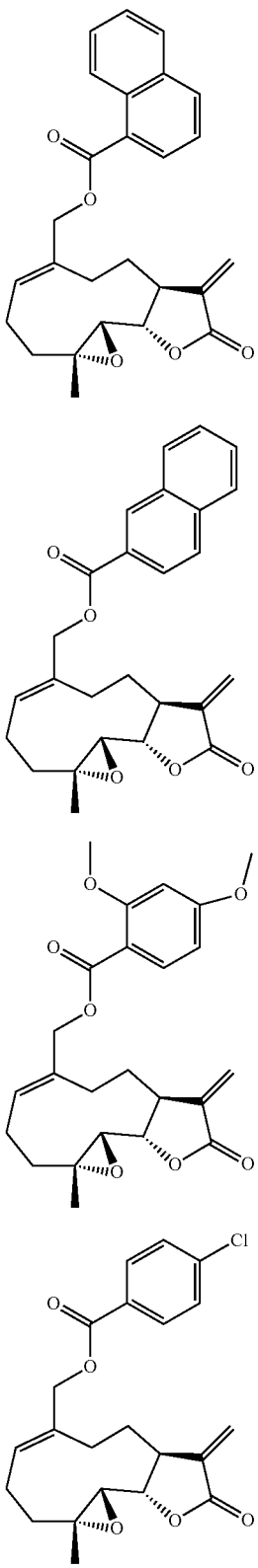

JVM 3-38

JVM 3-36

JVM 3-44

JVM 3-41

In another embodiment, analogues of indole carboxylate—MMB ester conjugates may be prepared by the reaction of MMB with a variety of substituted 2-(1H-indol-3-yl)-2-oxoacetyl chlorides in the presence of triethylamine at about room temperature for about 1 to 5 h. The substituted 2-(1H-indol-3-yl)-2-oxoacetyl chlorides may be prepared by the reaction of the appropriate indole with oxalyl chloride in diethyl ether at about 0° C. to about room temperature for about 1 h (Scheme 9).

Scheme 9: Synthesis of 2-(1H-indol-3-yl)-2-oxoacetyl ester conjugates of MMB

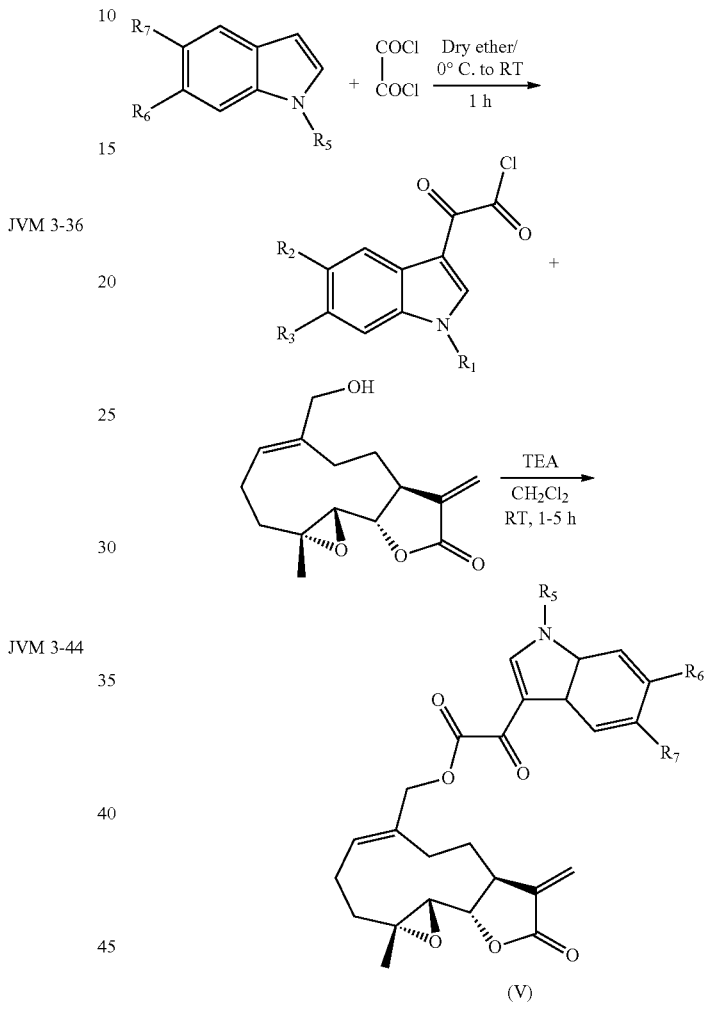

(V)

In particular, provided herein are processes for preparing a compound comprising Formula (I), (II), (V) or (VI). The process generally comprises (a) contacting MMB with an acyl chloride to form a compound comprising Formula (I), (II), (V) or (VI). Optionally, prior to step (a), a compound may be converted into the corresponding acyl chloride prior to conjugation with MMB.

(i) Step (a)—Reaction Mixture

Step (a) of the process comprises contacting MMB with an acyl chloride to form an ester derivative of MMB. The process commences with the formation of a reaction mixture comprising MMB, an acyl chloride, and optionally a solvent system.

The acyl chloride may be any compound which comprises an acyl chloride group (—COCl). The compound comprising an acyl chloride may comprise an alkyl chain. The alkyl chain may be linear, branched or contain an aromatic ring.

The alkyl chain may be a hydrocarbyl alkyl chain or a substituted hydrocarbyl alkyl chain. The alkyl chain may be a length of 1 to 10 atoms. For example, the alkyl chain may be 1, 2, 3, 4, 5, 6, 7, 8, 9 or 10 atoms in length. In certain embodiments, an acyl chloride may be a substituted benzoyl or napthoyl chloride. In other embodiments, an acyl chloride may be a variety of substituted 2-(1H-indol-3-yl)-2-oxoacetyl chlorides.

The amounts of acyl chloride that are contacted with MMB may vary. In general, the mole to mole ratio of MMB to acyl chloride may range from about 1:0.2 to about 1:15. In certain embodiments, the mole to mole ratio of MMB to acyl chloride may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB to acyl chloride may range from about 1:0.7 to about 1:3. In an exemplary embodiment, the mole to mole ratio of MMB to acyl chloride may be about 1:0.7.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-di methylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In a specific embodiment, the proton acceptor is triethylamine. The amount of proton acceptor included in the reaction can and will vary, but can be readily determined by a person of ordinary skill in the art.

In general, the volume to mass ratio of the solvent to MMB ranges from about 1:1 to about 100:1. In various embodiments, the volume to mass ratio of the solvent to MMB may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB may range from about 20:1 to about 30:1. In other exemplary embodiments, the volume to mass ratio of the solvent to MMB may range from about 10:1 to about 20:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of MMB, and a significantly increased amount of the compound comprising Formula (I), (II), (V) or (VI) compared to the amounts of each present at the beginning of the reaction. Typically, the amount of MMB remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 1 hour to about 18 hours. In other embodiments, the reaction may be allowed to proceed about 1 hour to about 5 hours. In still other embodiments, the reaction may be allowed to proceed about 6 hours to about 18 hours.

The yield of the compound comprising Formula (I), (II), (V) or (VI) can and will vary. Typically, the yield of the compound comprising Formula (I), (II), (V) or (VI) may be at least about 40%. In one embodiment, the yield of the compound comprising Formula (I), (II), (V) or (VI) may range from about 40% to about 60%. In another embodiment, the yield of the compound comprising Formula (I), (II), (V) or (VI) may range from about 60% to about 80%. In a further embodiment, the yield of the compound comprising Formula (I), (II), (V) or (VI) may range from about 80% to about 90%. In still another embodiment, the yield of the compound comprising Formula (I), (II), (V) or (VI) may be greater than about 90%, or greater than about 95%.

(iii) Optional Step

Optionally, prior to step (a), a compound is converted into the corresponding acyl chloride prior to conjugation with MMB. A compound may be the parent of an acyl chloride described in Section II(e)(i) above. A compound may be converted to an acyl chloride via reaction of the compound with oxalyl chloride (COCl)$_2$ in the presence of diethyl ether. The reaction may be carried out at about 0° C. to about 25° C. for about 1 hour. In a specific embodiment, various indoles may be reacted with oxalyl chloride in the presence of diethyl ether.

(f) Amide Derivatives of MMB

Amide derivatives of MMB may be synthesized from the reaction of various heterocyclic amines with melampomagnolic acid in the presence of EDCI (1-ethyl-3-(3-dimethylaminopropyl)carbodiimide), hydroxybenzotriazole (HOBt) and triethylamine. The reaction may occur at about room temperature for about 3 to 8 hours to furnish the corresponding MMB amide conjugate (Scheme 10).

Scheme 10: Synthesis of amide conjugates of MMB

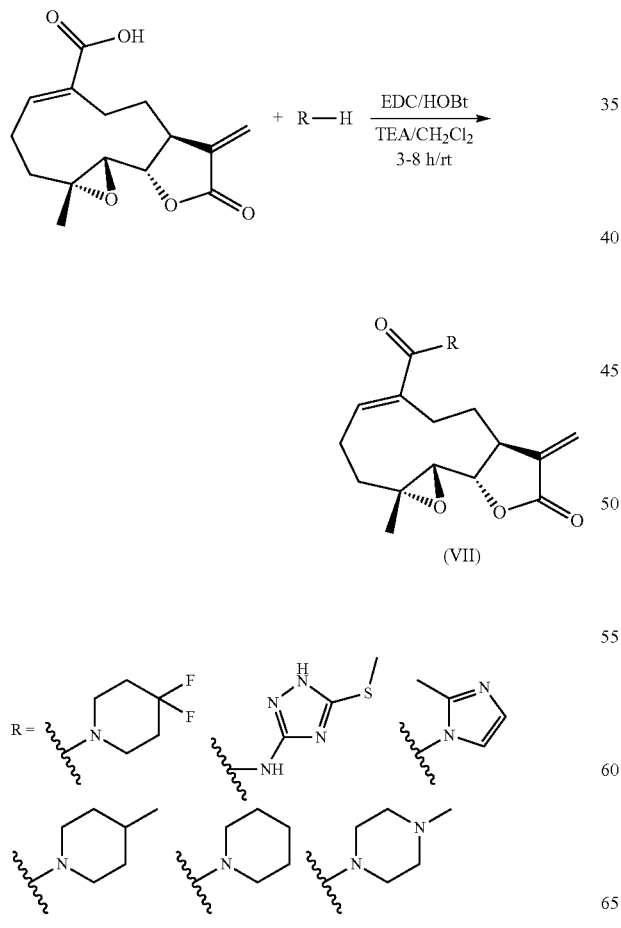

In an exemplary embodiment, MMB amides of the invention may be:

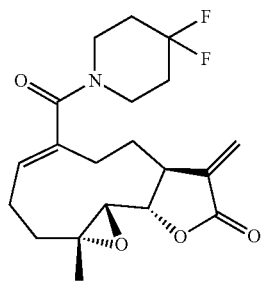

JVM 3-50

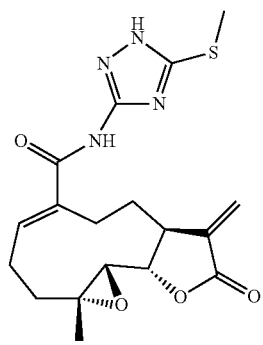

JVM 3-53

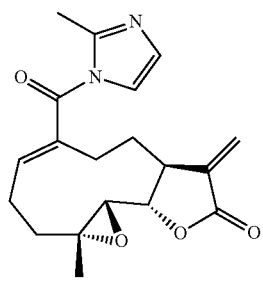

JVM 3-57

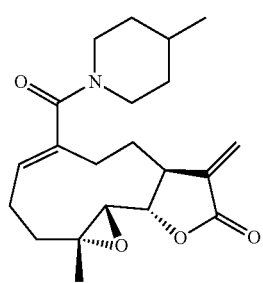

JVM 3-51

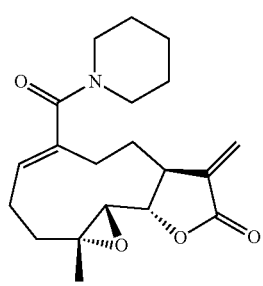

JVM 3-52

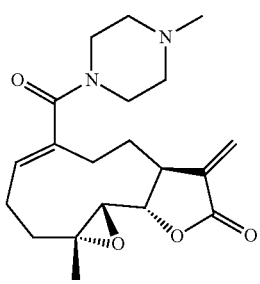

JVM 3-46

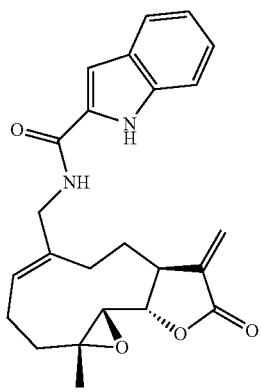

JVM 4-19

Alternatively, amide derivatives of MMB may be synthesized from the reaction of various aromatic or heteroaromatic carboxylic acids with an amine derivative of MMB in the presence of EDCI (1-ethyl-3-(3-dimethylaminopropyl) carbodiimide), hydroxybenzotriazole (HOBt) and triethylamine. The reaction may occur at about room temperature for about 3 to 15 hours to furnish the corresponding MMB amide conjugate (Scheme 11).

Scheme 11: Synthesis of aromatic and heteroaromatic amide derivatives of MMB

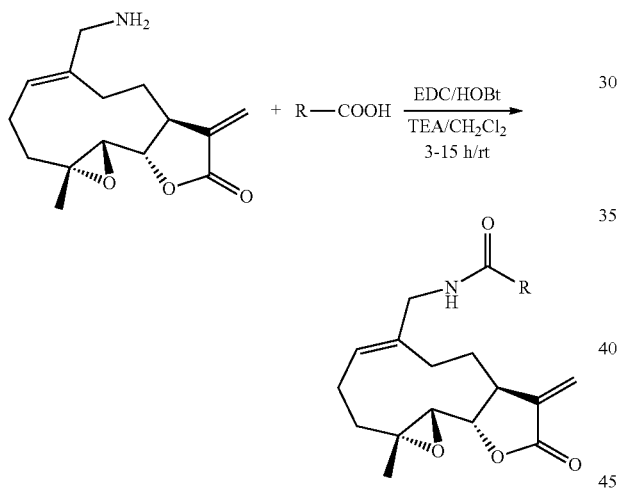

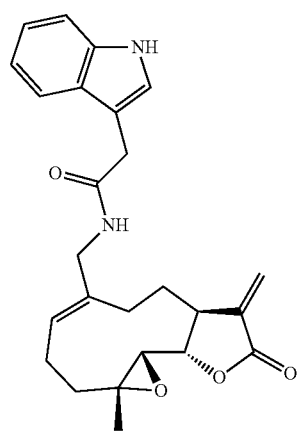

JVM 4-14

In another exemplary embodiment, MMB amides of the invention may be:

JVM 4-17

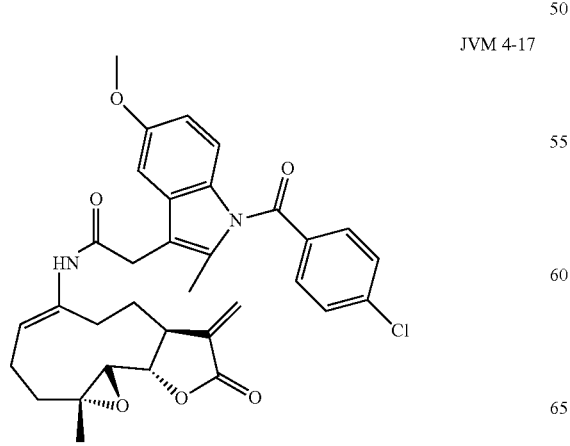

JVM 4-33

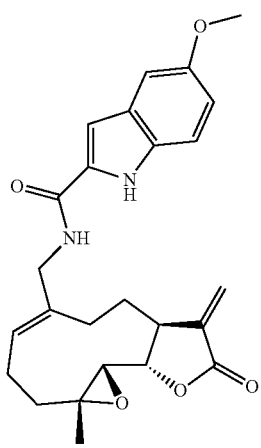

JVM 4-28

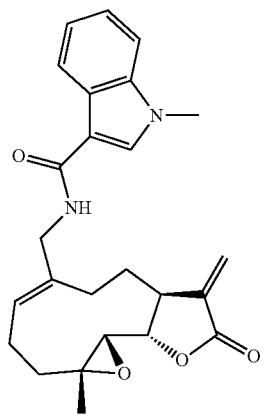

JVM 4-36

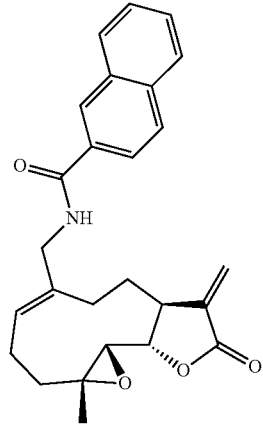

JVM 4-32

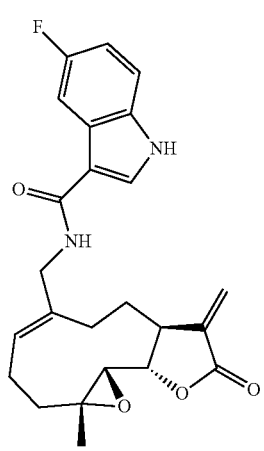

JVM 4-38

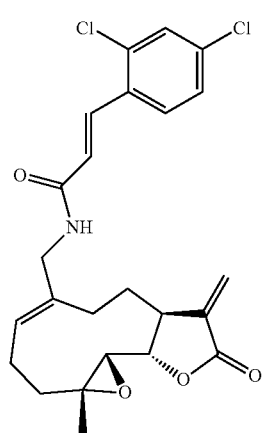

JVM 4-34

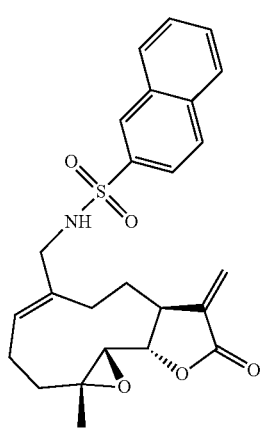

JVM 4-37

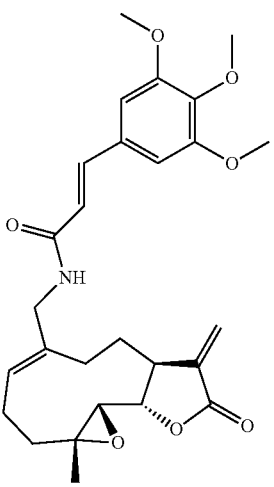

In particular, provided herein are processes for preparing a compound comprising Formula (I) or (VII). The process generally comprises (a) contacting melampomagnolic acid with a heterocyclic amine to form a compound comprising Formula (I) or (VII).

Also, in particular, provided herein are processes for preparing a compound comprising Formula (I) or (VIII). The process generally comprises (a) contacting an amine derivative of MMB with a carboxylic acid to form a compound comprising Formula (I) or (VIII).

(i) Step (a)—Reaction Mixture

Step (a) of the process comprises contacting melampomagnolic acid with a heterocyclic amine to form an amide derivative of MMB. The process commences with the formation of a reaction mixture comprising melampomagnolic acid, a heterocyclic amine, and optionally a solvent system. Alternatively, step (a) of the process comprises contacting an amine derivative of MMB with a carboxylic acid to form an amide derivative of MMB. The process commences with the formation of a reaction mixture comprising an amine derivative of MMB, a carboxylic acid, and optionally a solvent system.

The heterocyclic amine may be any compound comprising a heterocycle and an amine group. The heterocyle may be an optionally substituted, fully saturated or unsaturated, monocyclic or bicyclic, aromatic or non-aromatic group having at least one heteroatom in at least one ring, and preferably 5 or 6 atoms in each ring. The heterocycle preferably has 1 or 2 oxygen atoms and/or 1 to 4 nitrogen atoms in the ring. Non-limiting examples of suitable heterocyclic amines include imidazole, benzimidazole, morpholine, piperidine, pyrrole, pyrrolidine, triazole, tetrazole, piperazine, pyridine, pyrazoloimidazole, methanol, ethanol, N,N-dimethylethanolamine, morpholinoethanol, and piperidinopropanol.

The carboxylic acid may be any compound which comprises a carboxylic acid group (—COOH). In certain embodiments, the carboxylic acid may be an aromatic or heteroaromatic carboxylic acid. The aromatic or heteroaromatic ring may be an optionally substituted monocyclic, bicyclic, or tricyclic group containing from 5 to 14 atoms in the ring portion. For example, the aromatic or heteroaromatic ring may be a phenyl, biphenyl, naphthyl, substituted phenyl, substituted biphenyl, or substituted naphthyl. In other embodiments, a carboxylic acid may be simple and substituted indole, benzothiophene, and benzofuran carboxylic acids. Non-limiting examples of simple and substituted indole, benzothiophene, and benzofuran carboxylic acids include 5-methoxyindole-2-carboxylic acid, 5-chloro-indole-2-carboxylic acid, 5-fluorindole-2-carboxylic acid, indole-3-acetic acid, indole-3-acrylic acid, indomethacin, benzothiophene-2-carboxylic acid, 3-chlorobenzothiopene-2-carboxylic acid, and benzofuran-2-carboxylic acid. In other embodiments, a carboxylic acid may be various heterocyclic carboxylic acids. Non-limiting examples of various heterocyclic carboxylic acids include 2-aminonicotinic acid, pyrazine-2-carboxylic acid, 5-methylthiophene-2-carboxylic acid, acetic acid, 5-(2-oxohexahydro-1H-thienol[3,4-d]imidazol-4-yl)pentanoic acid, and 12-(5-(2-oxohexahydro-1H-thieno[3,4-d]imidazol-4-yl)pentanamido) dodecanoic acid.

The amounts of heterocyclic amine or carboxylic acid that are contacted with melampomagnolic acid or an amine derivative of MMB, respectively, may vary. In general, the mole to mole ratio of melampomagnolic acid to heterocyclic amine or amine derivative of MMB to carboxylic acid may range from about 1:0.2 to about 1:15. In certain embodiments, the mole to mole ratio of melampomagnolic acid to heterocyclic amine or amine derivative of MMB to carboxylic acid may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of melampomagnolic acid to heterocyclic amine or amine derivative of MMB to carboxylic acid may range from about 1:0.2 to about 1:0.7. In an exemplary embodiment, the mole to mole ratio of melampomagnolic acid to heterocyclic amine or amine derivative of MMB to carboxylic acid may be about 1:0.5.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-di methylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In a specific embodiment, the proton acceptor is triethylamine. The amount of proton acceptor included in the reaction can and will vary, but can be readily determined by a person of ordinary skill in the art.

Further, peptide coupling agents may also be added to the reaction. A peptide coupling agent may be used as a carboxyl activating agent for the coupling of primary amines to yield amide bonds. Non-limiting examples of suitable peptide coupling agents include EDCI (1-Ethyl-3-(3-dimethylaminopropyl)carbodiimide)), HOBt (Hydroxybenzotriazole), DCC (N,N'-Dicyclohexylcarbodiimide), HATU ((1-[Bis(dimethylamino)methylene]-1H-1,2,3-triazolo[4,5-b]pyridinium 3-oxid hexafluorophosphate)), HBTU (O-(Benzotriazol-1-yl)-N,N,N',N'-tetramethyluronium Hexafluorophosphate), and TBTU (O-(Benzotriazol-1-yl)-N,N,N',N'-tetramethyluronium tetrafluoroborate). In an exemplary embodiment, EDCI (1-Ethyl-3-(3-dimethylaminopropyl)carbodiimide)) and HOBt (Hydroxybenzotriazole) are added to the reaction.

In general, the volume to mass ratio of the solvent to melampomagnolic acid or amine derivative of MMB ranges from about 1:1 to about 100:1. In various embodiments, the volume to mass ratio of the solvent to melampomagnolic acid or amine derivative of MMB may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to melampomagnolic acid or amine derivative of MMB may range from about 20:1 to about 30:1. In other exemplary embodiments, the volume to mass ratio of the solvent to melampomagnolic acid or amine derivative of MMB may range from about 10:1 to about 20:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of melampomagnolic acid, and a significantly increased amount of the compound comprising Formula (I) or (VII) compared to the amounts of each present at the beginning of the reaction. Typically, the amount of melampomagnolic acid remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 3 hours to about 15 hours. In other embodiments, the reaction may be allowed to proceed about 3 hours to about 8 hours.

The yield of the compound comprising Formula (I), (VII) or (VIII) can and will vary. Typically, the yield of the compound comprising Formula (I), (VII) or (VIII) may be at least about 40%. In one embodiment, the yield of the compound comprising Formula (I), (VII) or (VIII) may range from about 40% to about 60%. In another embodiment, the yield of the compound comprising Formula (I), (VII) or (VIII) may range from about 60% to about 80%. In a further embodiment, the yield of the compound comprising Formula (I), (VII) or (VIII) may range from about 80% to about 90%. In still another embodiment, the yield of the compound comprising Formula (I), (VII) or (VIII) may be greater than about 90%, or greater than about 95%.

III. Compositions

The present disclosure also provides pharmaceutical compositions. The pharmaceutical composition comprises a compound comprising Formula (I), (II), (III), (IV), (V), (VI), (VII) or (VIII) which is detailed above in Section I, as an active ingredient and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as ethylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the compound of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of the invention may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the compound of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, a composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

IV. Methods for Inhibiting Cancer Cell Growth

A further aspect of the present disclosure provides a method for inhibiting growth of a cancer cell. Cancer cell growth includes cell proliferation and cell metastasis. The method comprises contacting the cancer cell with an effective amount of a compound comprising Formula (I), (II), (III), (IV), (V), (VI), (VII) or (VIII), or a pharmaceutically acceptable salt thereof, wherein the amount is effective to inhibit growth of the cancer cell. Compounds comprising Formula (I), (II), (III), (IV), (V), (VI), (VII) or (VIII) are detailed above in Section I. In some embodiments, the compound comprising Formula (I), (II), (III), (IV), (V), (VI), (VII) or (VIII) is used as part of a composition, examples of which are detailed above in Section III.

(a) Contacting the Cell

In some embodiments, the cancer cell may be in vitro. The cancer cell may be an established, commercially-available cancer cell line (e.g., American Type Culture Collection (ATCC), Manassas, Va.). The cancer cell line may be derived from a blood cancer or a solid tumor. The cancer cell line may be a human cell line or a mammalian cell line. In a specific embodiment, the cancer cell line may be derived from a blood cancer. In one exemplary embodiment, the cancer cell line may be derived from a leukemic cell. The leukemic cell may be an acute myeloid leukemia cell, a chronic myeloid leukemia cell, an acute lymphocytic leukemia cell, a chronic lymphocytic leukemia cell, a cutaneous T cell leukemia, or another type of leukemia cell. In some embodiments, the cancer cell line may be a leukemia cell line such as CCRF-CEM, HL-60(TB), K-562, MOLT-4, RPMI-8226, or SR. In a specific embodiment, the cancer cell line may be the leukemia cell line M9 ENL. In other embodiments, the cancer cell line may be a hematopoietic or lymphoid cell line. Non-limiting examples of hematopoietic or lymphoid cell lines include 380, 697, A3-KAW, A3/KAW, A4-Fuk, A4/Fuk, ALL-PO, ALL-SIL, AML-193, AMO-1, ARH-77, ATN-1, BALL-1, BC-3, BCP-1, BDCM, BE-13, BL-41, BL-70, BV-173, C8166, CA46, CCRF-CEM, CI-1, CMK, CMK-11-5, CMK-86, CML-T1, COLO 775, COLO-677, CTB-1, CTV-1, Daudi, DB, DEL, DG-75, DND-41, DOHH-2, EB1, EB2, EHEB, EJM, EM-2, EOL-1, EoL-1-cell, F-36P, GA-10, GA-10-Clone-4, GDM-1, GR-ST, GRANTA-519, H9, HAL-01, HD-MY-Z, HDLM-2, HEL, HEL 92.1.7, HH, HL-60, HPB-ALL, Hs 604.T, Hs 611.T, Hs 616.T, Hs 751.T, HT, HTK-, HuNS1, HuT 102, HuT 78, IM-9, J-RT3-T3-5, JeKo-1, JiyoyeP-2003, JJN-3, JK-1, JM1, JURKAT, JURL-MK1, JVM-2, JVM-3, K-562, K052, KARPAS-299, KARPAS-422, KARPAS-45, KARPAS-620, KASUMI-1, KASUMI-2, Kasumi-6, KCL-22, KE-37, KE-97, KG-1, KHM-1B, Ki-JK, KM-H2, KMM-1, KMOE-2, KMS-11, KMS-12-BM, KMS-12-PE, KMS-18, KMS-20, KMS-21BM, KMS-26, KMS-27, KMS-28BM, KMS-34, K052, KOPN-8, KU812, KY821, KYO-1, L-1236, L-363, L-428, L-540, LAMA-84, LC4-1, Loucy, LOUCY, LP-1, M-07e, MC-CAR, MC116, ME-1, MEC-1, MEC-2, MEG-01, MHH-CALL-2, MHH-CALL-3, MHH-CALL-4, MHH-PREB-1, Mino, MJ, ML-2, MLMA, MM1-S, MN-60, MOLM-13, MOLM-16, MOLM-6, MOLP-2, MOLP-8, MOLT-13, MOLT-16, MOLT-4, MONO-MAC-1, MONO-MAC-6, MOTN-1, MUTZ-1, MUTZ-3, MUTZ-5, MV-4-11, NALM-1, NALM-19, NALM-6, NAMALWA, NB-4, NCI-H929, NCO2, NKM-1, NOMO-1, NU-DHL-1, NU-DUL-1, OCI-AML2, OCI-AML3, OCI-AML5, OCI-LY-19, OCI-LY10, OCI-LY3, OCI-M1, OPM-2, P12-ICHIKAWA, P30-OHK, P31-FUJ, P31/FUJ, P3HR-1, PCM6, PEER, PF-382, Pfeiffer, PL-21, Raji, Ramos-2G6-4C10, RCH-ACV, REC-1, Reh, REH, RI-1, RL, RPMI 8226, RPMI-8226, RPMI-8402, RS4-11, "RS4;11", SEM, Set-2, SIG-M5, SK-MM-2, SKM-1, SR, SR-786, ST486, SU-DHL-1, SU-DHL-10, SU-DHL-4, SU-DHL-5, SU-DHL-6, SU-DHL-8, SUP-B15, SUP-B8, SUP-HD1, SUP-M2, SUP-T1, SUP-T11, TALL-1, TF-1, THP-1, TO 175.T, Toledo, TUR, U-266, U-698-M, U-937, U266B1, UT-7, WSU-DLCL2, and WSU-NHL.

In another exemplary embodiment, the cancer cell line may be derived from a solid tumor cell. The solid tumor cell may be a non-small cell lung cancer, colon cancer, CNS cancer, melanoma cancer, ovarian cancer, renal cancer, prostate cancer, breast cancer, or another type of solid tumor cell. In some embodiments, the cancer cell line may be a non-small cell lung cancer cell line such as A549/ATCC, HOP-92, NCI-H226, NCI-H23, NCI-H322M, NCI-H460, or NCI-H522. In other embodiments, the cancer cell line may be a colon cancer cell line such as COLO 205, HCC-2998, HCT-116, HCT-15, HT29, KM12 or SW-620. In different embodiments, the cancer cell line may be a CNS cancer cell line such as SF-268, SF-295, SF-539, SNB-19, SNB-75 or U251. In some other embodiments, the cancer cell line may be a melanoma cell line such as LOX IMVI, MALME-3M, M14, MDA-MB-435, SK-MEL-2, SK-MEL-28, SK-MEL-5, UACC-257, or UACC-62. In still other embodiments, the cancer cell line may be an ovarian cancer cell line such as OVCAR-3, OVCAR-4, OVCAR-5, OVCAR-8, NCI/ADR-RES, IGROV1 or SK-OV-3. In some different embodiments, the cancer cell line may be a renal cancer cell line such as 786-0, A498, ACHN, CAKI-1, RXF 393, SN12C, TK-10, or UO-31. In other embodiments, the cancer cell line may be a prostate cancer cell line such as PC-3 or DU-145. In some embodiments, the cancer cell line may be a breast cancer cell line such as MCF7, MDA-BM-231/ATCC, HS 578T, BT-549, T-47D, or MDA-MB-468.

In other embodiments, the cancer cell may be in vivo; i.e., the cell may be disposed in a subject. In such embodiments, the cancer cell is contacted with the compound comprising Formula (I), (II), (III), (IV), (V), (VI), (VII) or (VIII) by administering the compound comprising Formula (I), (II), (III), (IV), (V), (VI), (VII) or (VIII) to the subject. In some embodiments, the subject may be a human. In other embodiments, the subject may be a non-human animal. Non-limiting examples of non-human animals include companion animals (e.g., cats, dogs, horses, rabbits, gerbils), agricultural animals (e.g., cows, pigs, sheep, goats, fowl), research animals (e.g., rats, mice, rabbits, primates), and zoo animals (e.g., lions, tiger, elephants, and the like).

The cancer cell disposed in the subject may be a blood cancer cell (e.g., leukemia, lymphoma, myeloma) or a solid tumor cancer cell. The cancer may be primary or metastatic; early stage or late stage; and/or the tumor may be malignant or benign. Non-limiting cancers include bladder cancer, bone cancer, brain cancer, breast cancer, central nervous system cancer, cervical cancer, colon cancer, colorectal cancer, duodenal cancer, endometrial cancer, esophageal cancer, eye cancer, gallbladder cancer, germ cell cancer, kidney cancer, larynx cancer, leukemia, liver cancer, lymphoma, lung cancer, melanoma, mouth/throat cancer, ovarian cancer, pancreatic cancer, prostate cancer, skin cancer, testicular cancer, thyroid cancer, vaginal cancer, and drug resistant cancers. In one exemplary embodiment, the cancer cell may be a leukemia. The leukemia may be an acute lymphocytic (lymphoblastic) leukemia, a chronic lymphocytic leukemia, an acute myeloid leukemia, a chronic myeloid leukemia, a hairy cell leukemia, a T-cell prolymphocytic leukemia, a large granular lymphocytic leukemia, or an adult T-cell leukemia. In another exemplary embodiment, the cancer cell may be a solid tumor cancer cell selected from the group consisting of non-small cell lung cancer, colon cancer, CNS cancer, melanoma cancer, ovarian cancer, renal cancer, prostate cancer and breast cancer.

The compound comprising Formula (I), (II), (III), (IV), (V), (VI), (VII) or (VIII) may be administered to the subject orally (as a solid or a liquid), parenterally (which includes intramuscular, intravenous, intradermal, intraperitoneal, and subcutaneous), or topically (which includes transmucosal and transdermal). An effective amount of the compound can be determined by a skilled practitioner in view of desired dosages and potential side effects of the compound.

The compound comprising Formula (I), (II), (III), (IV), (V), (VI), (VII) or (VIII) may be administered once or administered repeatedly to the subject. Repeated administrations may be at regular intervals of 2 hours, 6 hours, 12 hours, 24 hours, 2 days, 5 days, 7 days, 30 days, and so forth.

(b) Inhibiting Cancer Cell Growth

Following contact with an effective amount of the compound comprising Formula (I), (II), (III), (IV), (V), (VI), (VII) or (VIII) growth of the cancer cell is inhibited. Cell growth or proliferation can be measured in cells grown in vitro using standard cell viability or cell cytotoxicity assays (e.g., based on DNA content, cell permeability, etc.) in combination with cell counting methods (e.g., flow cytometry, optical density). Cell growth or proliferation can be measured in vivo using imaging procedures and/or molecular diagnostic indicators.

In an embodiment, contact with an effective amount of the compound comprising Formula (I), (II), (III), (IV), (V), (VI), (VII) or (VIII) selectively inhibits growth of cancer cells. As such, a compound comprising Formula (I), (II), (III), (IV), (V), (VI), (VII) or (VIII) does not appreciably kill non-cancer cells at the same concentration. Accordingly, more than 50% of non-cancer cells remain viable following contact with a compound comprising Formula (I), (II), (III), (IV), (V), (VI), (VII) or (VIII) at the same concentration. For example about 50%, about 55%, about 60%, about 65%, about 70%, about 75%, about 80%, about 85%, about 90%, about 95% or about 100% of non-cancer cells remain viable following contact with a compound comprising Formula (I), (II), (III), (IV), (V), (VI), (VII) or (VIII) at the same concentration. Or, 50%, 55%, 60%, 65%, 70%, 75%, 80%, 85%, 90%, 95% or 100% of non-cancer cells remain viable following contact with a compound comprising Formula (I), (II), (III), (IV), (V), (VI), (VII) or (VIII) at the same concentration.

In various embodiments, cancer cell growth may be inhibited about 0.5-fold, about 1-fold, about 2-fold, about 3-fold, about 4-fold, about 5-fold, about 8-fold, about 10-fold, or more than 10-fold relative to a reference value. In various other embodiments, cancer cell growth may be inhibited 0.5-fold, 1-fold, 2-fold, 3-fold, 4-fold, 5-fold, 8-fold, 10-fold, or more than 10-fold relative to a reference value. In other embodiments, cancer cell growth may be inhibited to such a degree that the cell undergoes cell death (via apoptosis or necrosis). Any suitable reference value known in the art may be used. For example, a suitable reference value may be cancer cell growth in a sample that has not been contacted with a compound comprising Formula (I), (II), (III), (IV), (V), (VI), (VII) or (VIII). In another example, a suitable reference value may be the baseline growth rate of the cells as determined by methods known in the art. In another example, a suitable reference value may be a measurement of the number of cancer cells in a reference sample obtained from the same subject. For example, when monitoring the effectiveness of a therapy or efficacy of a compound comprising Formula (I), (II), (III), (IV), (V), (VI), (VII) or (VIII), a reference sample may be a sample obtained from a subject before therapy or administration of the compound comprising Formula (I), (II), (III), (IV), (V), (VI), (VII) or (VIII) began.

(c) Optional Contact

In certain embodiments, the method may further comprise contacting the cell with at least one chemotherapeutic agent and/or a radiotherapeutic agent. The chemotherapeutic agent and/or radiotherapeutic agent may be administered concurrently or sequentially with the compound comprising Formula (I), (II), (III), (IV), (V), (VI), (VII) or (VIII).

The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, or a combination thereof. Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lomustine (CCNU), mechlorethamine, mechlorethamine oxide hydrochloride, melphalan, meturedopa, nimustine, novembichin, phenesterine, piposulfan, prednimustine, ranimustine; temozolomide, thiotepa, triethylenemelamine, trietylenephosphoramide, triethylenethiophosphaoramide, tri methylolomelamine, trofosfamide, uracil mustard and uredopa. Suitable anti-metabolites include, but are not limited to aminopterin, ancitabine, azacitidine, 6-azauridine, capecitabine, carmofur (1-hexylcarbomoyl-5-fluorouracil), cladribine, cytarabine or cytosine arabinoside (Ara-C), dideoxyuridine, denopterin, doxifluridine, enocitabine, floxuridine, fludarabine, 5-fluorouracil, gemcetabine, hydroxyurea, leucovorin (folinic acid), 6-mercaptopurine, methotrexate, pemetrexed, pteropterin, thiamiprine, trimetrexate, and thioguanine. Non-limiting examples of suitable anti-tumor antibiotics include aclacinomysin, actinomycins, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, streptonigrin, streptozocin, tubercidin, valrubicin, ubenimex, zinostatin, and zorubicin. Non-limiting examples of suitable anti-cytoskeletal agents include colchicines, docetaxel, macromycin, paclitaxel, vinblastine, vincristine, vindesine, and vinorelbine. Suitable topoisomerase inhibitors include, but are not limited to, amsacrine, etoposide (VP-16), irinotecan, mitoxantrone, RFS 2000, teniposide, and topotecan. Non-limiting examples of suitable anti-hormonal agents such as aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane. Examples of targeted therapeutic agents include, without limit, monoclonal antibodies such as alemtuzumab, epratuzumab, gemtuzumab, ibritumomab tiuxetan, rituximab, tositumomab, and trastuzumab; protein kinase inhibitors such as bevacizumab, cetuximab, dasatinib, erlotinib, gefitinib, imatinib, lapatinib, mubritinib, nilotinib, panitumumab, pazopanib, sorafenib, sunitinib, and vandetanib; angiogeneisis inhibitors such as angiostatin, endostatin, bevacizumab, genistein, interferon alpha, interleukin-2, interleukin-12, pazopanib, pegaptanib, ranibizumab, rapamycin, thalidomide; and growth inhibitory polypeptides such as erythropoietin, interleukins (e.g., IL-1, IL-2, IL-3, IL-6), leukemia inhibitory factor, interferons, thrombopoietin, TNF-α, CD30 ligand, 4-1BB ligand, and Apo-1 ligand. Also included are pharmaceutically acceptable salts, acids, or derivatives of any of the above listed agents. The mode of administration of the chemotherapeutic agent can and will vary depending upon the agent and the type of cancer. A skilled practitioner will be able to determine the appropriate dose of the chemotherapeutic agent.

The radiotherapeutic agent may include a radioisotope. Suitable radioisotopes include, without limit, Iodine-131, Iodine-125, Iodine-124, Lutecium-177, Phosphorous-132, Rhenium-186, Strontium-89, Yttrium-90, Iridium-192, and Samarium-153. Alternatively, the radiotherapeutic agent may include a high Z-element chosen from gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium. The appropriate dose of the radiotherapeutic agent may be determined by a skilled practitioner.

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "aliphatic" as used herein alone or as part of another group denotes an optionally substituted straight chain, branched chain or non-aromatic ring (alicyclic). These aliphatic compounds may be saturated (alkanes) or unsaturated (alkenes or alkynes). Besides hydrogen, other elements can be bound to the carbon chain. By way of non-limiting example: oxygen, nitrogen, sulfur and chlorine. Non limiting examples of an aliphatic group may be methane, ethyne, ethane, ethane, propyne, propene, propane, 1,2-butadiene, 1-butyne, butane, butane, cyclohexene, n-pentane, cycloheptane, methylcyclohexane, cubane, nonane, dicyclopentadiene, phellandrene, α-terpinene, limonene, undecane, squalene and polyethylene.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "amine" as used herein describes a primary, secondary, tertiary or cyclic amine. An amine may be an alkylamine, an arylamine, an alkylarylamine, an aliphatic amine or an aromatic amine. A primary amine has one of three hydrogen atoms replaced by an alkyl or aromatic. Non-limiting examples of primary alkyl amines include methylamine, ethanolamine (2-aminoethanol), and tris, while primary aromatic amines include aniline. A secondary amines has two organic substituents (alkyl, aryl or both) bound to N together with one hydrogen (or no hydrogen if one of the substituent bonds is double). Non-limiting examples include dimethylamine and methylethanolamine, while an example of an aromatic amine would be diphenylamine. A tertiary amines has all three hydrogen atoms replaced by organic substituents. Examples include trimethylamine or triphenylamine. A cyclic amine is either a secondary or a tertiary amine. Examples of cyclic amines include the 3-member ring aziridine and the six-membered ring piperidine. N-methylpiperidine and N-phenylpiperidine are examples of cyclic tertiary amines.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "indole" as used herein denotes an aromatic heterocyclic organic compound. The indole has a bicyclic structure, consisting of a six-membered benzene ring fused to a five-membered nitrogen-containing pyrrole ring. The indole may be optionally substituted at any position along the benzene ring. Additionally, the indole may be substituted at any position along the pyrrole ring. Further, the nitrogen of the pyrrole may be substituted with another element. Non-limiting examples may include sulfur or oxygen.

The term "oxygen-protecting group" as used herein denotes a group capable of protecting an oxygen atom (and hence, forming a protected hydroxyl group), wherein the protecting group may be removed, subsequent to the reaction for which protection is employed, without disturbing the remainder of the molecule. Exemplary oxygen protecting groups include ethers (e.g., allyl, triphenylmethyl (trityl or Tr), p-methoxybenzyl (PMB), p-methoxyphenyl (PMP)); acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)); esters (e.g., benzoate (Bz), allyl carbonate, 2,2,2-trichloroethyl carbonate (Troc), 2-trimethylsilylethyl carbonate); silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS)) and the like. A variety of oxygen protecting groups and the synthesis thereof may be found in "Protective Groups in Organic Synthesis" by T. W. Greene and P. G. M. Wuts, $3^{rd}$ ed., John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate certain embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

JVM 1

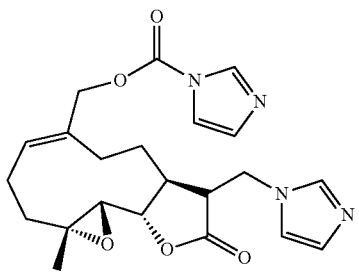

To a stirred solution of MMB (50 mg, 0.189 mmol) in dichloromethane, was added carbonyldiimidazole (46.02 mg, 0.284 mmol). The reaction mixture was stirred at ambient temperature for 24 hours. After completion of the reaction, the reaction mixture was diluted with chloroform (2 mL). The organic layer was washed with 10% citric acid solution (2 mL), dried over $Na_2SO_4$, and concentrated under reduced pressure. The residue was purified by column chromatography (silica gel eluted with 3% methanol in dichloromethane) to afford compound JVM 1 as an off-white solid (yield: 75%).

$^1$H-NMR (CDCl$_3$, 400 MHz) δ 8.13 (s, 1H), 7.68 (s, 1H), 7.42 (s, 1H), 7.09-7.05 (m, 3H), 5.72 (t, J=8 Hz, 1H), 4.94 (d, J=12 Hz, 1H), 4.55 (d, J=12.8 Hz, 2H), 4.36 (d, J=16 Hz, 1H), 3.902-3.856 (m, 1H), 2.79 (t, J=11.8 Hz, 1H), 2.60 (d, J=8 Hz, M), 2.44-1.91 (m, 8H), 1.83-1.74 (m, 1H), 1.66 (t, J=12 Hz, 1H), 1.52 (s, 1H), 1.07 (t, J=12 Hz, 1H); $^{13}$C NMR (CDCl$_3$, 100 MHz) δ 174.5, 148.7, 137.7, 137.0, 133.3, 132.7, 130.9, 130.6, 119.4, 117.1, 80.8, 69.8, 62.4, 59.9, 48.3, 43.7, 40.9, 36.2, 26.5, 23.8, 23.6, 17.8 ppm.

Example 2

JVM 57 (6d in Example 19)

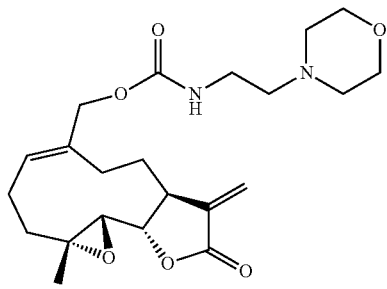 [SMILES: C=C1C(=O)O[C@H]2[C@H]1CC/C(COC(=O)NCCN1CCOCC1)=C\CC[C@@]1(C)O[C@@H]21]

4-(2-Aminoethyl)morpholine (25 mg, 0.19 mmol) in dichloromethane (2 mL) was added at 0° C. to the triazole intermediate of MMB (JVM 2-16) (70 mg, 0.19 mmol). The reaction mixture was stirred for 15 hours. Upon completion of the reaction, as determined by TLC, water was added to the reaction mixture and the resulting aqueous mixture was extracted with dichloromethane. The organic layer was washed with water followed by brine, dried over anhydrous $Na_2SO_4$, and concentrated to afford the crude product. The crude product was purified by column chromatography (silica gel eluted with 3% methanol in dichloromethane) to afford compound JVM 57 as a white solid (yield: 60%).

$^1$H NMR (CDCl$_3$, 400 MHz): δ 6.11 (d, J=3.6 Hz, 1H), 5.58 (t, J=8 Hz, 1H), 5.43 (d, J=2.8 Hz, 1H), 5.06 (s, 1H), 4.53 (d, J=12.4 Hz, 1H), 4.34 (d, J=12 Hz, 1H), 3.74 (t, J=8.8 Hz, 1H), 3.56 (s, 4H), 3.16 (t, J=5.2 Hz, 2H), 2.78-2.72 (m, 2H), 2.32 (s, 8H), 2.21-2.00 (m, 4H), 1.55 (t, J=10.4 Hz, 1H), 1.41 (s, 3H), 1.01 (t, J=12 Hz, 1H) ppm. $^{13}$C NMR (CDCl3, 100 MHz) δ 169.2, 155.9, 138.7, 135.4, 130.2, 120.0, 80.9, 67.0, 66.7, 63.1, 59.8, 57.2, 53.1, 42.5, 37.0, 36.5, 25.7, 24.4, 23.7, 17.8 ppm.

Example 3

JVM 59 (6b in Example 19)

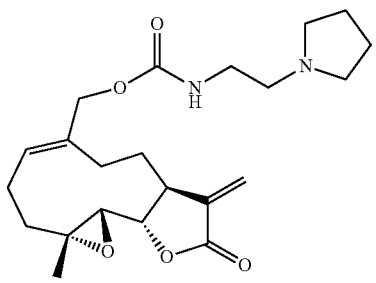 [SMILES: C=C1C(=O)O[C@H]2[C@H]1CC/C(COC(=O)NCCN1CCCC1)=C\CC[C@@]1(C)O[C@@H]21]

To the triazole intermediate of MMB (JVM 2-16) (70 mg, 0.19 mmol) in dichloromethane (2 mL) at 0° C. was added 1-(2-aminoethyl)pyrrolidine (21.6 mg, 0.19 mmol). The reaction mixture was stirred for 16 hours. Upon completion of the reaction, as determined by TLC, water was added to the reaction mixture and the aqueous mixture was extracted with dichloromethane. The organic layer was washed with water followed by brine, dried over anhydrous $Na_2SO_4$, and concentrated to afford the crude product. The crude product was purified by column chromatography (silica gel eluted with 5% methanol in dichloromethane) to afford compound JVM 59 as a white solid (yield: 55%).

$^1$H NMR (CDCl$_3$, 400 MHz): δ 6.22 (d, J=3.2 Hz, 1H), 5.65 (t, J=7 Hz, 1H), 5.55 (s, 1H), 4.62 (d, J=11.6 Hz, 1H), 4.47 (d, J=12.4 Hz, 1H), 3.82 (t, J=9.6 Hz, 1H), 3.35 (s, 2H), 2.90-2.83 (m, 2H), 2.70 (s, 4H), 2.42 (d, J=9.6 Hz, 2H), 2.38-2.13 (m, 7H) 1.84 (s, 4H), 1.66 (t, J=12 Hz, 1H), 1.52 (s, 3H), 1.13 (t, J=11.6 Hz, 1H) ppm. $^{13}$C NMR (CDCl3, 100 MHz) δ 169.3, 156.1, 138.6, 135.3, 129.8, 120.1, 80.9, 67.0, 63.1, 59.8, 55.1, 53.8, 42.5, 38.9, 36.5, 25.6, 24.3, 23.6, 23.2, 17.8 ppm.

Example 4

JVM 61 (6c in Example 19)

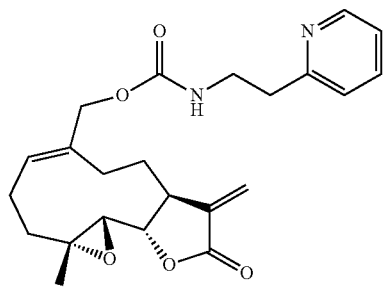 [SMILES: C=C1C(=O)O[C@H]2[C@H]1CC/C(COC(=O)NCCc1ccccn1)=C\CC[C@@]1(C)O[C@@H]21]

To the triazole intermediate of MMB (JVM 2-16) (70 mg, 0.19 mmol) in dichloromethane (2 mL), 2-ethylaminopyridine (23.18 mg, 0.19 mmol) was added at 0° C. The reaction mixture was stirred for 16 hours. Upon completion as determined by TLC, water was added to the reaction mixture and the aqueous mixture was extracted with dichloromethane. The organic layer was washed with water followed by brine, dried over anhydrous $Na_2SO_4$, and concentrated to afford the crude product. The crude product was purified by column chromatography (silica gel eluted with 5% methanol in dichloromethane) to afford compound JVM 61 as a white solid (yield: 65%).

$^1$H NMR (CDCl$_3$, 400 MHz): δ 8.50 (s, 1H), 7.62 (t, J=7.2 Hz, 1H), 7.15 (d, J=7.6 Hz, 2H), 6.19 (s, 1H), 5.64 (t, J=8 Hz, 1H), 5.56 (m, 2H), 4.62 (d, J=12.4 Hz, 1H), 4.44 (d, J=12.8 Hz, 1H), 3.84 (t, J=9.2 Hz, 1H), 3.60 (d, J=6 Hz, 2H), 2.99-2.82 (m, 4H), 2.41-2.12 (m, 5H), 1.75 (s, 1H), 1.64 (d, J=10.4 Hz, 1H), 1.52 (s, 3H), 1.07 (t, J=13.6 Hz, 1H). $^{13}$C NMR (CDCl$_3$, 100 MHz): δ 169.3, 159.1, 156.0, 149.1, 138.6, 136.6, 135.5, 129.9, 123.4, 121.6, 120.2, 81.0, 67.0, 63.2, 59.8, 42.5, 40.1, 37.1, 36.6, 25.8, 24.4, 23.7, 17.9 ppm.

Example 5

JVM 64 (6e in Example 19)

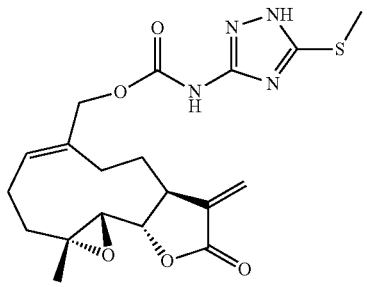 [SMILES: C=C1C(=O)O[C@H]2[C@H]1CC/C(COC(=O)Nc1n[nH]c(SC)n1)=C\CC[C@@]1(C)O[C@@H]21]

To the triazole intermediate of MMB (JVM 2-16) (70 mg, 0.19 mmol) in dichloromethane (2 mL), 5-(methylthio)-1H-1,2,4-triazol-3-amine (24.7 mg, 0.19 mmol) was added at 0° C. The reaction mixture was stirred for 8 hours. Upon completion as determined by TLC, water was added to the reaction mixture and the aqueous mixture was extracted with dichloromethane. The organic layer was washed with water followed by brine, dried over anhydrous Na$_2$SO$_4$, and concentrated to afford the crude product. The crude product was purified by column chromatography (silica gel eluted with 3% methanol in dichloromethane) to afford compound JVM 64 as a white solid (yield: 62%).

$^1$H NMR (CDCl$_3$, 400 MHz): δ 6.22 (s, 2H), 5.82 (t, J=8 Hz, 1H), 5.50 (s, 1H), 4.90 (d, J=12.4 Hz, 1H), 4.81 (d, J=12.4 Hz, 1H), 3.85 (t, 9.6 Hz, 1H), 2.95 (s, 1H), 2.85 (d, J=9.2 Hz, 1H), 2.48-2.15 (m, 8H), 1.70-1.53 (m, 6H), 1.13 (t, J=12.4 Hz, 1H); $^{13}$C NMR (CDCl$_3$, 100 MHz): δ 169.1, 163.1, 157.4, 149.9, 138.5, 133.3, 132.7, 120.2, 80.7, 70.1, 62.9, 59.7, 42.4, 36.2, 25.6, 24.3, 23.7, 17.8, 13.5 ppm.

Example 6

JVM 66

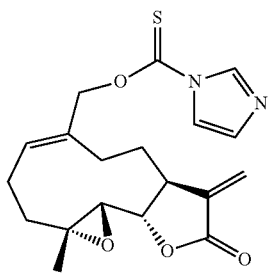 [SMILES: C=C1C(=O)O[C@H]2[C@H]1CC/C(COC(=S)n1ccnc1)=C\CC[C@@]1(C)O[C@@H]21]

To a stirred solution of MMB (50 mg, 0.19 mmol) in chloroform (2 mL), thiocarbonyldiimidazole (33.8 mg, 0.19 mmol) was added at ambient temperature. The reaction was maintained for 1 hour at ambient temperature. Upon completion as determined by TLC, water was added and the aqueous mixture was extracted with dichloromethane. The organic layer was dried over anhydrous Na$_2$SO$_4$ and concentrated to afford the crude product. The crude product was purified by column chromatography (silica gel eluted with a gradient of 3-8% methanol in dichloromethane) to afford compound JVM 66 as an off-white solid (yield: 60%) and compound JVM 66A as a white solid (yield: 15%).

$^1$H NMR (CDCl$_3$, 400 MHz): δ 8.11 (s, 1H), 7.38 (s, 1H), 7.07 (s, 1H), 6.22 (s, 1H), 5.52 (s, 2H), 5.14 (s, 1H), 4.30 (s, 1H), 3.78 (t, J=8.8 Hz, 1H), 3.16 (s, 1H), 2.94 (d, J=8.8 Hz, 1H), 2.47 (q, J=17.2 Hz, 2H), 2.3-2.18 (m, 3H), 1.77-1.66 (m, 2H), 1.39 (s, 3H), 1.32-1.23 (m, 1H); $^{13}$C NMR (CDCl$_3$, 100 MHz): δ 168.9, 165.1, 143.8, 138.7, 135.2, 131.0, 119.8, 116.4, 115.6, 79.4, 63.0, 59.8, 53.3, 45.1, 37.4, 29.8, 28.2, 24.7, 17.8 ppm.

Example 7

JVM 67

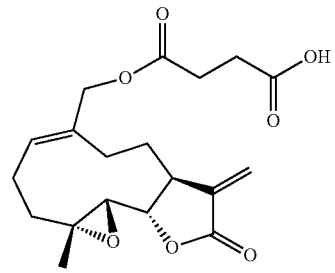 [SMILES: C=C1C(=O)O[C@H]2[C@H]1CC/C(COC(=O)CCC(=O)O)=C\CC[C@@]1(C)O[C@@H]21]

To a reaction mixture of MMB (200 mg, 0.76 mmol) and triethylamine (76.7 mg, 0.76 mmol) in dichloromethane (5 mL), succinic anhydride (76 mg, 0.76 mmol) was added at ambient temperature. The resulting reaction mixture was stirred for 48 hours. Upon completion as determined by TLC, the reaction mixture was concentrated under reduced pressure to afford the crude product. The crude product was purified by column chromatography (silica gel eluted with a gradient of 3-5% methanol in dichloromethane) to afford compound JVM 67 as a white solid (yield: 90%).

$^1$H NMR (DMSO-d$_6$, 400 MHz): δ 12.25 (s, 1H), 6.05 (d, J=2.8 Hz, 1H), 5.64-5.57 (m, 2H), 4.64 (d, J=12.4 Hz, 1H), 4.42 (d, J=12.8 Hz, 1H), 4.12 (t, J=9.6 Hz, 1H), 2.99 (t, J=3 Hz, 1H), 2.85 (d, J=9.6 Hz, 1H), 2.30-2.04 (m, 10H), 1.66 (t, J=11.6 Hz, 1H), 1.47 (s, 3H), 0.96 (t, J=11.6 Hz, 1H); $^{13}$C NMR (DMSO-d$_6$, 100 MHz): δ 173.8, 172.4, 169.8, 140.0, 135.3, 129.5, 119.7, 110.0, 81.0, 66.9, 63.0, 60.3, 42.2, 36.7, 29.1, 25.0, 24.2, 23.6, 17.9 ppm.

Example 8

JVM 88

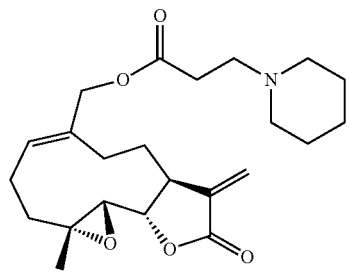 [SMILES: C=C1C(=O)O[C@H]2[C@H]1CC/C(COC(=O)CCN1CCCCC1)=C\CC[C@@]1(C)O[C@@H]21]

To a stirred solution of MMB (50 mg, 0.19 mmol) in dichloromethane (2 mL), was added 1-ethyl-3-(3-dimethylaminopropyl)carbodiimide (EDC, 43.93 mg, 0.23 mmol), triethylamine (48.4 mg, 0.48 mmol), dimethylaminopyridine (DMAP, 2.3 mg, 0.019 mmol) and 1-piperidylpropionic acid (29.8 mg, 0.19 mmol) at 0° C. The reaction mixture was stirred at ambient temperature for 24 hours. Upon completion, water was added and the mixture was extracted with dichloromethane. The organic layer was washed with water followed by brine, dried over anhydrous Na$_2$SO$_4$, and concentrated to afford the crude product. The crude product was purified by column chromatography (silica gel eluted with 2% methanol in dichloromethane) to afford compound JVM 88 as a white solid (yield: 62%).

$^1$H NMR (CDCl$_3$, 400 MHz): δ 6.23 (d, J=3.6 Hz, 1H), 5.65 (t, J=8 Hz, 1H), 5.52 (d, J=3.2 Hz, 1H), 4.69 (d, J=12.4 Hz, 1H), 4.42 (d, J=12.4 Hz, 1H), 3.84 (t, J=9.2 Hz, 1H), 2.85-2.81 (m, 2H), 2.65-2.62 (m, 2H), 2.52-2.48 (m, 2H), 2.42-2.12 (m, 10H), 1.63-1.52 (m, 8H), 1.41 (d, J=4.4 Hz, 2H), 1.10 (t, J=12 Hz, 1H); $^{13}$C NMR (CDCl$_3$, 100 MHz): δ 172.4, 169.4, 138.8, 135.0, 130.5, 120.4, 81.1, 66.6, 63.4, 60.0, 54.4, 54.3, 42.7, 36.7, 32.3, 25.9, 25.8, 24.4, 24.2, 23.9, 18.1 ppm.

Example 9

JVM 96

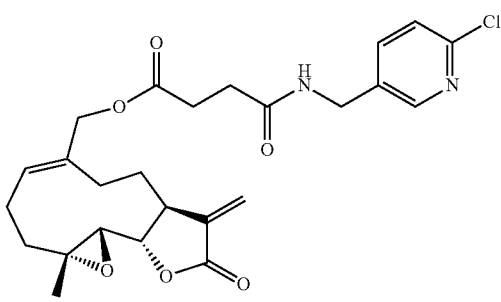 [SMILES: C=C1C(=O)O[C@H]2[C@H]1CC/C(COC(=O)CCC(=O)NCc1ccc(Cl)nc1)=C\CC[C@@]1(C)O[C@@H]21]

To a reaction mixture of MMB carboxylic acid (JVM 67), (50 mg, 0.14 mmol), EDC (40.26 mg, 0.21 mmol), N-hydroxybenzotriazole (HOBt, 28.35 mg, 0.21 mmol), and triethylamine (42.42 mg, 0.42 mmol) in dichloromethane (2 mL) was added 3-aminomethyl-6-chloropyridine (19.96 mg, 0.14 mmol) at 0° C. and the reaction mixture was stirred at ambient temperature for 16 hours. Upon completion as determined by TLC, water was added and the mixture extracted with dichloromethane. The organic layer was dried and concentrated to afford the crude compound. The crude product was further purified by column chromatography (silica gel using 3% methanol in dichloromethane) to afford JVM 96 as pure product as white solid (yield 75%).

$^1$H NMR (CDCl$_3$, 400 MHz): δ 8.28 (s, 1H), 7.61 (d, J=8.4 Hz, 1H), 7.29 (d, J=8.4 Hz, 1H), 6.22 (d, J=3.2 Hz, 1H), 6.07 (s, 1H), 5.68 (t, J=7.2 Hz, 1H), 5.55 (s, 1H), 4.65 (d, J=12.4 Hz, 1H), 4.49 (d, J=12.8 Hz, 1H), 4.42 (d, J=5.6 Hz, 2H), 3.85 (t, J=9.6 Hz, 1H), 2.95 (t, J=8.8 Hz, 1H), 2.85 (d, J=9.6 Hz, 1H), 2.68 (t, J=6 Hz, 2H), 2.52-2.11 (m, 7H), 1.67-1.62 (m, 2H), 1.53 (s, 3H), 1.12 (t, J=11.6 Hz, 1H); $^{13}$C NMR (CDCl$_3$, 100 MHz): δ 172.8, 171.5, 169.6, 150.7, 148.9, 138.9, 138.6, 134.8, 133.1, 130.8, 124.4, 120.4, 81.2, 67.2, 63.3, 60.1, 42.7, 40.5, 36.7, 30.7, 29.3, 25.8, 24.6, 23.9, 18.1 ppm.

Example 10

JVM 2-16

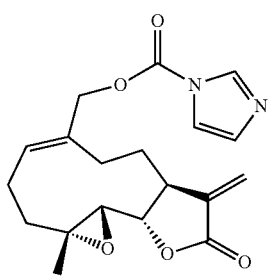 [SMILES: C=C1C(=O)O[C@H]2[C@H]1CC/C(COC(=O)n1ccnc1)=C\CC[C@@]1(C)O[C@@H]21]

To a stirred solution of MMB (50 mg, 0.18 mmol) in dichloromethane, carbonyldithriazole (46.5 mg, 0.28 mmol) was added at ambient temperature. The reaction mixture was stirred at ambient temperature for 10 minutes. Upon completion, water was added and the mixture extracted with dichloromethane, dried over Na$_2$SO$_4$ and concentrated under reduced pressure to afford pure product JVM 2-16 as white solid (yield: 85%).

$^1$H NMR (CDCl$_3$, 400 MHz): δ 8.83 (s, 1H), 8.06 (s, 1H), 6.26 (d, J=3.6 Hz, 1H), 5.92 (t, J=8.4 Hz, 1H), 5.55 (d, J=3.2 Hz, 1H), 5.08 (d, J=11.6 Hz, 1H), 4.90 (d, J=12 Hz, 1H), 3.89 (t, J=9.6 Hz, 1H), 2.91 (m, 2H), 2.56-2.17 (m, 6H), 1.84-1.72 (m, 1H), 1.55 (s, 3H), 1.17 (t, J=12.4 Hz, 1H); $^{13}$C NMR (CDCl$_3$, 100 MHz): δ 169.2, 154.0, 147.7, 145.8, 138.6, 134.4, 133.3, 120.6, 80.9, 71.5, 63.3, 59.9, 42.7, 36.5, 25.7, 24.3, 24.1, 18.1 ppm.

Example 11

JVM 2-26

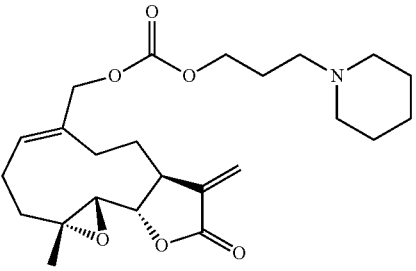 [SMILES: C=C1C(=O)O[C@H]2[C@H]1CC/C(COC(=O)OCCCN1CCCCC1)=C\CC[C@@]1(C)O[C@@H]21]

To a stirred solution of MMB (50 mg, 0.18 mmol) in dichloromethane (2 mL), carbonyldithriazole (46.5 mg, 0.28 mmol) was added at ambient temperature. The reaction mixture was stirred for 10 minutes and piperidine-1-propanol (40 mg, 0.28 mmol) was added, and the reaction mixture was maintained at ambient temperature for 30 minutes. Upon completed as determined by TLC, water was added and the mixture extracted with dichloromethane. The organic layer was dried over Na$_2$SO$_4$ and concentrated to afford a crude product. The crude compound was purified by column chromatography (silica gel eluted with 3% methanol in dichloromethane) to afford pure product JVM 2-26, as a white solid (yield: 81%).

$^1$H NMR (CDCl$_3$, 400 MHz): δ 6.24 (d, J=3.6 Hz, 1H), 5.74 (t, J=7.6 Hz, 1H), 5.55 (d, J=3.2 Hz, 1H), 4.65 (d, J=12 Hz, 1H), 4.55 (d, J=12 Hz, 1H), 4.19 (t, J=6 Hz, 2H), 3.86 (t, J=8.8 Hz, 1H), 2.88-2.82 (m, 2H), 2.46-2.13 (m, 12H), 1.92 (s, 2H), 1.70-1.64 (m, 5H), 1.53 (s, 3H), 1.45 (s, 2H), 1.13 (t, J=11.6 Hz, 1H); $^{13}$C NMR (CDCl$_3$, 100 MHz): δ 169.5, 155.0, 138.7, 134.5, 131.7, 120.4, 81.1, 70.3, 66.8, 63.4, 60.0, 55.5, 54.5, 42.7, 36.6, 25.9, 25.5, 24.5, 24.1, 24.1, 23.9, 18.1 ppm.

Example 12

JVM 2-31

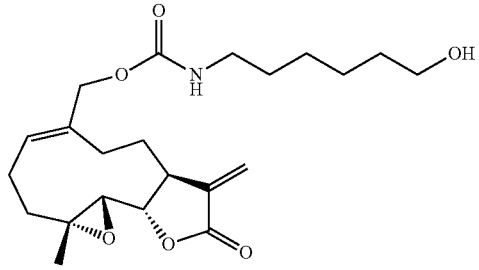 [SMILES: C=C1C(=O)O[C@H]2[C@H]1CC/C(COC(=O)NCCCCCCO)=C\CC[C@@]1(C)O[C@@H]21]

To a stirred solution of MMB (50 mg, 0.18 mmol) in dichloromethane at ambient temperature, was added carbonylditriazole (46.5 mg, 0.28 mmol). The reaction mixture was stirred for 10 minutes. 6-Amino-1-hexanol (32.7 mg, 0.28 mmol) was then added and the reaction was maintained for 30 minutes at ambient temperature. Upon completion of the reaction, as determined by TLC, water was added and the mixture extracted with dichloromethane. The organic layer was dried over anhydrous $Na_2SO_4$ and concentrated to afford the crude product. The crude compound was purified by column chromatography (silica gel eluted with 3% methanol in dichloromethane) to afford the pure product, JVM 2-31, as a colorless oil (yield: 85%).

$^1$H NMR (CDCl$_3$, 400 MHz): δ 6.28 (d, J=3.6 Hz, 1H), 5.73 (t, J=8 Hz, 1H), 5.59 (d, J=3.2 Hz, 1H), 4.68-4.63 (m, 2H), 4.51 (d, J=12.4 Hz, 1H), 3.90 (t, J=9.2 Hz, 2H), 3.68 (t, J=6 Hz, 2H), 3.21 (d, J=6.4 Hz, 2H), 2.98-2.88 (m, 2H), 2.46-2.16 (m, 6H), 1.71-1.51 (m, 8H), 1.45-1.36 (m, 4H), 1.16 (t, d, J=11.6 Hz, 1H) ppm; $^{13}$C NMR (CDCl$_3$, 100 MHz): δ 169.6, 156.3, 138.9, 135.7, 130.3, 120.3, 81.2, 67.2, 63.4, 62.8, 60.1, 42.7, 41.0, 36.7, 32.6, 30.0, 26.5, 25.9, 25.4, 24.7, 23.9, 18.1 ppm.

Example 13

JVM 2-35

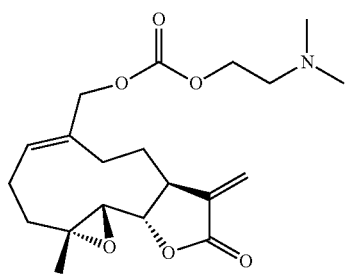 [SMILES: C=C1C(=O)O[C@H]2[C@H]1CC/C(COC(=O)OCCN(C)C)=C\CC[C@@]1(C)O[C@@H]21]

To a stirred solution of MMB (50 mg, 0.18 mmol) in dichloromethane, carbonylditriazole (46.5 mg, 0.28 mmol) was added at ambient temperature. The reaction mixture was stirred for 10 minutes. N,N-dimethylethanolamine (24.9 mg, 0.28 mmol) was then added and the reaction was maintained for 30 minutes at ambient temperature. Upon completion as determined by TLC, water was added and the mixture extracted with dichloromethane. The organic layer was dried over $Na_2SO_4$ and concentrated to afford the crude product. The crude compound was purified by column chromatography (silica gel eluted with 4% methanol in dichloromethane) to afford the pure product, JVM 2-35 as a white solid (yield: 81%).

$^1$H NMR (CDCl$_3$, 400 MHz) δ 6.24 (d, J=3.6 Hz, 1H), 5.74 (t, J=8.4 Hz, 1H), 5.55 (d, J=3.2 Hz, 1H), 4.65 (d, J=12 Hz, 1H), 4.56 (d, J=12.4 Hz, 1H), 4.24 (s, 2H), 3.85 (t, J=9.6 Hz, 1H), 2.84 (d, J=9.2 Hz, 2H), 2.62 (s, 2H), 2.47-2.12 (m, 12H), 1.72-1.60 (m, 1H), 1.53 (s, 3H), 1.12 (t, J=11.6 Hz, 1H); $^{13}$C NMR (CDCl$_3$, 100 MHz): δ 169.5, 155.1, 138.7, 134.5, 131.6, 120.5, 81.1, 70.4, 65.4, 63.4, 60.0, 57.6, 45.6, 42.7, 36.6, 25.8, 24.4, 23.9, 18.1 ppm.

Example 14

JVM 2-40

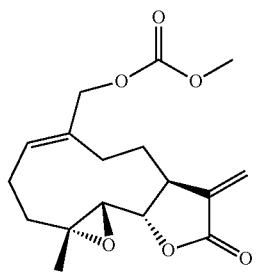 [SMILES: C=C1C(=O)O[C@H]2[C@H]1CC/C(COC(=O)OC)=C\CC[C@@]1(C)O[C@@H]21]

To a stirred solution of MMB (50 mg, 0.18 mmol) in methanol (2 mL), carbonylditriazole (46.5 mg, 0.28 mmol) was added at ambient temperature. The reaction mixture was stirred at same temperature for 1 hour. Upon completion as determined by TLC, the reaction mixture was concentrated under reduced pressure and the crude compound was purified by column chromatography (silica gel eluted with 2% methanol in dichloromethane) to afford pure product, JVM 2-40, as a white solid (yield: 80%).

$^1$H NMR (CDCl$_3$, 400 MHz): δ 6.24 (s, 1H), 5.72 (s, 1H), 5.53 (s, 1H), 4.65 (d, t, J=11.6 Hz, 1H), 4.56 (d, J=12 Hz, 1H), 3.85 (t, J=9.6 Hz, 1H), 3.77 (s, 3H), 2.83 (d, J=9.6 Hz, 2H), 2.44-2.13 (m, 6H), 1.66 (t, J=11.6 Hz, 1H), 1.52 (s, 3H), 1.12 (t, J=11.6 Hz, 1H); $^{13}$C NMR (CDCl$_3$, 100 MHz): δ 169.4, 155.7, 138.7, 134.5, 131.6, 120.4, 81.1, 70.4, 63.4, 60.0, 55.1, 42.7, 36.6, 25.8, 24.4, 23.9, 18.1 ppm.

Example 15

JVM 2-41

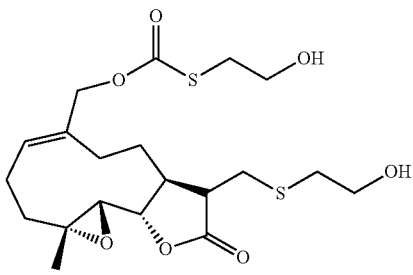

To a stirred solution of MMB (50 mg, 0.18 mmol) in dichloromethane, was added carbonylditriazole (46.5 mg, 0.28 mmol). The reaction mixture was stirred at room temperature for 10 minutes, and mercaptoethanol (21.84 mg, 0.28 mmol) was added. The reaction was maintained for 30 minutes. Upon completion as determined by TLC, water was added and the mixture extracted with dichloromethane. The organic layer was dried over $Na_2SO_4$ and concentrated to afford the crude product. The crude compound was purified by column chromatography (silica gel eluted with 4% methanol in dichloromethane) to afford the pure product, JVM 2-41, as an oil (yield: 65%).

$^1$H NMR (CDCl$_3$, 400 MHz): δ 5.11 (t, J=8 Hz, 1H), 5.02 (d, J=12 Hz, 1H), 4.62 (d, J=12 Hz, 1H), 3.90-3.76 (m, 4H), 3.07-3.02 (m, 3H), 2.84-2.74 (m, 3H), 2.61-2.57 (m, 1H), 2.47-2.12 (m, 7H), 1.99 (s, 4H), 1.63-1.57 (m, 1H), 1.53 (s, 3H), 1.11 (t, J=12.4 Hz, 1H); $^{13}$C NMR (CDCl$_3$, 100 MHz): δ 175.9, 171.6, 134.7, 131.3, 81.2, 70.0, 63.3, 61.8, 60.9, 60.0, 46.8, 42.7, 36.8, 36.6, 34.0, 29.7, 26.7, 24.2, 23.8, 18.0 ppm.

Example 16

JVM 2-49

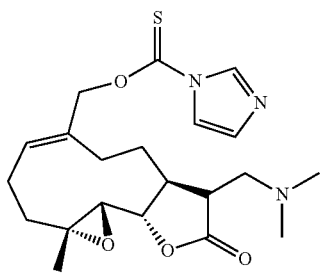

To the stirred solution of MMB (70 mg, 0.27 mmol) in dichloromethane, dimethylamine (14.40 mg, 0.32 mmol) in methanol was added the reaction mixture was maintained under ambient conditions for 2 hours. Upon completion, the reaction mixture was concentrated to remove solvent. The crude reaction mixture dissolved in dichloromethane and added the thiocarbonyldiimidazole (72 mg, 0.41 mmol). The reaction mixture was maintained at ambient temperature for 3 hours. Upon completion, the reaction mixture was concentrated and purified by column chromatography (silica gel eluted with 3% methanol in dichloromethane) to afford pure product.

$^1$H NMR (CDCl$_3$, 400 MHz): δ 8.12 (s, 1H), 7.38 (s, 1H), 7.07 (s, 1H), 5.51 (s, 1H), 5.19 (s, 1H), 4.32 (t, J=8 Hz, 1H), 3.80 (t, J=8 Hz, 1H), 2.99-2.03 (m, 17H), 1.6 (s, 1H), 1.41 (s, 3H), 1.29-1.23 (m, 1H); $^{13}$C NMR (CDCl$_3$, 100 MHz): δ 176.5, 165.4, 144.2, 135.5, 131.1, 116.8, 115.9, 79.7, 63.4, 60.0, 57.8, 53.8, 45.8, 45.3, 37.8, 30.0, 28.3, 26.1, 21.1, 18.0 ppm.

Example 17

Antileukemic Activity of Various MMB Derivatives

Derivatives were screened for antileukemic activity against AML cells in culture (See FIGS. 1-7). Compounds JVM 64, JVM 66, JVM 2-26, and JVM 2-49 (Examples 5, 6, 11, and 16, respectively) were the most active compounds against AML 052308 cells in culture and were more potent than MMB. JVM 66 (a thiocarbamate derivative of MMB, Example 6) was the most active molecule of this group with an LC$_{50}$ value of 2.6 μM, and was about 6-fold more cytotoxic than MMB (LC$_{50}$=16 μM); JVM 66 was also 3-fold more potent than parthenolide (LC$_{50}$=7.6 μM). The derivatives JVM 2-26, JVM 2-49, and JVM 64 (Examples 11, 16, and 5, respectively) exhibited similar cytotoxicity to parthenolide (LC$_{50}$=5, 5.2, 7.4 μM) and were 3-fold more cytotoxic than MMB against AML 052308 cells. JVM 61 (Example 4), JVM 59 (Example 3), and JVM 74 showed almost equal cytotoxicity to MMB, while JVM 57 (Example 2) and JVM 58 were less active than MMB. Compound JVM 88 (Example 8) was screened for antileukemic activity against the M9 ENL cell line, and against the AML 123009 and AML 100510 primary isolates, exhibiting good antileukemic activity compared to MMB in these cellular assays.

Figure 10:
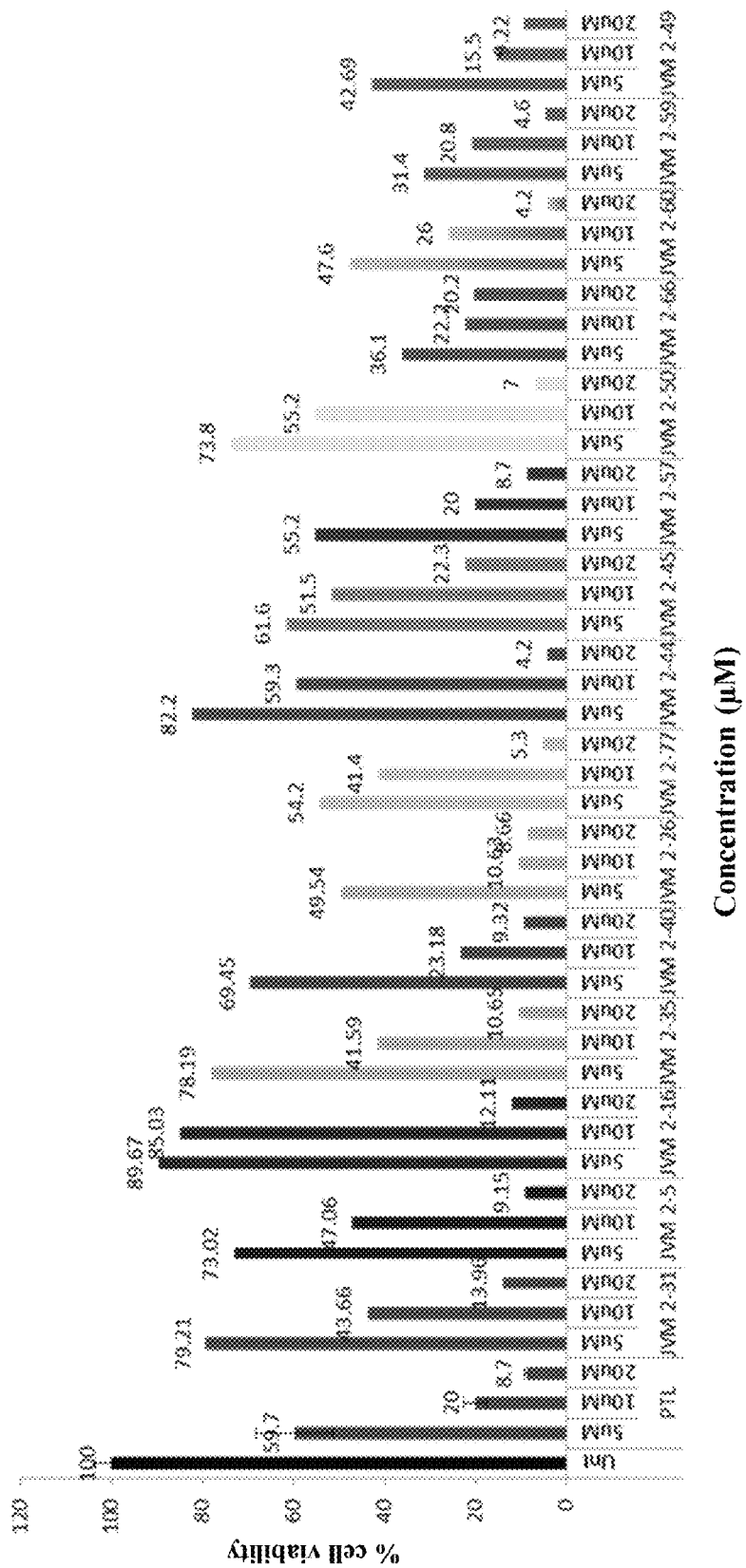
FIG. 10 shows a graph demonstrating the anti-leukemic activity of carbamate and carbonate derivatives of melampomagnolide B against M9 ENL cells.
Figure 11:
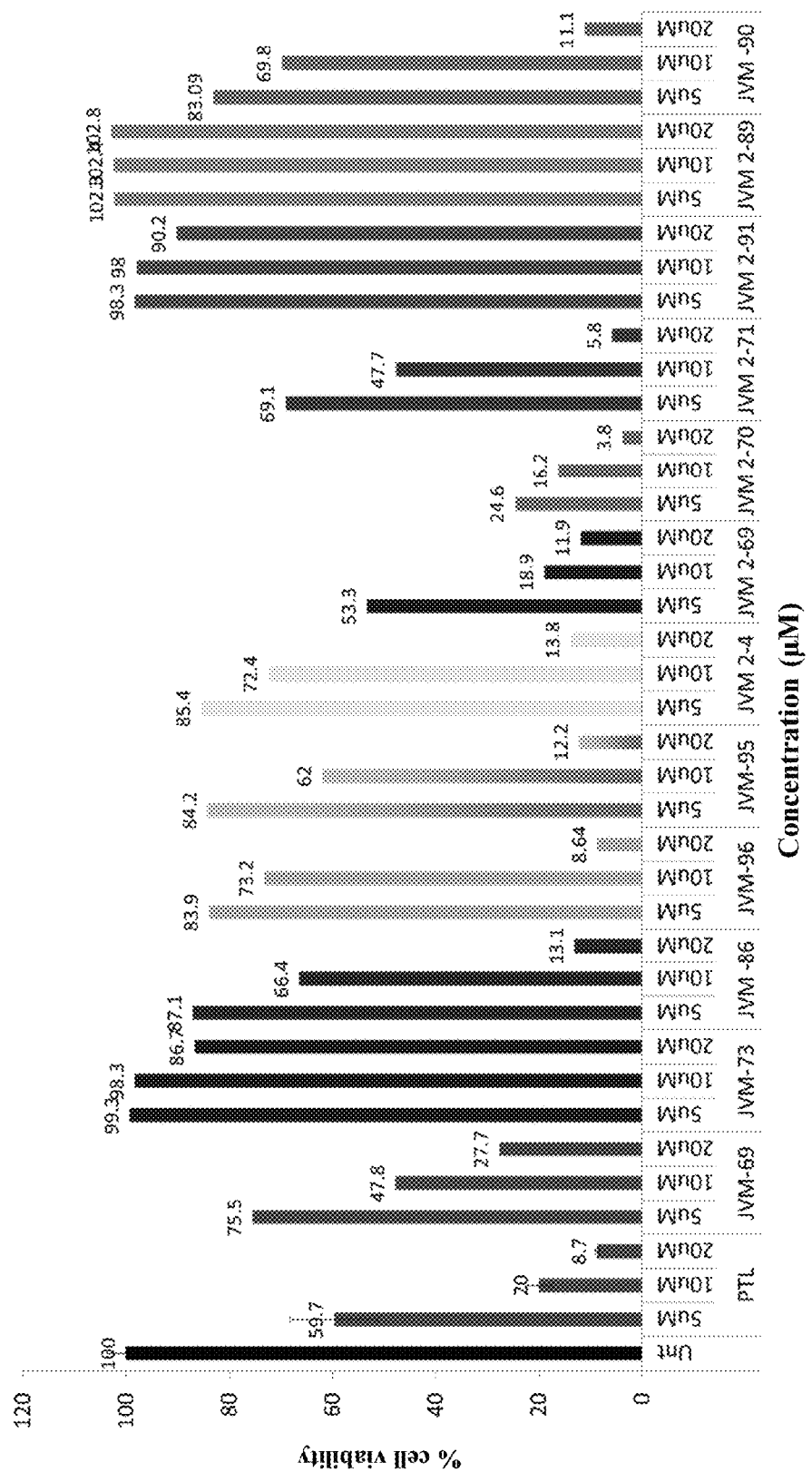
FIG. 11 shows a graph demonstrating the anti-leukemic activity of succinic amide derivatives of melampomagnolide B against M9 ENL cells.

Carbamate and carbonate derivatives of MMB were also screened for activity against M9 ENL cells at concentrations of 5, 10 and 20 μM (FIG. 10). JVM 2-66, JVM 2-60, JVM 2-59, and JVM 2-49 reduced cell viability by greater than 50% at the lowest concentration tested. Additionally, succinic amide derivatives of MMB were screened for activity against M9 ENL cells at concentrations of 5, 10 and 20 μM (FIG. 11). JVM 2-70 reduced cell viability by greater than 50% at the lowest concentration tested.

Example 18

In Vitro Growth Inhibition and Cytotoxicity

The compounds disclosed herein were also screened for anticancer activity against a panel of 60 human tumor cell lines. The compounds were first screened at a single concentration of 10$^{-5}$ M. Compounds which showed more than 60% growth inhibition in at least eight human cancer cell lines from the panel were selected for a complete dose-response study at five concentrations: 10$^{-4}$ M, 10$^{-5}$ M, 10$^{-6}$ M, 10$^{-7}$ M, and 10$^{-8}$ M. From the initial single dose screening, 16 compounds were selected for a five-dose screening: JVM 2-13, JVM 2-26, JVM 2-31, JVM 2-35, JVM 2-40, JVM 2-44, JVM 2-50, JVM 2-57, JVM 2-66, JVM 2-70, JVM-57 (6d), JVM-59 (6b), JVM-61 (6c), JVM-64 (6e), JVM-66, and JVM-96.

Example 19

Anti-Cancer Activity of Carbamate Derivatives of Melampomagnolide B (MMB)

Figure 8:
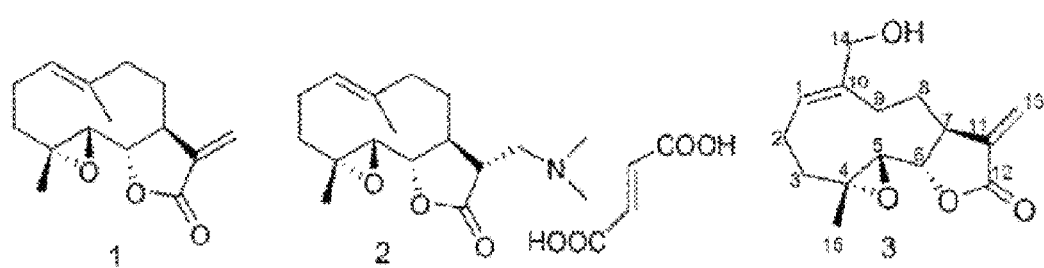
FIG. 8 shows structures of PTL (1), DMAPT fumarate (2) and MMB (3).

Parthenolide (PTL; 1, FIG. 8), a sesquiterpene lactone isolated from the medicinal herb Feverfew (*Tanacetum parthenium*), has been widely reported in the literature as an anticancer agent that is effective against both hematological and solid tumors.[1,2] PTL and its analogs promote apoptosis by inhibiting the activity of the NF-κB transcription factor complex, and thereby down-regulates anti-apoptotic genes under NF-κB control.[3] Recent studies also demonstrate that PTL induces robust apoptosis of primary acute myeloid leukemia (AML) stem cells in culture.[4,5] AML is a clonal malignancy of the hematopoietic system characterized by accumulation of immature cell populations in the bone marrow or peripheral blood,[6] and is the most common type of leukemia in adults but has the lowest survival rate of all leukemias.[7]

More recently, we have shown that PTL and PTL analogs also selectively induce almost complete glutathione depletion and severe cell death in CD34+ AML cells,[8] but exhibit significantly less toxicity in normal CD34+ cells. PTL analogs perturb glutathione homeostasis by a multifactorial mechanism, including inhibition of key glutathione metabolic enzymes (GCLC and GPX1), and direct depletion of glutathione. Thus, primitive leukemia cells are uniquely sensitive to agents that target aberrant glutathione metabolism, an intrinsic property of primary human AML cells.

PTL is a major source for several novel anti-leukemic compounds arising from our research program over the past decade. The two best examples are dimethylaminoparthenolide (DMAPT; 2, FIG. 8) and melampomagnolide B (MMB; 3, FIG. 8). MMB is a melampolide originally isolated from *Magnolia grandiflora*.[9] MMB can be synthesized from commercially available PTL via SeO$_2$/tBuOOH oxidation.[10,11] Both of the above compounds 2 and 3 have been identified as new antileukemic sesquiterpenes with properties similar to PTL.[11,12] DMAPT is currently in Phase 1 clinical studies for evaluation as a treatment for acute myeloid leukemia cell (AML).[12]

More importantly, from a drug design point of view, MMB is a more intriguing molecule than either PTL or DMAPT because of the presence of the primary hydroxyl group at C-14, which can be structurally modified to improve potency, water solubility, bio-availability and tissue targeting of the molecule.

In the current study, we have prepared a series of novel carbamate analogs of MMB. These compounds were initially designed as potential prodrugs of MMB. However, we have found that on examining the anticancer activity of these compounds, several of the molecules exhibited significant growth inhibition properties in a panel of sixty human cancer cell lines. Two of these compounds exhibited GI$_{50}$ values of ≤10 µM against the majority of the human cancer cell lines in the panel.

Carbamate analogs of MMB were prepared by reaction of the p-nitrophenyloxycarbonyl ester of MMB[13] with a variety of primary and secondary heterocyclic amines containing pyrrolidine, morpholine, piperidine, imidazole, triazole and pyridine moieties, to afford carbamate products 6a-6g[14] with generally improved water-solubility (Scheme 4, Table 1) compared to MMB. The key p-nitrophenyloxycarbonyl ester of MMB was prepared by the reaction of MMB with p-nitrophenylchloroformate in the presence of triethylamine. All conjugation reactions were carried out at ambient temperature in dichloromethane. We have reported previously that the reaction of sesquiterpenes containing an exocyclic double bond attached to the 13-position of the 5-membered lactone ring with primary and secondary amines leads to the facile formation of Michael addition products.[15] However, under the reaction conditions employed in Scheme 4, the rate of O-carbamoylation appears to be much faster than the rate of C-13 Michael addition, and only in a few cases, with amines such as 2-morpholinoethylamine, 2-piperidinoethylamine and 3-aminopropylimidazole, were Michael addition byproducts observed (usually in low yields of 5-10%), due likely to the high nucleophilicity of these amines.

Scheme 4. Synthesis of carbamoylated MMB analogs 6a-6g:

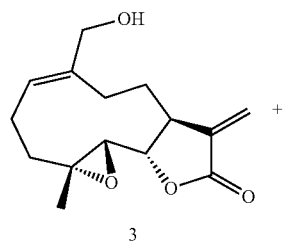

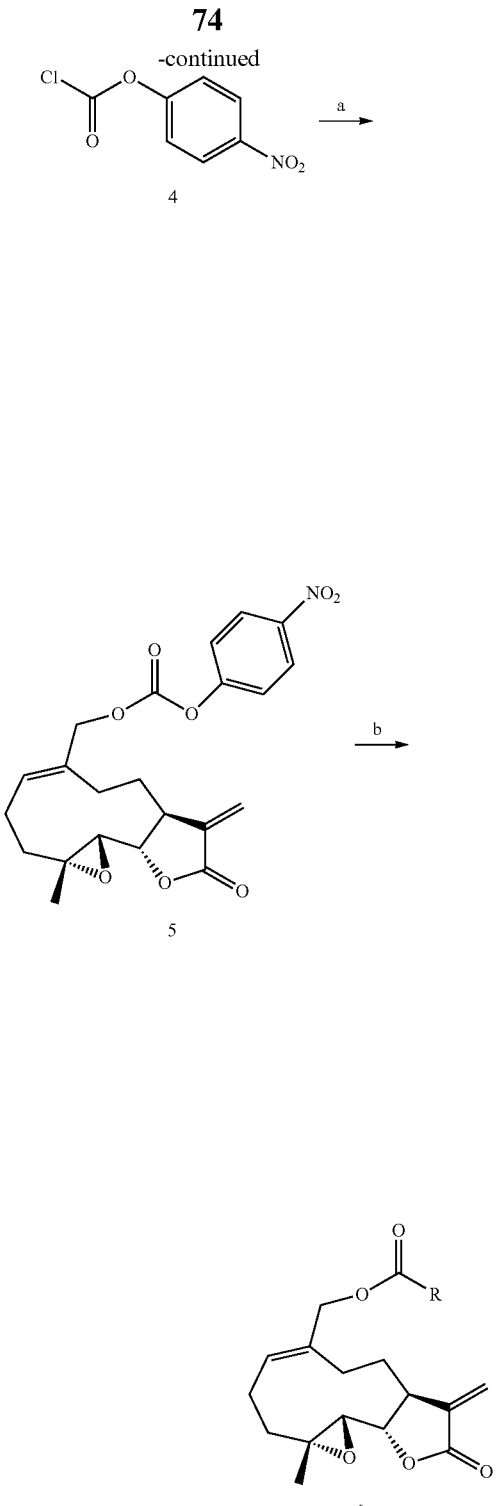

Reagents and conditions: (a) CH$_2$Cl$_2$, triethylamine, rt, 24 h; (b) CH$_2$Cl$_2$, heterocyclic amines, rt, 5-12 h.

All compounds were purified by column chromatography (silica gel; methanol/dichloromethane) to afford pure compounds in 50-75% yield. The synthesized compounds were fully characterized by $^1$H NMR, $^{13}$C NMR and high resolution mass spectral analysis.[14]

TABLE 1
Structures, reaction conditions, yields, and melting points for carbamate analogs of melampomagnolide B
| Amine | Product | Yield (%) | Time (h) | Mp (° C.) |
|---|---|---|---|---|
| 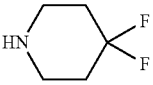 | 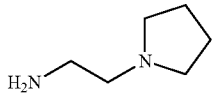<br>6a | 50 | 12 | 150 |
| 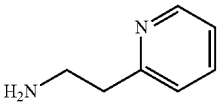 | 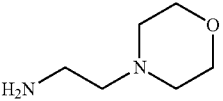<br>6b | 67 | 12 | 50 |
| | 6c | 72 | 8 | 150 |
| | 6d | 65 | 6 | 80 |

TABLE 1-continued

Structures, reaction conditions, yields, and melting points for carbamate analogs of melampomagnolide B

| Amine | Product | Yield (%) | Time (h) | Mp (° C.) |
|---|---|---|---|---|
| (structure) | 6e | 70 | 8 | 107 |
| (structure) | 6f | 75 | 5 | 70 |
| (structure) | 6g | 68 | 8 | 60 |

The above carbamate analogs were evaluated for growth inhibition properties against a panel of 60 human cancer cell lines derived from nine human cancer cell types, grouped into disease sub-panels that represent leukemia, lung, colon, central nervous system (CNS), melanoma, renal, ovary, breast, and prostate cancer cells. Growth inhibitory ($GI_{50}$) effects were measured as a function of the variation of optical density as a percentage of control.[16,17] Initial screening assays were carried out at a single concentration of 10 µM. Five analogs, 6a-6e, were identified as hits based on their ability to inhibit by 60% the growth of at least 8 of the 60 tumor cell lines in the panel. These five analogs were then evaluated in 5-dose assays over the concentration range $10^4$-$10^8$ µM, and their $GI_{50}$ values against the tumor cell lines in the panel determined (Table 2). Two analogs, 6a and 6e, were identified as lead compounds and generally exhibited improved growth inhibition against all human tumor cell lines when compared to PTL (1) and DMAPT (2), with the exception of the leukemia cell line subpanel; in these cell lines, the $GI_{50}$ values for DMAPT compared very favorably with those for both 6a and 6e. Compound 6a exhibited potency against leukemia cell line CCRF-CEM, melanoma cell line MDA-MB-435 and breast cancer cell line MDA-MB-468 in the nanomolar range with $GI_{50}$ values of 680, 460 and 570 nM, respectively. Compound 6e was found to possess potent anti-leukemic activity against leukemia cell line CCRF-CEM, non-small cell lung cancer cell line HOP-92 and renal cancer cell line RXF 393 with $GI_{50}$ values of 620, 650 and 900 nM, respectively, (Table 2).

Compounds 6a and 6e also exhibited significant growth inhibition against the following sub-panels of human cancer cell lines: non-small cell lung cancer ($GI_{50}$ values 0.65-1.45 µM); colon cancer ($GI_{50}$ values 1.12-2.06 µM); melanoma ($GI_{50}$ values 0.46-2.84 µM); renal cancer ($GI_{50}$ values 0.90-2.60 µM); and breast cancer ($GI_{50}$ values 0.57-3.07 µM) (Table 2).

We have determined the hydrolytic stability of the above five carbamate derivatives in human plasma and have shown that compounds 6b-6e have half-lives in the range 100-180 min, while compound 6a has a much longer half-life of 8 h in human plasma. Thus, we consider compounds 6b-6d to be anticancer agents that are also metabolized by plasma esterases to the active parent compound MMB, while compound 6a would be considered a more potent anticancer agent than MMB that is likely not metabolized to MMB in vivo.

The above results are interesting for a number of reasons: first, the antileukemic activities of 6a and 6e against the sub-panel of human leukemia cells indicates that these carbamate analogs of MMB are more potent than the parent compound. Second, the potent growth inhibition of human solid tumor cell lines by 6a and 6e is the first report of such activities for MMB analogs.

Third, these interesting results indicate that structural modification of the MMB molecule through appropriate carbamoylation of the primary hydroxyl group can lead to an improvement in the anticancer properties of MMB.

Figure 9:
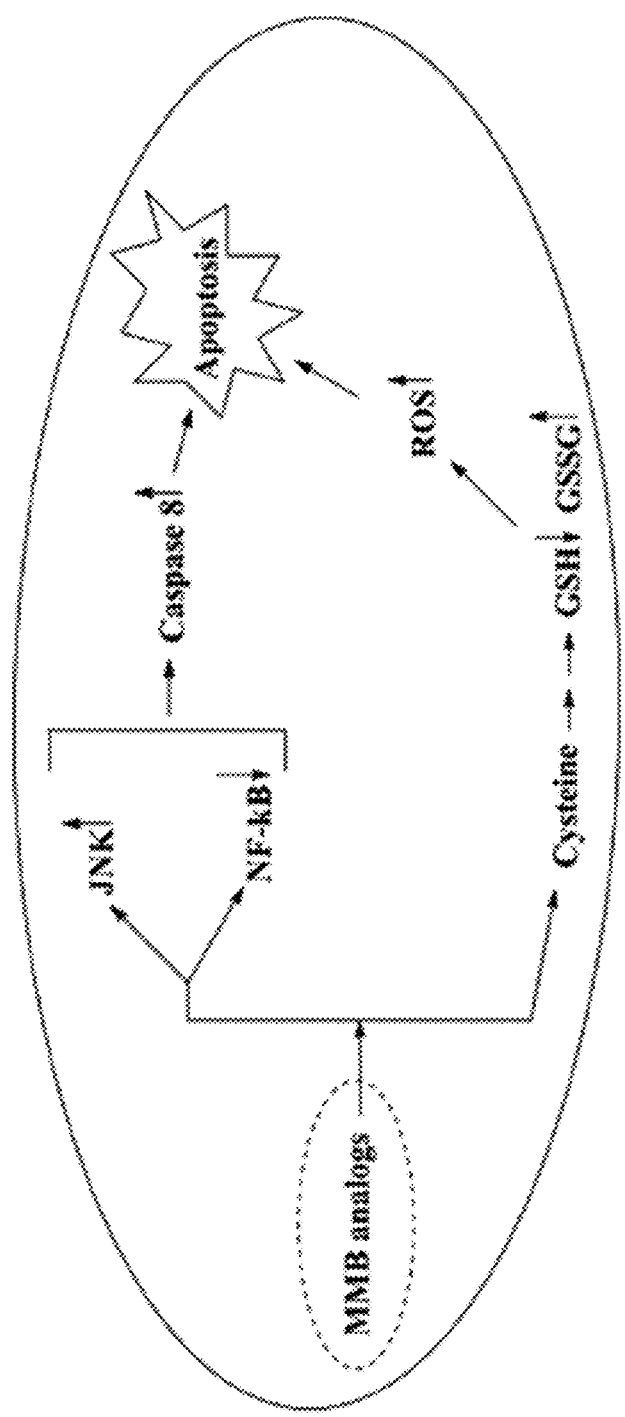
FIG. 9 shows the cytotoxic mechanism of action of MMB analogs.

The above MMB analogs, like PTL and DMAPT, are inhibitors of the NFκB pathway, activators of the nuclear kinase JNK, and selectively deplete glutathione levels in hematopoietic cancer stem cells, leading to an increase in reactive oxygen species (ROS) and subsequent apoptosis (FIG. 9).[4,8,11] We have recently shown that hematopoietic cancer stem cells have lower levels of reduced glutathione (GSH) and increased levels of oxidized glutathione (GSSG) when compared to normal stem cells, and are thus more vulnerable to agents such PTL and MMB and its analogs that induce oxidative stress through generation of ROS.[11] Specifically, PTL and MMB analogs inhibit several crucial enzymes in the glutathione pathway (i.e., GCLC and GPX1) leading to severe depletion of cellular glutathione and resulting in oxidative stress and apoptosis.

In summary, we have reported on a series of novel carbamate derivatives of MMB derived from heterocyclic and heteroaromatic amines. Among these derivatives, compounds 6a and 6e have been identified as potent anticancer agents with growth inhibition activities in the nanomolar range against a variety of hematological and solid tumor cell lines. Analogs 6a and 6e exhibit promising anti-leukemic activity against human leukemia cell line CCRF-CEM with $GI_{50}$ values of 680 and 620 nM, respectively. Compound 6a also exhibits $GI_{50}$ values of 460 and 570 nM against MDA-MB-435 melanoma and MDA-MB-468 breast cancer cell lines, respectively, and 6e has $GI_{50}$ values of 650 and 900 nM against HOP-92 non-small cell lung and RXF 393 renal cancer cell lines, respectively. Further structure-activity relationship studies will focus on the structural optimization of these interesting lead analogs and on the molecular basis for their mechanism of action.

TABLE 2

Growth inhibition ($GI_{50}$; μM)[b] data for PTL (1), DMAPT (2) and carbamoylated MMB analogs 6a-6e against a panel of human cancer cell lines

| Panel/cell line | 1a[a] $GI_{50}$ | 2a[a] $GI_{50}$ | 6a $GI_{50}$ | 6b $GI_{50}$ | 6c $GI_{50}$ | 6d $GI_{50}$ | 6e $GI_{50}$ |
|---|---|---|---|---|---|---|---|
| Leukemia | | | | | | | |
| CCRF-CEM | 7.94 | 1.99 | 0.68 | 2.49 | 2.65 | 3.03 | 0.62 |
| HL-60(TB) | 5.01 | 1.58 | 2.04 | 4.15 | ND | 3.59 | ND |
| K-562 | 19.9 | 2.51 | 3.45 | 3.26 | ND | 3.37 | ND |
| MOLT-4 | 15.8 | 3.16 | 2.05 | 3.48 | 5.54 | 5.00 | 2.32 |
| RPMI-8226 | 7.94 | 2.51 | 1.98 | 8.71 | 8.20 | 5.72 | 2.57 |
| SR | ND[c] | ND | 1.38 | 10.2 | 4.10 | 3.65 | 2.36 |
| Non-small cell lung cancer | | | | | | | |
| HOP-92 | 12.5 | 10.0 | 1.45 | 2.25 | 2.25 | 2.30 | 0.65 |
| NCI-H522 | 5.01 | 2.51 | 1.25 | 1.78 | 1.64 | 2.13 | 1.26 |
| Colon cancer | | | | | | | |
| COLO 205 | 15.8 | 31.6 | 2.06 | 4.78 | 3.54 | 8.89 | 1.79 |
| HCT-116 | 10.0 | 5.01 | 1.41 | 3.18 | 1.89 | 2.87 | 1.13 |
| SW-620 | 15.8 | 3.98 | 1.46 | 3.46 | 3.13 | 3.48 | 1.12 |
| CNS cancer | | | | | | | |
| SF-539 | 19.9 | 2.51 | 1.98 | 15.0 | 5.77 | 14.4 | 1.76 |
| SNB-75 | 50.1 | ND | 6.13 | 18.0 | 3.78 | 19.5 | 1.71 |
| Melanoma | | | | | | | |
| LOX IMVI | 7.94 | 10.0 | 2.23 | 7.88 | 4.96 | 4.84 | 1.95 |
| MALME-3M | 12.5 | ND | 1.90 | 4.18 | 7.52 | 6.12 | 2.32 |
| M14 | ND | 15.8 | 2.84 | 9.65 | 5.58 | 7.97 | 1.59 |
| MDA-MB-435 | ND | 7.94 | 0.46 | 6.56 | 6.01 | 5.89 | 2.24 |
| Ovarian cancer | | | | | | | |
| IGROV1 | 19.9 | 19.9 | 2.31 | 4.09 | 14.4 | 3.49 | 3.66 |
| OVCAR-3 | 19.9 | 12.5 | 1.69 | 8.41 | ND | 6.20 | ND |
| Renal cancer | | | | | | | |
| ACHN | ND | 15.8 | 1.79 | 3.80 | 2.75 | 3.74 | 1.75 |
| CAKI-1 | 10.0 | 12.5 | 2.03 | 6.86 | 2.88 | 4.31 | 1.99 |
| RXF 393 | 12.5 | 15.8 | 1.20 | 4.08 | 2.22 | 3.00 | 0.90 |
| TK-10 | ND | 3.16 | 2.60 | 3.11 | 3.78 | 3.93 | 2.51 |
| Prostate cancer | | | | | | | |
| DU-145 | ND | 5.01 | 2.44 | 7.42 | 4.59 | 3.74 | 3.49 |
| Breast cancer | | | | | | | |
| MCF7 | 15.8 | 5.01 | 1.62 | 3.91 | 2.85 | 3.54 | 1.33 |
| BT-549 | ND | 5.01 | 2.69 | 4.75 | 2.60 | 4.99 | 1.47 |
| T-47D | ND | 39.8 | 3.07 | 4.86 | 6.19 | 6.32 | 2.23 |
| MDA-MB-468 | ND | ND | 0.57 | 2.30 | 3.22 | 3.26 | 1.29 |

$GI_{50}$ values <1μm are bolded.
[a]$GI_{50}$ values obtained from NCI database.
[b]$GI_{50}$ concentration of analog (μM) that halves cellular growth.
[c]ND not determined References and Notes for Example 19

1. Knight, D. W. *Nat. Prod. Rep.* 1995, 12, 271.
2. (a) Skalska, J.; Brookes, P. S.; Nadtochiy, S. M.; Hilchey, S. P.; Jordan, C. T.; Guzman, M. L.; Maggirwar, S. B.; Briehl, M. M.; Bernstein, S. H. *PLoS ONE* 2009, 4, e8115; (b) Shama, N.; Crooks, P. A. *Bioorg. Med. Chem. Lett.* 2008, 18, 3870; (c) Hewamana, S.; Alghazal, S.; Lin, T. T.; Clement, M.; Jenkins, C.; Guzman, M. L.; Jordan, C. T.; Neelakantan, S.; Crooks, P. A.; Burnett, A. K.; Pratt, G.; Fegan, C.; Rowntree, C.; Brennan, P.; Pepper, C. *Blood* 2008, 111, 4681; (d) Oka, D.; Nishimura, K.; Shiba, M.; Nakai, Y.; Arai, Y.; Nakayama, M.; Takayama, H.; Inoue, H.; Okuyama, A.; Nonomura, N. *Int. J. Cancer* 2007, 120, 2576.
3. (a) Bork, P. M.; Schmitz, M. L.; Kuhnt, M.; Escher, C.; Heinrich, M. *FEBS Lett.* 1997, 402, 85; (b) Wen, J.; You, K. R.; Lee, S. Y.; Song, C. H.; Kim, D. G. *J. Biol. Chem.* 2002, 277, 38954; (c) Hehner, S. P.; Heinrich, M.; Bork, P. M.; Vogt, M.; Ratter, F.; Lehmann, V.; Schulze-Osthoff, K.; Dröge, W.; Schmitz, M. L. *J. Biol. Chem.* 1998, 273, 1288; (d) Sweeney, C. J.; Li, L.; Shanmugam, R.; Bhat-Nakshatri, P. B.; Jayaprakasan, V.; Baldridge, L. A.;

Gardner, T.; Smith, M.; Nakshatri, H.; Cheng, L. *Clin. Cancer Res.* 2004, 10, 5501; (e) Yip-Schneider, M. T.; Nakshatri, H.; Sweeney, C. J.; Marshall, M. S.; Wiebke, E. A.; Schmidt, C. M. *Mol. Cancer Ther.* 2005, 4, 587; (f) Nozaki, S.; Sledge, G. W.; Nakshatri, H. *Oncogene* 2001, 20, 2178.
4. Guzman, M. L.; Rossi, R. M.; Karnischky, L.; Li, X.; Peterson, D. R.; Howard, D. S.; Jordan, C. T. *Blood* 2005, 105, 4163.
5. (a) Guzman, M. L.; Jordan, C. T. *Expert Opin. Biol. Ther.* 2005, 5, 1147; (b) Dai, Y.; Guzman, M. L.; Chen, S.; Wang, L.; Yeung, S. K.; Pei, X. Y.; Dent, P.; Jordan, C. T.; Grant, S. *Br. J. Haematol.* 2010, 151, 70; (c) Kim, Y. R.; Eom, J. I.; Kim, S. J.; Jeung, H. K.; Cheong, J. W.; Kim, J. S.; Min, Y. H. *J. Pharmacol. Exp. Ther.* 2010, 335, 389.
6. Deschler, B.; Lubbert, M. *Cancer* 2006, 107, 2099.
7. (a) Estey, E.; Dohner, H. *Lancet* 2006, 368, 1894; (b) Lowenberg, B.; Suciu, S.; Archimbaud, E.; Haak, H.; Stryckmans, P.; De Cataldo, R.; Dekker, A. W.; Berneman, Z. N.; Thyss, A.; Van der Lelie, J.; Sonneveld, P.; Visani, G.; Fillet, G.; Hayat, M.; Hagemeijer, A.; Solbu, G.; Zittoun, R. *J. Clin. Oncol.* 1998, 16, 872; (c) Tazzari, P. L.; Cappellini, A.; Ricci, F.; Evangelisti, C.; Papa, V.; Grafone, T.; Martinelli, G.; Conte, R.; Cocco, L.; McCubrey, J. A.; Martelli, A. M. *Leukemia* 2007, 21, 427.
8. Pei, S.; Minhajuddin, M.; Callahan, K. P.; Balys, M.; Ashton, J. M.; Neering, S. J.; Lagadinou, E. D.; Corbett, C.; Ye, H.; Liesveld, J. L.; O'Dwyer, K. M.; Li, Z.; Shi, L.; Greninger, P.; Settleman, J.; Benes, C.; Hagen, F. K.; Munger, J.; Crooks, P. A.; Becker, M. W.; Jordan, C. T. *J. Biol. Chem.* 2013, 288, 33542.
9. El-Feraly, F. S. *Phytochemistry* 1984, 23, 2372.
10. Macias, F. A.; Galindo, J. C. G.; Massanet, G. M. *Phytochemistry* 1992, 31, 1969.
11. Shama, N.; ShanShan, P.; Fred, K. H.; Craig, T. J.; Peter, A. C. *Bioorg. Med. Chem.* 2011, 19, 1515.
12. Guzman, M. L.; Rossi, R. M.; Neelakantan, S.; Li, X.; Corbett, C. A.; Hassane, D. C.; Becker, M. W.; Bennett, J. M.; Sullivan, E.; Lachowicz, J. L.; Vaughan, A.; Sweeney, C. J.; Matthews, W.; Carroll, M.; Liesveld, J. L.; Crooks, P. A.; Jordan, C. T. *Blood* 2007, 110, 4427.
13. Synthetic procedure and analytical data for the p-nitrophenyloxycarbonyl ester of MMB (5): To the reaction mixture of MMB (100 mg, 0.378 mmol) and triethylamine (45.8 mg, 0.454 mmol) in dichloromethane (2 mL), p-nitrophenylchloroformate (76.3 mg, 0.378 mmol) was added at 0° C. The reaction mixture was stirred for 24 h at ambient temperature. When the reaction was completed (monitored by TLC), water was added to the reaction mixture and the aqueous mixture was extracted with dichloromethane. The organic layer was washed with water, followed by brine solution, dried over anhydrous Na2SO4 and concentrated to afford the crude product. The crude product was purified by column chromatography (silica gel, 2% methanol in dichloromethane) to afford compound 5 as a pale yellow solid. $^1$H NMR (CDCl3, 400 MHz): δ 8.26 (d, J=9.6 Hz, 2H), 7.37 (d, J=9.8 Hz, 2H), 6.25 (s, 1H), 5.83 (t, J=8.4 Hz, 1H), 5.56 (s, 1H), 4.81 (d, J=12.8 Hz, 1H), 4.72 (d, J=12.4 Hz, 1H), 3.86 (m, 1H), 2.85 (m, 2H), 2.56 (m, 7H), 1.77 (m, 2H), 1.55 (s, 1H), 1.16 (t, J=13.2 Hz, 1H). $^{13}$C NMR (CDCl3, 100 MHz): o 169.1, 155.2, 152.2, 145.4, 138.6, 133.6, 132.8, 125.3, 121.5, 120.3, 80.8, 71.5, 63.1, 59.8, 42.7, 36.4, 25.6, 24.9, 23.9, 17.9 ppm.
14. General synthetic procedure and analytical data for carbamate derivatives of MMB: To the p-nitrophenyloxycarbonyl ester derivative of MMB (5) (70 mg, 0.16 mmol) in dichloromethane (2 mL), the appropriate amine (0.16 mmol) was added at 0° C. The reaction mixture was stirred for 18 h at ambient temperature. When the reaction was completed (monitored by TLC), water was added to the reaction mixture and the aqueous mixture was extracted with dichloromethane. The organic layer was washed with water, followed by brine solution, dried over anhydrous Na$_2$SO$_4$ and concentrated to afford the crude product. The crude product was purified by column chromatography (silica gel, 5% methanol in dichloromethane) to afford the carbamate analogs (6a-g) as white solids. ((1aR,7aS,10aS,10bS,E)-1a-methyl-8-methylene-9-oxo-1a,2,3,6,7,7a,8,9,10a,10b-decahydrooxireno[2',3':9,10] cyclodeca[1,2-b]furan-5-yl)methyl-4,4-difluoropiperidine-1-carboxylate (6a): $^1$H NMR (CDCl$_3$), 400 MHz): o 6.27 (d, J=2.8 Hz, 1H), 5.67 (t, J=8.4 Hz, 1H), 5.56 (s, 1H), 4.69 (d, J=12.4 Hz, 1H), 4.52 (d, J=12 Hz, 1H), 3.87 (t, J=9.6 Hz, 1H), 3.60 (br s, 4H), 2.87 (d, J=9.2 Hz, 2H), 2.50-2.16 (m, 6H), 1.96 (br s, 4H), 1.71 (t, J=10 Hz, 1H), 1.55 (s, 3H), 1.14 (t, J=12 Hz, 1H). $^{13}$C NMR (CDCl3, 100 MHz): o 169.4, 154.8, 138.7, 135.3, 129.9, 121.5, 120.5 (t, JCF=5.3 Hz, 1C), 81.1, 67.7, 63.4, 60.0, 42.7, 41.0, 36.7, 34.0, 25.8, 24.4, 23.9, 18.1 ppm. HRMS (ESI) m/z calcd for C$_{21}$H$_{28}$F$_2$NO$_5$ (M+H)$^+$ 412.1930, found 412.1933. ((1aR,7aS,10aS,10bS,E)-1a-methyl-8-methylene-9-oxo-1a,2,3,6,7,7a,8,9,10a,10b-decahydrooxireno [2',3':9,10]cyclodeca[1,2-b]furan-5-yl)methyl-(2-(pyrrolidin-1-yl)ethyl)carbamate (6b): $^1$H NMR (CDCl3, 400 MHz): o 6.22 (d, J=3.2 Hz, 1H), 5.65 (t, J=7 Hz, 1H), 5.55 (s, 1H), 4.62 (d, J=11.6 Hz, 1H), 4.47 (d, J=12.4 Hz, 1H), 3.82 (t, J=9.6 Hz, 1H), 3.35 (s, 2H), 2.90-2.83 (m, 2H), 2.70 (s, 4H), 2.42 (d, J=9.6 Hz, 2H), 2.38-2.13 (m, 7H) 1.84 (s, 4H), 1.66 (t, J=12 Hz, 1H), 1.52 (s, 3H), 1.13 (t, J=11.6 Hz, 1H). $^{13}$C NMR (CDCl$_3$, 100 MHz): δ 169.3, 156.1, 138.6, 135.3, 129.8, 120.1, 80.9, 67.0, 63.1, 59.8, 55.1, 53.8, 42.5, 38.9, 36.5, 25.6, 24.3, 23.6, 23.2, 17.8 ppm. HRMS (ESI) m/z calcd for C$_{22}$H$_{33}$N$_2$O$_5$ (M+H)$^+$ 405.2384, found 405.2390. ((1aR,7aS,10aS,10bS,E)-1a-methyl-8-methylene-9-oxo-1a,2,3,6,7,7a,8,9,10a,10b-decahydrooxireno[2',3':9,10]cyclodeca[1,2-b]furan-5-yl) methyl-(2-(pyridin-2-yl)ethyl)carbamate (6c): $^1$H NMR (CDCl$_3$, 400 MHz): δ 8.50 (s, 1H), 7.62 (t, J=7.2 Hz, 1H), 7.15 (d, J=7.6 Hz, 2H), 6.19 (s, 1H), 5.64 (t, J=8 Hz, 1H), 5.56-5.56 (m, 2H), 4.62 (d, J=12.4 Hz, 1H), 4.44 (d, J=12.8 Hz, 1H), 3.84 (t, J=9.2 Hz, 1H), 3.60 (d, J=6 Hz, 2H), 2.99-2.82 (m, 4H), 2.41-2.12 (m, 5H), 1.75 (s, 1H), 1.64 (d, J=10.4 Hz, 1H), 1.52 (s, 3H), 1.07 (t, J=13.6 Hz, 1H). $^{13}$C NMR (CDCl3, 100 MHz): o 169.3, 159.1, 156.0, 149.1, 138.6, 136.6, 135.5, 129.9, 123.4, 121.6, 120.2, 81.0, 67.0, 63.2, 59.8, 42.5, 40.1, 37.1, 36.6, 25.8, 24.4, 23.7, 17.9 ppm. HRMS (ESI) m/z calcd for C$_{23}$H$_{29}$N$_2$O$_5$ (M+H)$^+$ 413.2071, found 413.2073. ((1aR,7aS,10aS, 10bS,E)-1a-methyl-8-methylene-9-oxo-1a,2,3,6,7,7a,8,9, 10a,10b-decahydrooxireno[2',3':9,10]-cyclodeca[1,2-b] furan-5-yl)-methyl(2-morpholino ethyl)carbamate (6d): $^1$H NMR (CDCl$_3$, 400 MHz): δ 6.11 (d, J=3.6 Hz, 1H), 5.58 (t, J=8 Hz, 1H), 5.43 (d, J=2.8 Hz, 1H), 5.06 (s, 1H), 4.53 (d, J=12.4 Hz, 1H), 4.34 (d, J=12 Hz, 1H), 3.74 (t, J=8.8 Hz, 1H), 3.56 (s, 4H), 3.16 (t, J=5.2 Hz, 2H), 2.78-2.72 (m, 2H), 2.32 (s, 8H), 2.21-2.00 (m, 4H), 1.55 (t, J=10.4 Hz, 1H), 1.41 (s, 3H), 1.01 (t, J=12 Hz, 1H). $^{13}$C NMR (CDCl3, 100 MHz): δ 169.2, 155.9, 138.7, 135.4, 130.2, 120.0, 80.9, 67.0, 66.7, 63.1, 59.8, 57.2, 53.1, 42.5, 37.0, 36.5, 25.7, 24.4, 23.7, 17.8 ppm. HRMS (ESI) m/z calcd for C$_{22}$H$_{33}$N$_2$O$_6$ (M+H)$^+$ 421.2333, found 421.2331. ((1aR,7aS,10aS,10bS,E)-1a-methyl-8-methylene-9-oxo-1a,2,3,6,7,7a,8,9,10a,10b-decahydrooxireno

[2',3':9,10]cyclodeca[1,2-b]furan-5-yl)methyl-(5-(methylthio)-1H-1,2,4-triazol-3-yl)carbamate (6e): $^1$H NMR (CDCl3, 400 MHz): δ 6.22 (s, 2H), 5.82 (t, J=8 Hz, 1H), 5.50 (s, 1H), 4.90 (d, J=12.4 Hz, 1H), 4.81 (d, J=12.4 Hz, 1H), 3.85 (t, J=9.6 Hz, 1H), 2.95 (s, 1H), 2.85 (d, J=9.2 Hz, 1H), 2.48-2.15 (m, 8H), 1.70-1.53 (m, 6H), 1.13 (t, J=12.4 Hz, 1H) ppm. $^{13}$C NMR (CDCl3, 100 MHz): δ 169.1, 163.1, 157.4, 149.9, 138.5, 133.3, 132.7, 120.2, 80.7, 70.1, 62.9, 59.7, 42.4, 36.2, 25.6, 24.3, 23.7, 17.8, 13.5 ppm. HRMS (ESI) m/z calcd for $C_{19}H_{25}N_4O_5S$ (M+H)$^+$ 421.1540, found 421.1524. ((1aR,7aS,10aS,10bS,E)-1a-methyl-8-methylene-9-oxo-1a,2,3,6,7,7a,8,9,10a,10b-decahydrooxireno[2',3':9,10]cyclodeca[1,2-b]furan-5-yl)methyl-(3-(1H-imidazol-1-yl)-propyl)carbamate (6f): $^1$H NMR (CDCl$_3$, 400 MHz): δ 7.56 (s, 1H), 7.09 (s, 1H), 6.95 (s, 1H), 6.26 (d, J=3.6 Hz, 1H), 5.69 (t, J=8 Hz, 1H), 5.56 (d, J=3.2 Hz, 1H), 4.85 (s, 1H), 4.64 (d, J=12.4 Hz, 1H), 4.51 (d, J=12.4 Hz, 1H), 4.04 (t, J=7.2 Hz, 2H), 3.88 (t, J=9.2 Hz, 1H), 3.21 (d, J=6 Hz, 2H), 2.93-2.85 (m, 2H), 2.47-2.16 (m, 7H), 2.03 (t, J=6.4 Hz, 1H) 1.70 (t, J=10.8 Hz, 1H), 1.55 (s, 3H), 1.15 (t, J=12.4 Hz, 1H). $^{13}$C NMR (CDCl3, 100 MHz): δ 169.5, 156.3, 138.9, 137.1, 135.3, 130.4, 129.6, 120.2, 118.8, 81.1, 67.3, 63.3, 60.0, 44.4, 42.7, 38.3, 36.7, 31.5, 25.8, 24.6, 23.8, 18.0 ppm. HRMS (ESI) m/z calcd for $C_{22}H_{30}N_3O_5$ (M+H)$^+$ 416.2180, found 416.2183. ((1aR,7aS,10aS,10bS,E)-1a-methyl-8-methylene-9-oxo-1a,2,3,6,7,7a,8,9,10a,10b-decahydrooxireno[2',3':9,10]-cyclodeca[1,2-b]furan-5-yl)methyl-(3-morpholinopropyl)carbamate (6g) $^1$H NMR (CDCl3, 400 MHz): δ 6.23 (s, 1H), 5.74 (s, 1H), 5.65 (t, J=8 Hz, 1H), 5.54 (s, 1H), 4.58 (d, J=12 Hz, 1H), 4.48 (d, J=16 Hz, 1H), 3.85 (t, J=9.2 Hz, 1H), 3.72 (s, 4H), 3.27 (s, 2H), 2.89-2.83 (m, 2H), 2.46-2.11 (m, 12H), 1.69 (t, J=12 Hz 3H), 1.52 (s, 3H), 1.11 (t, J=12 Hz, 1H). $^{13}$C NMR (CDCl$_3$, 100 MHz): δ 169.5, 156.3, 138.9, 135.7, 129.9, 120.4, 81.2, 67.0, 66.9, 63.4, 60.1, 57.4, 53.6, 42.7, 36.8, 25.9, 25.5, 24.6, 23.9, 18.1 ppm. HRMS (ESI) m/z calcd for $C_{23}H_{35}N_2O_6$ (M+H)$^+$ 435.2490, found 435.2482.

15. Neelakantan, S.; Shama, N.; Guzman, M. L.; Jordan, C. T.; Crooks, P. A. *Bioorg. Med. Chem. Lett.* 2009, 19, 4346.
16. Boyd, M. R.; Paull, K. D. *Drug Dev. Res.* 1995, 34, 91.
17. Acton, E. M.; Narayanan, V. L.; Risbood, P. A.; Shoemaker, R. H.; Vistica, D. T.; Boyd, M. R. *J. Med. Chem.* 1994, 37, 2185.

Example 20

Efficacy of Ester and Amide Derivates of MMB Against Leukemia Cell Lines

Figure 12:
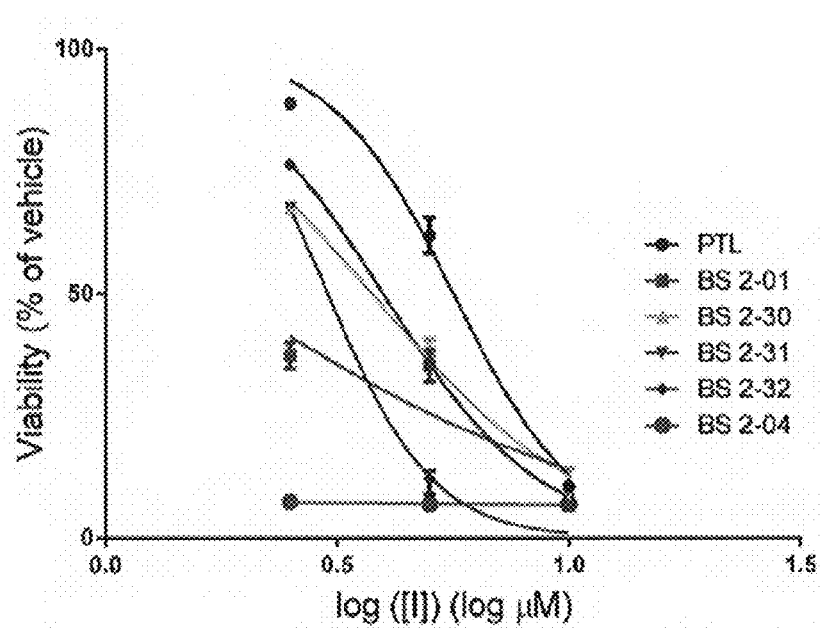
FIG. 12 shows a graph demonstrating the percentage of live cells relative to untreated cells after 24 hour-treatment with the compounds. Cells are M9 cells.
Figure 13:
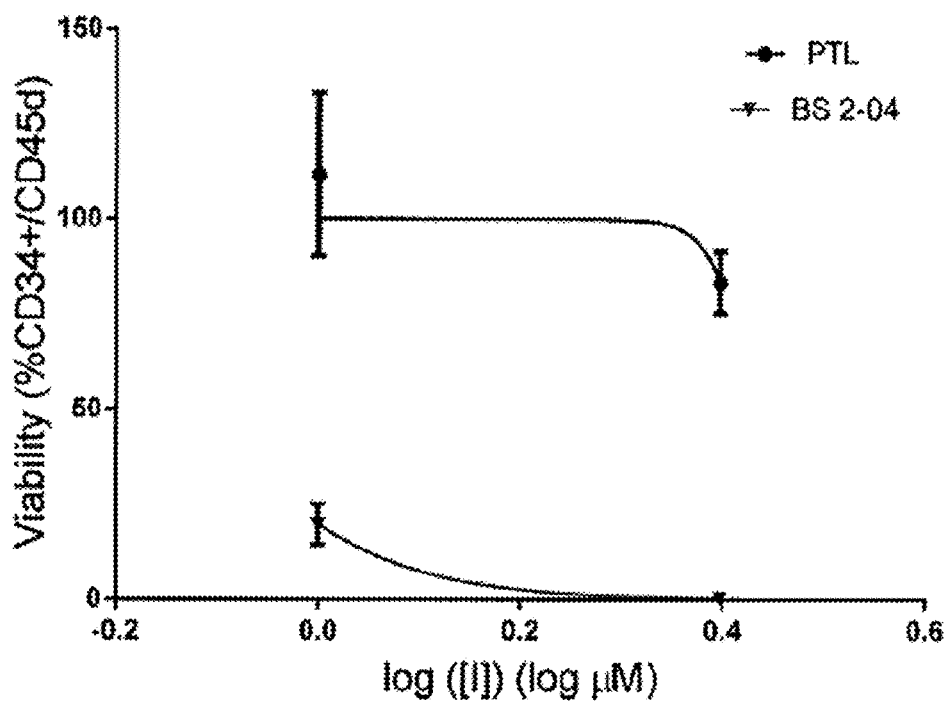
FIG. 13 shows a graph demonstrating the toxicity of PTL and BS-2-04 against cord blood cells. BS-2-04 has an $EC_{50}$ of 0.72 µM in M9 cells and an $EC_{50}$ of 0.75 µM in cord blood cells. SI=1.04
Figure 14:
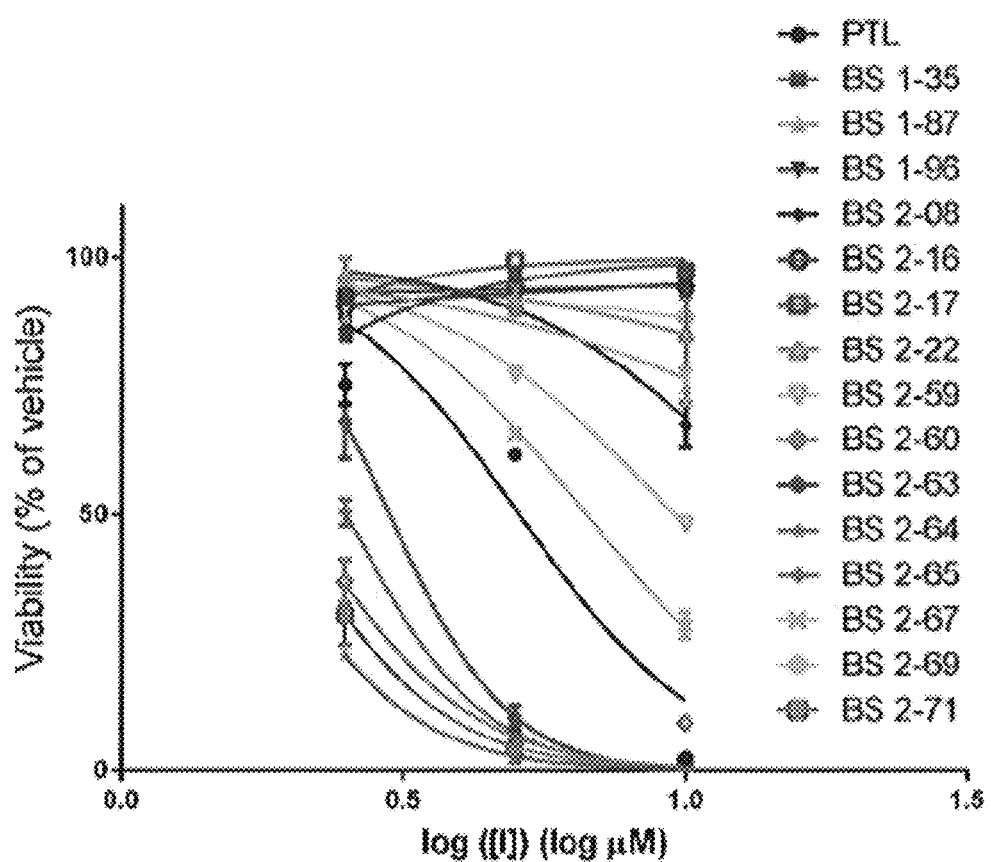
FIG. 14 shows a graph demonstrating the percentage of live cells relative to untreated cells after 24 hour-treatment with the compounds. Cells are M9 cells.
Figure 15:
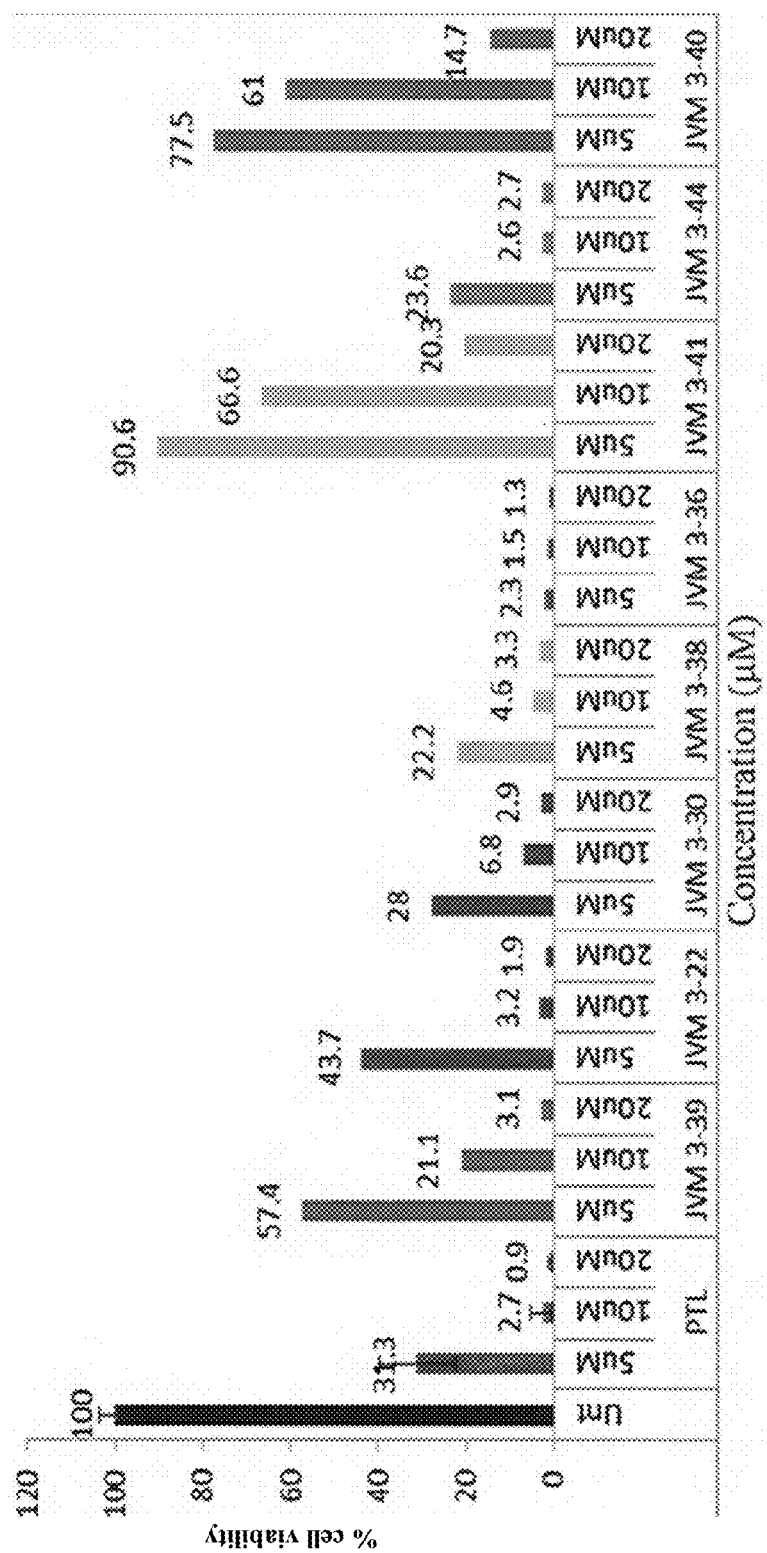
FIG. 15 shows a graph demonstrating the cytotoxic activity of MMB ester conjugates against M9 cell lines.
Figure 16:
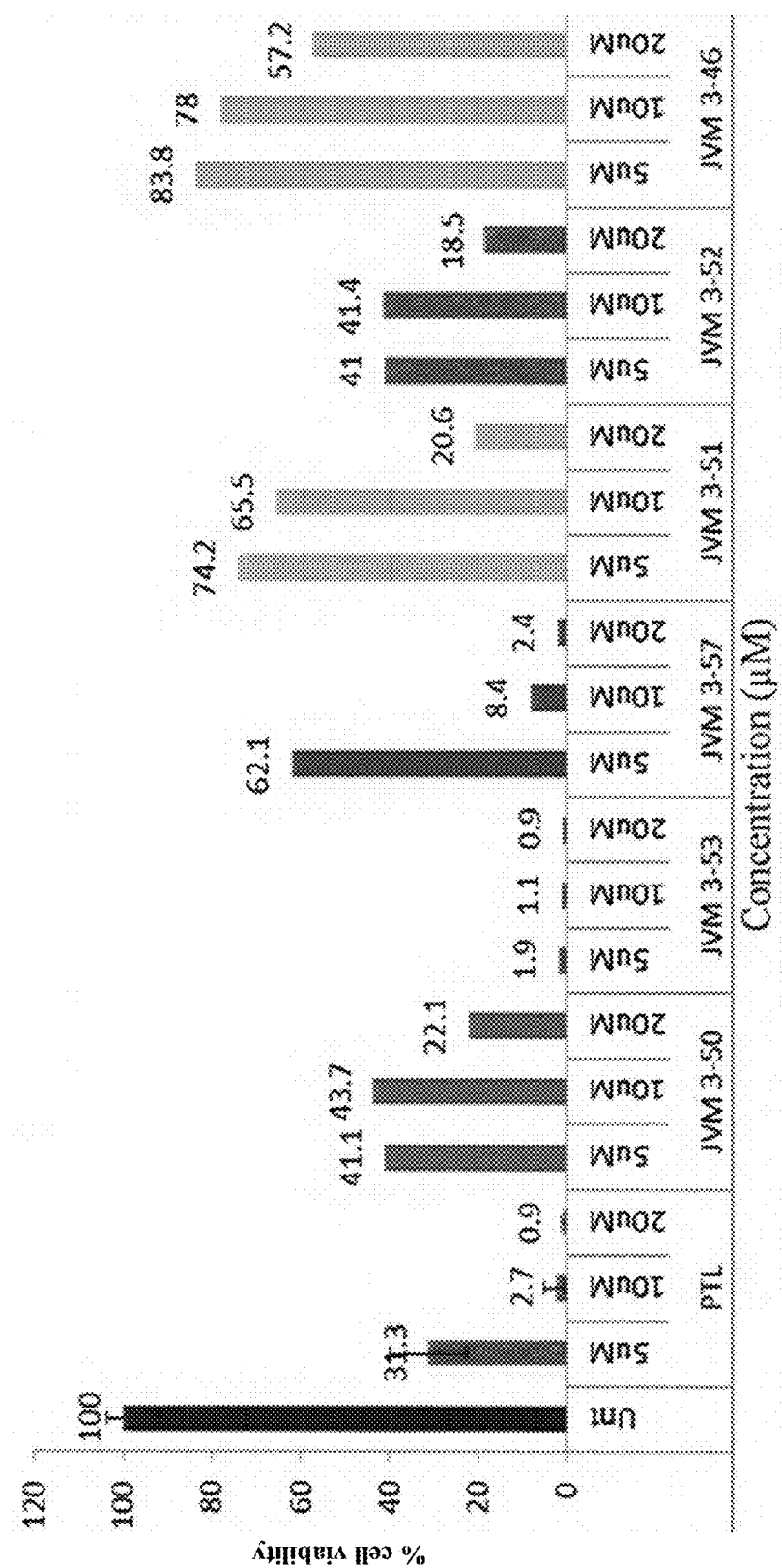
FIG. 16 shows a graph demonstrating the cytotoxic activity of MMB amide conjugates against M9 cell lines.
Figure 17A:
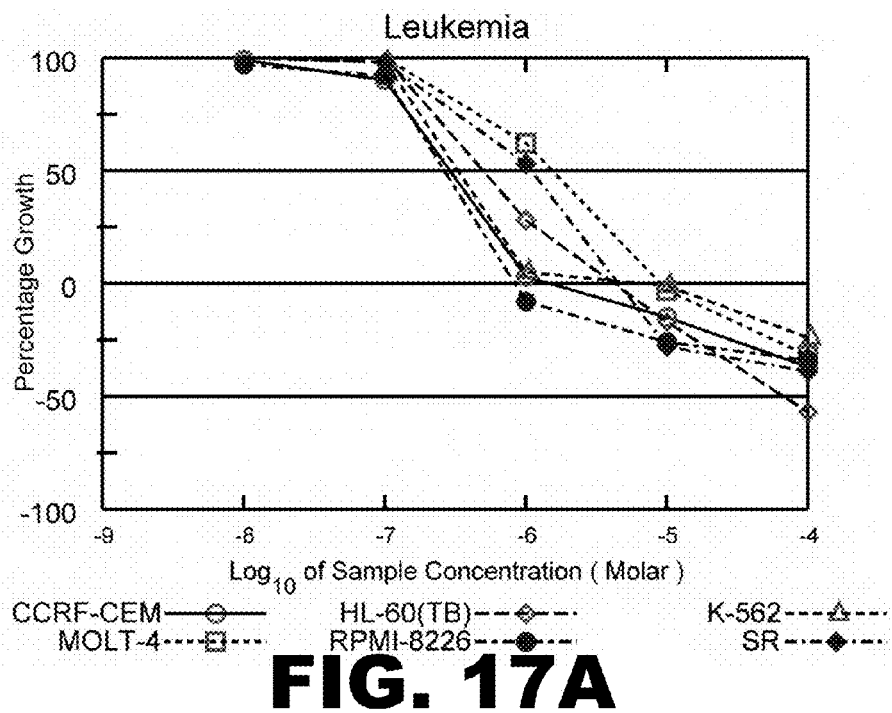
FIG. 17A-I shows graphs demonstrating the five dose test results of BS-1-28 against human cancer cell lines.
Figure 17B:
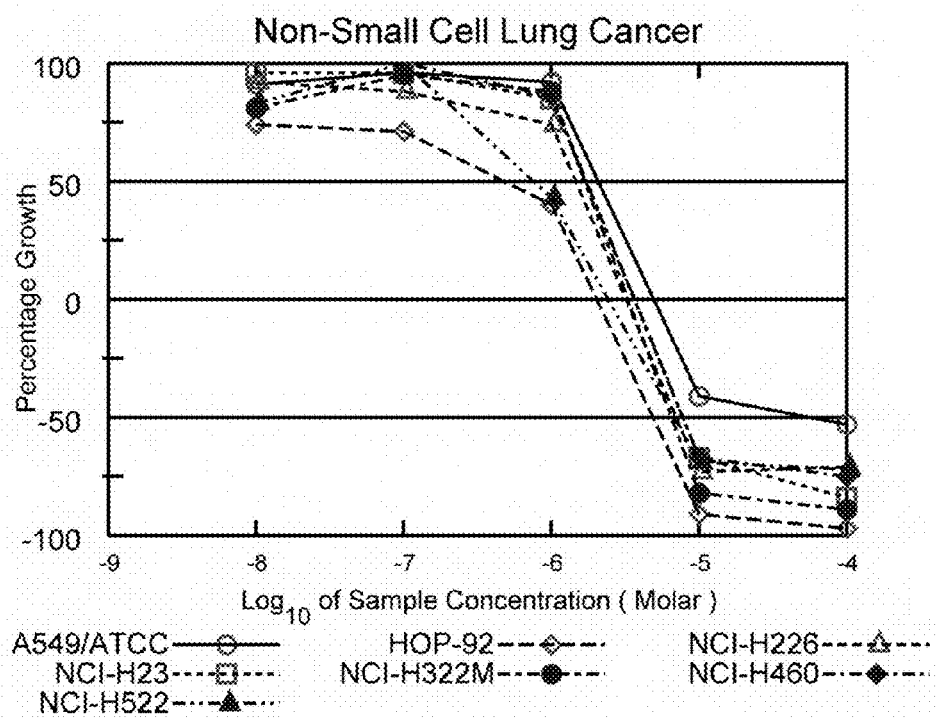
Figure 17C:
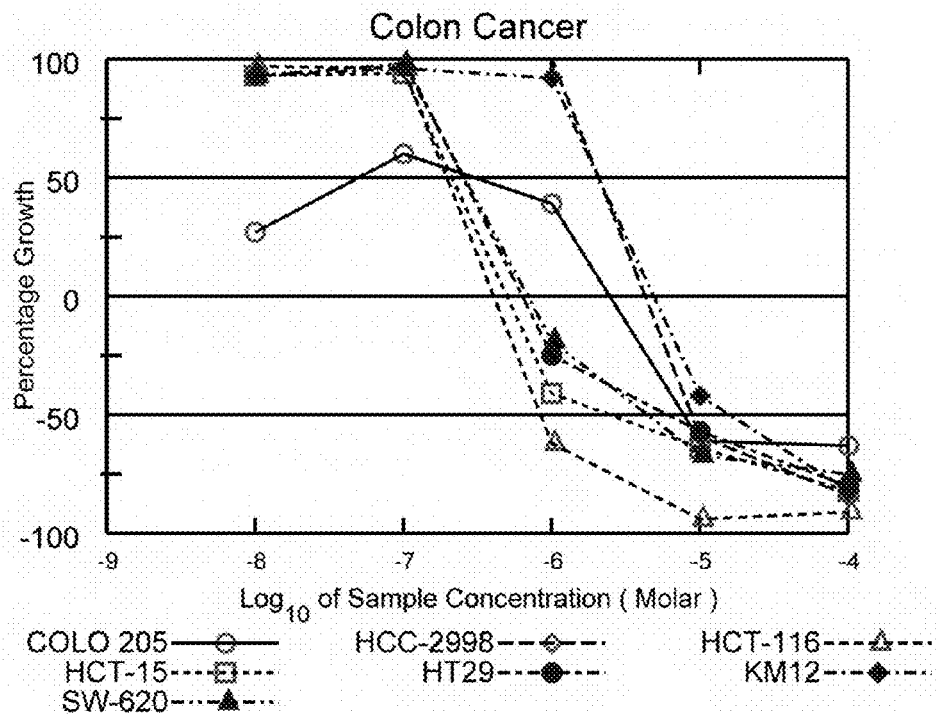
Figure 17D:
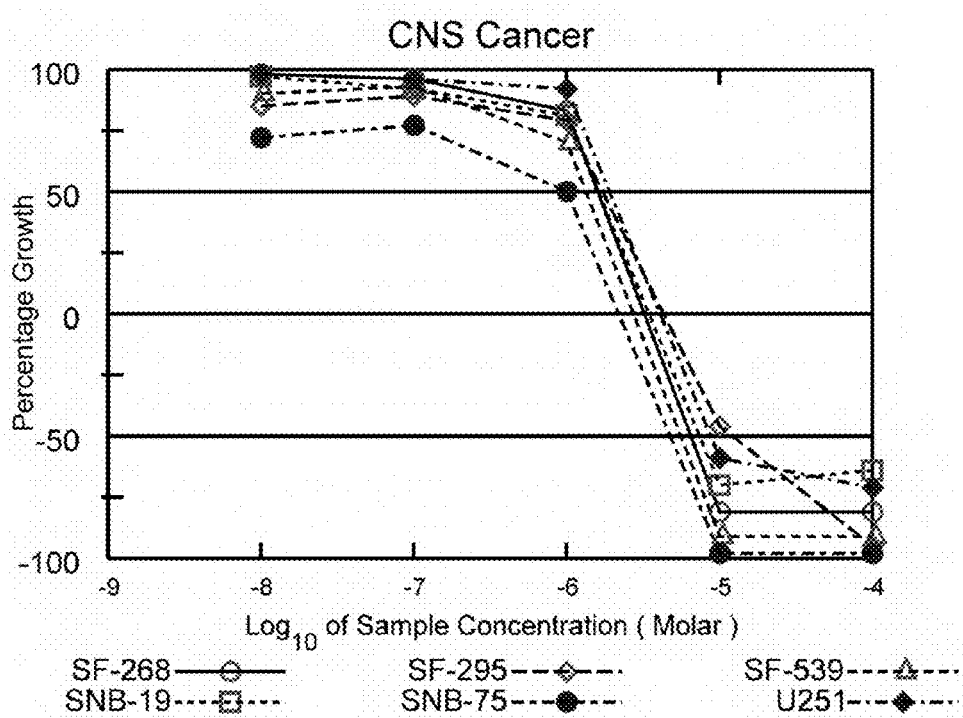
Figure 17E:
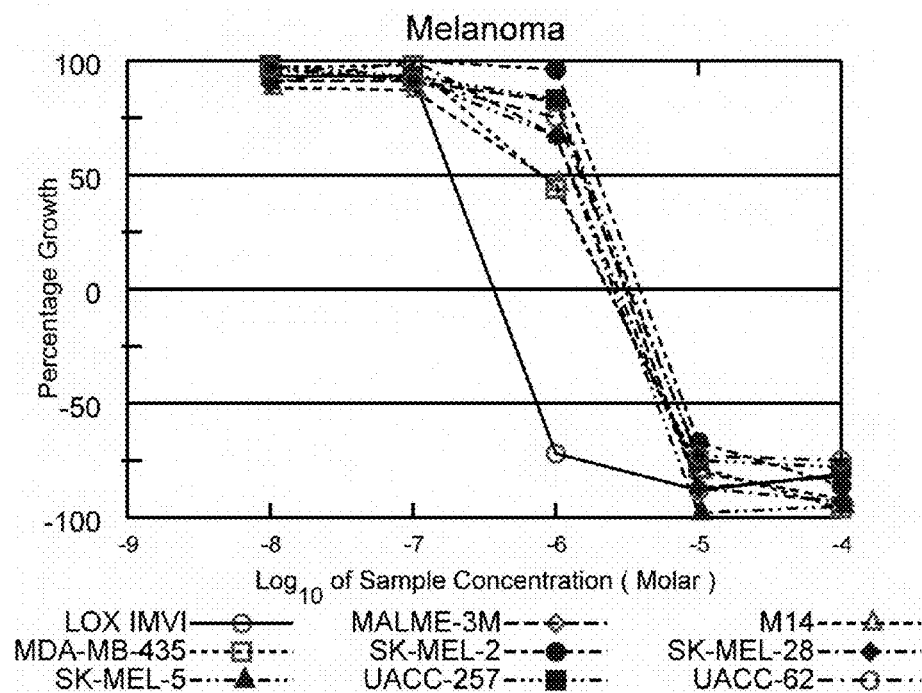
Figure 17F:
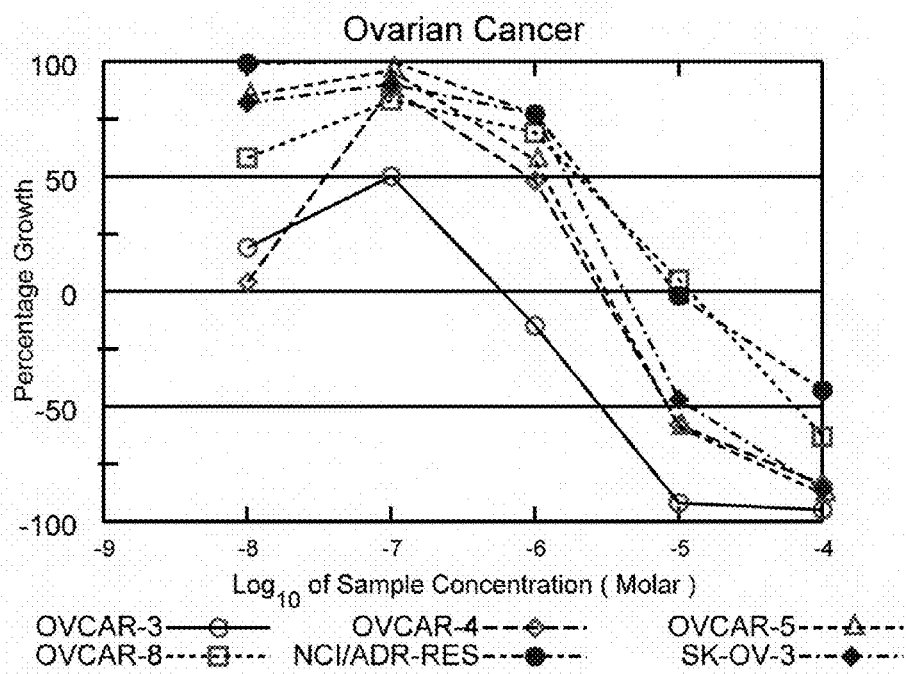
Figure 17G:
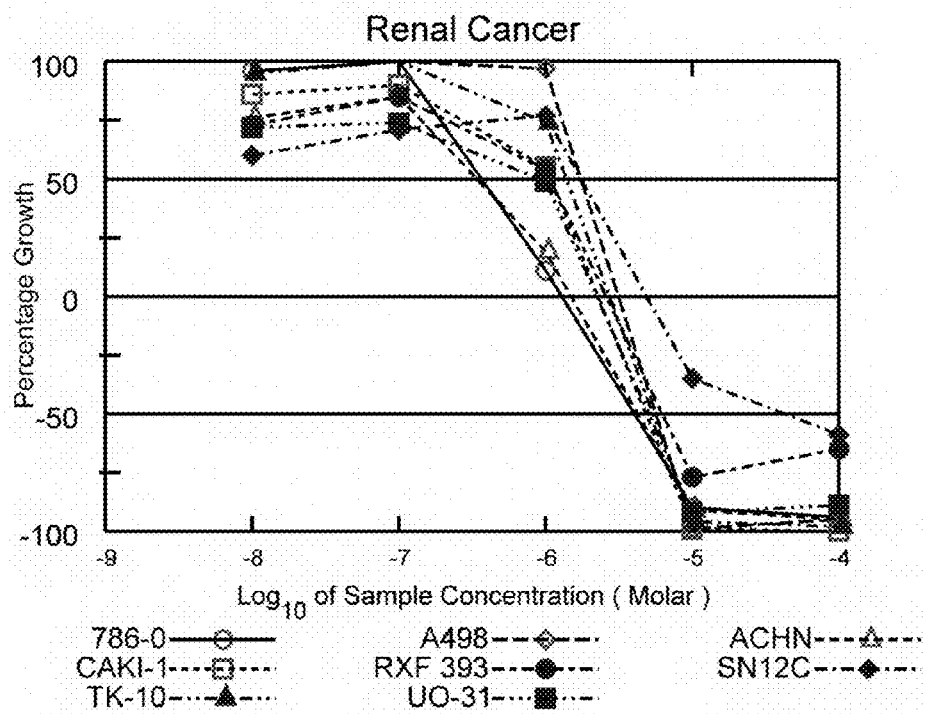
Figure 17H:
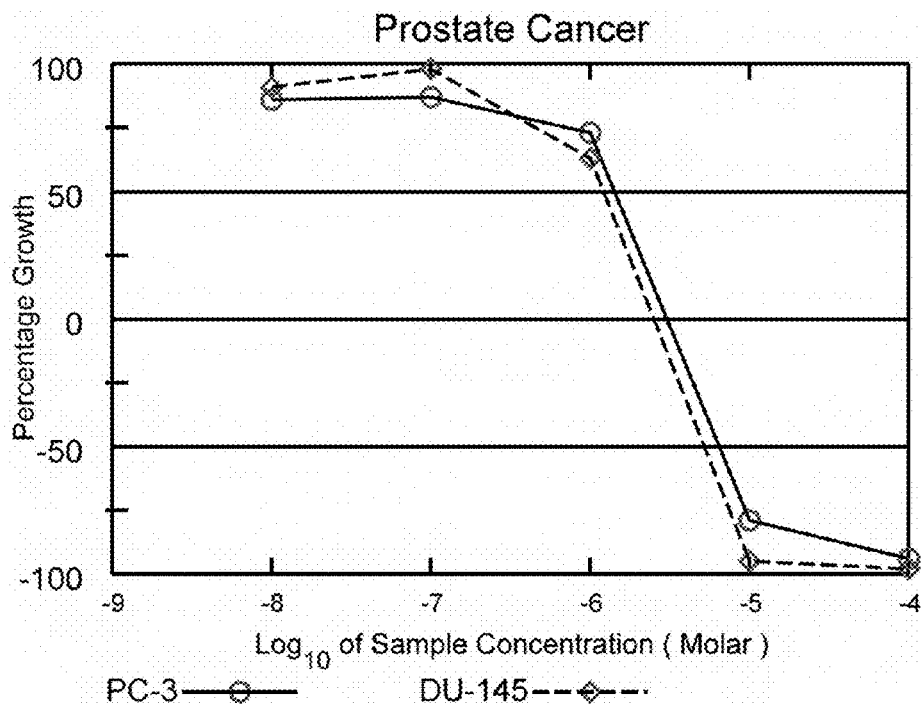
Figure 17I:
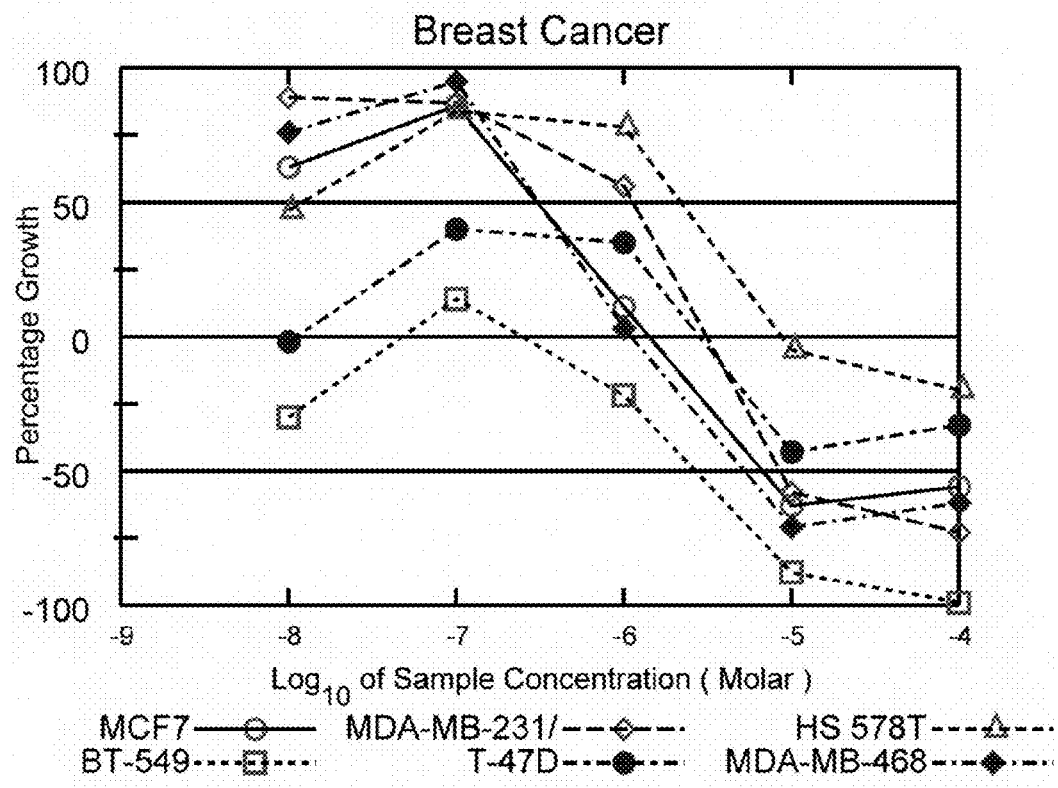

Ester and amide derivatives of melampomagnolide B were screened for anti-leukemic activity against M9ENL AML cell lines (FIG. 12; FIG. 14; FIG. 15; FIG. 16). For each compound, in vitro cell culture studies were performed in which a range of concentrations (0.25-20 μM) was tested for cytotoxicity against leukemia cell lines, primary leukemia specimens and normal bone marrow controls. Evaluations were performed generally after 24 hours of drug exposure using viability labeling with trypan blue dye, as well as flow cytometric labeling with Annexin V and propidium iodide to delineate dead cell populations. For all studies, native parthenolide (PTL) was included as a reference control. As expected, relative cytotoxicity varied considerably as a function of the specific structural modifications made to each molecule.

Compounds BS-1-28, BS-2-01, BS-2-05 and BS-2-31, BS-2-32 were the most active compounds against AML 052308 cells in culture and were more potent than the parent compound, MMB. BS-2-04 (the indole acryloic acid derivative of MMB) was the most active molecule with an EC$_{50}$ value of 0.72 μM, and was about 22-fold more cytotoxic than MMB (EC$_{50}$=16 μM); BS-2-04 was also 10-fold more potent than parthenolide (EC$_{50}$=7.6 μM). The analogs BS-1-28, BS-2-05, BS-2-31, and BS-2-32 exhibited around 3-fold more potency (EC$_{50}$=2.2, 2.5, 3.0, 4.0 μM) in comparison with parthenolide, and were around 7-fold more cytotoxic than MMB against AML 052308 cells. BS-1-98 showed almost equal cytotoxicity to the parent compound, MMB.

Compound BS-2-04 was screened for anti-leukemic activity against the M9 ENL cell line, and AML 123009 and AML 100510 primary isolates, and exhibited good anti-leukemic activity compared to parent compound MMB in these cellular assays. Moreover, other compounds consistently demonstrated greater cytotoxicity than PTL (FIG. 12; FIG. 14). The EC$_{50}$ values of certain compounds were consistently approximately 10-folder greater than PTL. EC$_{50}$ values of these compounds are 0.27 μM (BS-2-04), 2.2 μM (BS-2-01), 2.5 μM (BS-2-05), 3.0 μM (BS-2-31), 4.0 μM (BS-2-32), 2.9 μM (JVM 3-38) against M9ENL AML cell lines. EC$_{50}$ values of other compounds were: 11 μM (JVM 3-39), 4.7 μM (JVM 3-22), 3.3 μM (JVM 3-30), 11 μM (JVM 340), 2.9 μM (JVM 3-38), 1.7 μM (JVM 3-36), 13 μM (JVM 3-41) and 3.5 μM (JVM 3-44) against M9ENL AML cell lines. Amide derivatives of MMB afforded EC$_{50}$ values of 3.5 μM (JVM 3-50), 0.016 μM (JVM 3-53), 5.9 μM (JVM 3-57), 12 μM (JVM 3-51), 8.3 μM (JVM 3-52) and 28 μM (JVM 3-46). Compound JVM 3-53 exhibited almost 30-fold greater cytotoxicity than PTL, and compound JVM 3-36 was 3-fold more potent than PTL. The remaining compounds had activities similar to PTL (FIG. 15; FIG. 16).

Example 21

Efficacy of Amide and Ester Derivatives of MMB Against a Panel of 60 Human Tumor Cell Lines MMB analogs were also screened for anticancer activity against a panel of 60 human tumor cell lines. The compounds were first screened at a single concentration of 10$^{-5}$ M. Compounds which showed more than 60% growth inhibition in at least eight human cancer cell lines from the panel of sixty cell lines were selected for a complete dose-response study at five different concentrations of drug (10$^{-4}$ M, 10$^{-5}$ M, 10$^{-6}$ M, 10$^{-7}$ M and 10$^{-8}$ M). From the initial single dose screen, 5 compounds (BS-1-28, 2-01, 2-30, 2-65, 2-68) were selected for five dose screening. Compound BS-1-28 showed remarkable anticancer activity against melanoma, leukemia, colon, CNS, breast, ovarian, non-small cell lung, renal, and prostate cancers (FIG. 17A-I). Compound BS-1-28 was found to be a very potent analogue with GI$_{50}$ values <10 nM against BT-549 and T-467 D breast cancer cell lines, and this compound also exhibited potent nanomolar growth inhibition against CCRF-CEM, HL-60 (TB), K-562 and RPMI-8226 leukemia cell lines; HOP-92 and NCI-H522 non-small cell lung cancer cell lines; HCT-116, HCT-15 and SW-620 colon cancer cell lines; LOX IMVI, M14 and MDA-MB-435 melanoma cell lines; and 786-0, ACHN and UO-31 renal cancer cell lines (FIG. 17A-I). Five dose screening studies for other compounds are currently in progress.

Figure 19A:
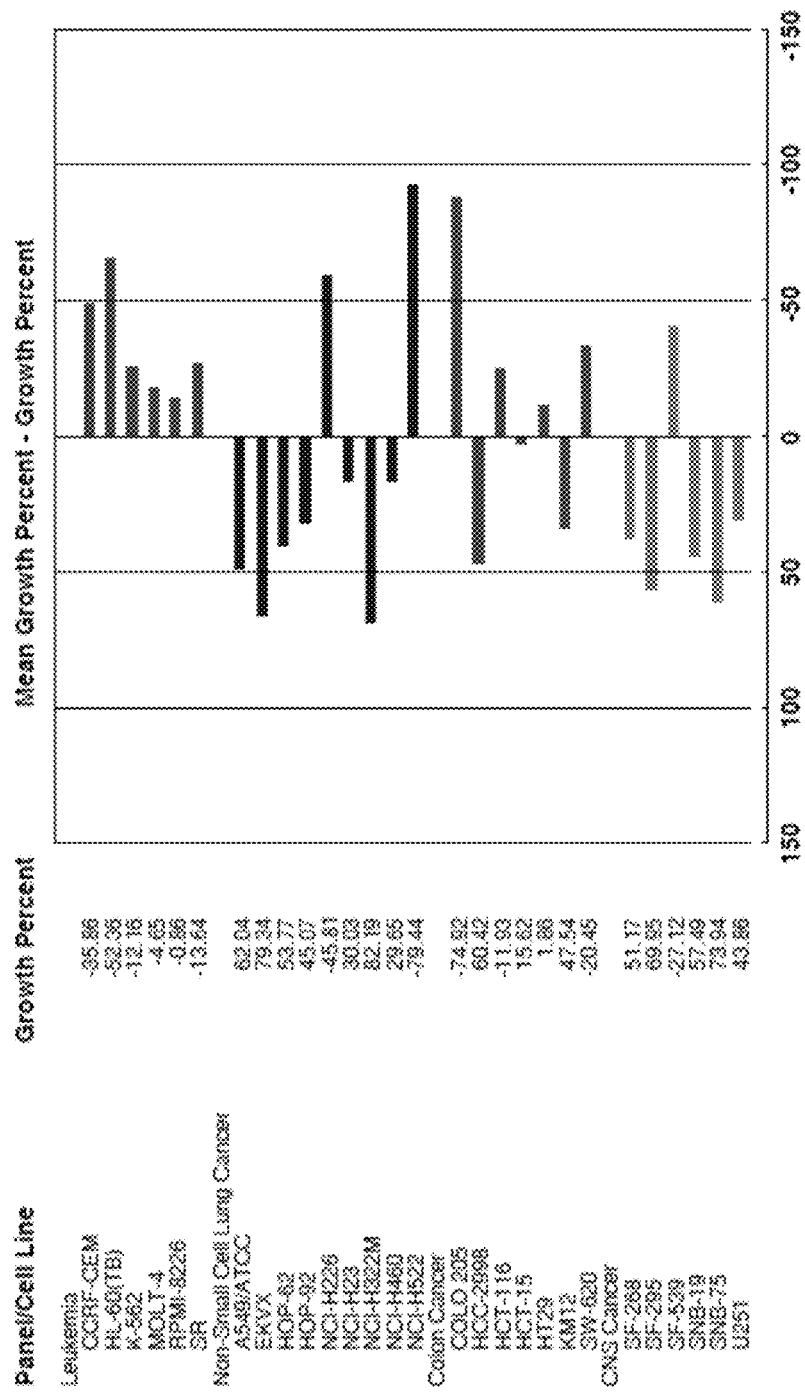
FIG. 19A-B shows NCI single dose results for compound JVM 4-14.
Figure 19B:
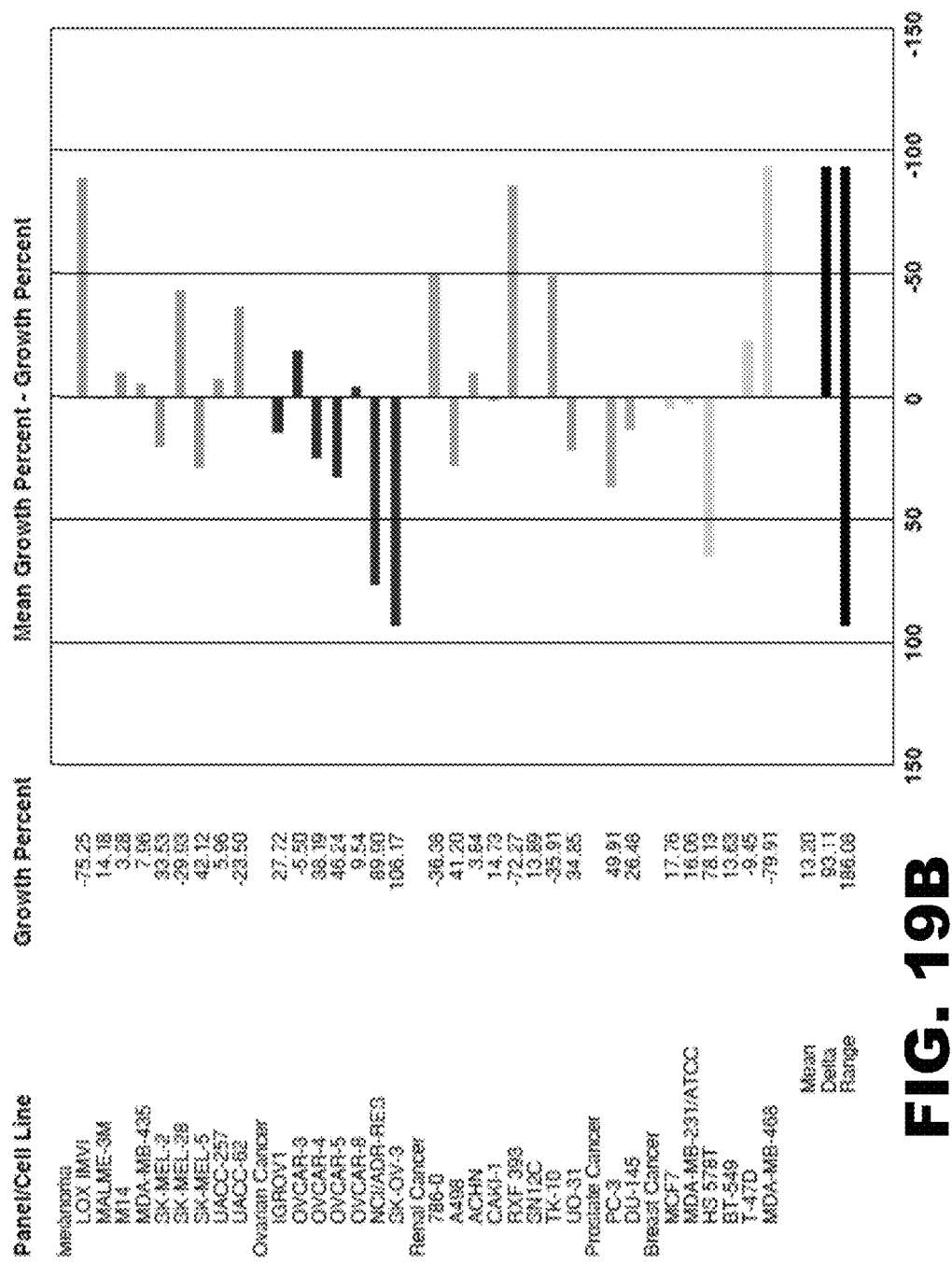
Figure 20A:
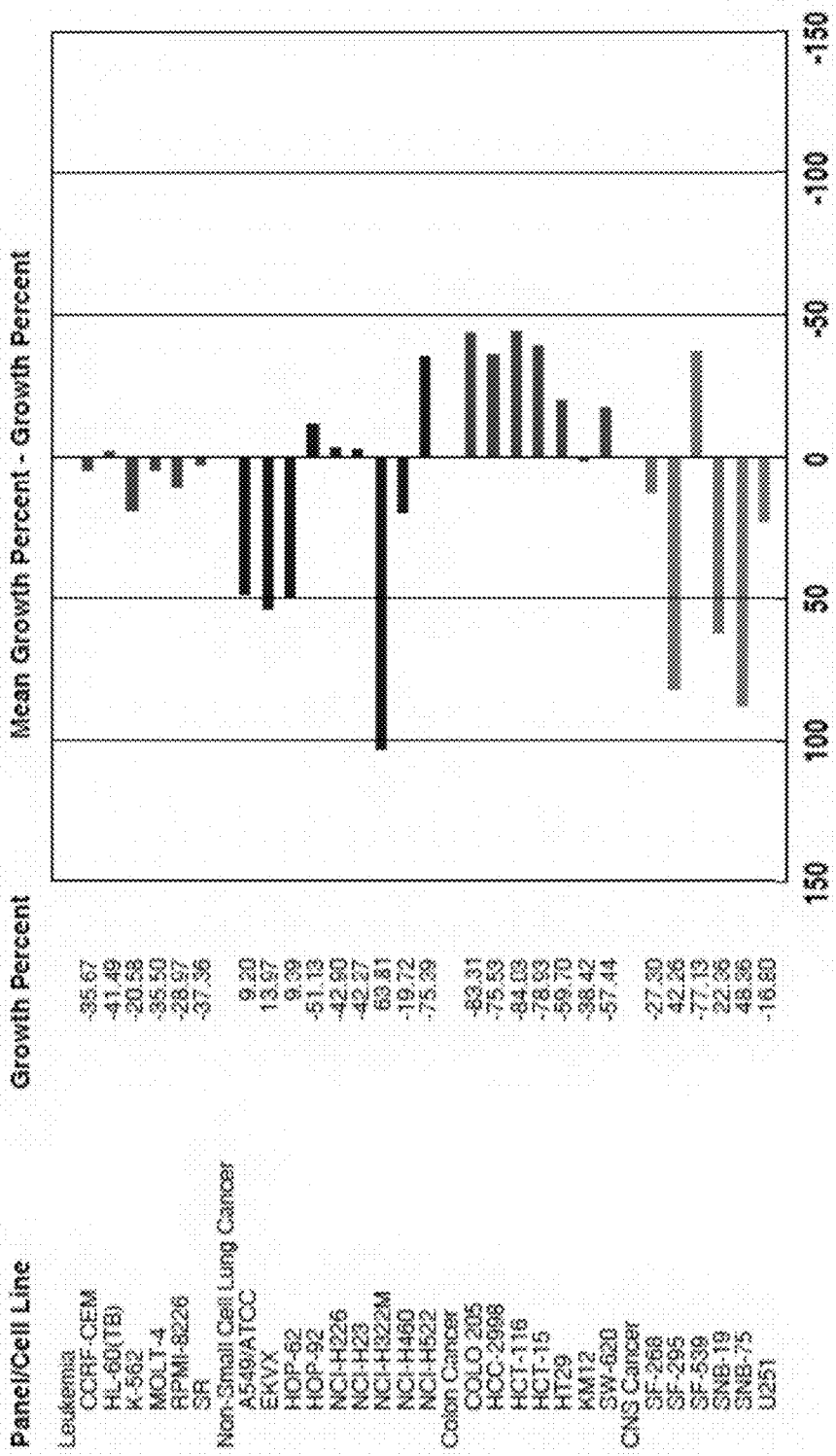
FIG. 20A-B shows NCI single dose results for compound JVM 4-19.
Figure 20B:
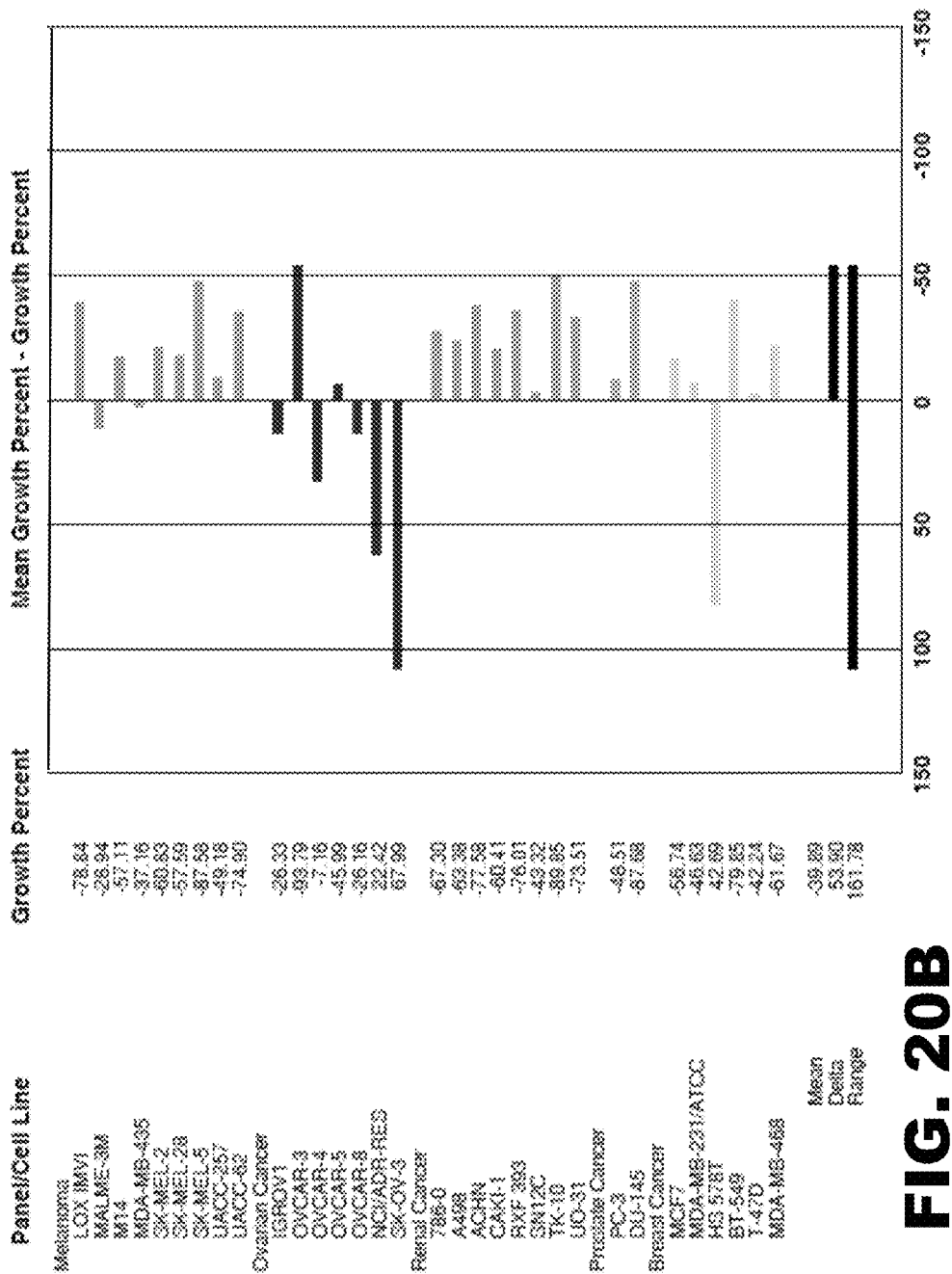

The compounds JVM 4-14 and JVM 4-19 were screened at a single concentration of 10$^{-5}$ M. JVM 4-14 showed potent activity against all leukemia lines tested as well as some NSCLC, colon cancer, melanoma, renal cancer and breast cancer cell lines (FIG. 19A-B). JVM 4-14 also showed moderate activity against CNS cancer and ovarian cancer. Interestingly, JVM 4-19 did not show potent activity against leukemia cell lines, but instead showed potent activity against the majority of colon cancer, melanoma, renal cancer, prostate cancer and breast cancer cell lines tested (FIG. 20A-B). JVM 4-19 also had moderate activity against NSCLC, CNS cancer and ovarian cancer cell lines.

In summary, novel ester and amide conjugates of MMB have been designed and synthesized utilizing a variety of substituted organic carboxylic acids and acid chlorides, a variety of heterocyclic carboxylic acids, and a series of aromatic and aliphatic carboxylic acids in the presence of standard EDCI coupling conditions. The newly synthesized compounds have been evaluated for their anti-leukemic activity against two acute myeloid leukemia cell lines (AML 052308, M9 ENL) and 2 primary AML isolates (AML 100510, and AML 123009). The indole ester conjugate of MMB, BS-2-04, was found to be the most potent compound against AML 052308 cells with an $EC_{50}$ value of 0.72 µM. Other MMB derivatives (BS-1-28, BS-2-01, BS-2-32 and BS-2-05) showed greater cytotoxicity than the parent compound, MMB ($EC_{50}$=16 µM), against the above cultured AML cells.

Figure 18:
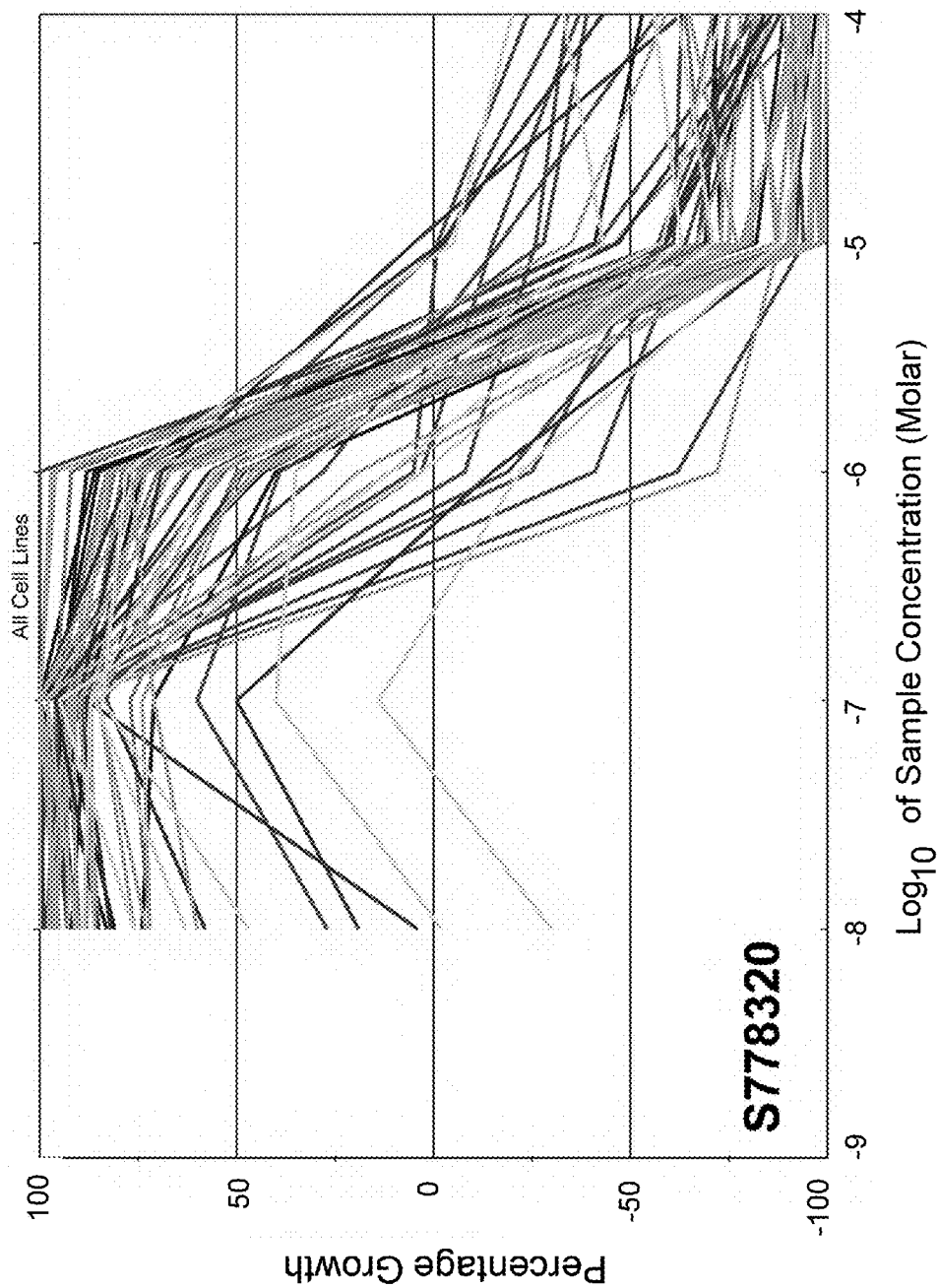
FIG. 18 shows a graph demonstrating the five dose test results of BS-1-28 against 60 human cancer cell lines.

Compound BS-1-28 was also found to be a very potent analogue with $GI_{50}$ values <10 nM against BT-549 and T-467 D breast cancer cell lines, and this compound also exhibited potent growth inhibition ($GI_{50}$=288 nM) against CCRF-CEM leukemia cell lines in the NCI panel of 60 human cancer cell lines (FIG. 18; Table 3).

TABLE 3

NCI five dose result for BS-1-28

| | | Log10 Concentration | | | | | | | | | | | | |
|---|---|---|---|---|---|---|---|---|---|---|---|---|---|---|
| | Time | Mean Opitical Densities | | | | | Percent Growth | | | | | | | |
| Panel/Cell | Zero | Ctrl | -8.0 | -7.0 | -6.0 | -5.0 | -4.0 | -8.0 | -7.0 | -6.0 | -5.0 | -4.0 | GI50 | TGI | LC50 |
| Leukemia | | | | | | | | | | | | | | | |
| CCRF-CEM | 0.467 | 2.683 | 2.658 | 2.460 | 0.533 | 0.395 | 0.224 | 99 | 90 | 3 | -15 | -37 | 2.86E-7 | 1.45E-6 | >1.00E-4 |
| HL-60(TB) | 0.702 | 2.456 | 2.694 | 2.663 | 1.193 | 0.581 | 0.300 | 114 | 112 | 28 | -17 | -57 | 5.46E-7 | 4.15E-6 | 6.58E-5 |
| K-562 | 0.202 | 1.558 | 1.598 | 1.570 | 0.269 | 0.199 | 0.154 | 100 | 98 | 5 | -1 | -24 | 3.27E-7 | 5.79E-6 | >1.00E-4 |
| MOLT-4 | 0.603 | 2.579 | 2.870 | 2.641 | 1.820 | 0.583 | 0.413 | 105 | 103 | 62 | -3 | -32 | 1.51E-6 | 8.89E-6 | >1.00E-4 |
| RPMI-8226 | 0.696 | 2.425 | 2.371 | 2.253 | 0.638 | 0.514 | 0.462 | 97 | 92 | -8 | -26 | -34 | 2.64E-7 | 8.27E-7 | >1.00E-4 |
| SR | 0.509 | 2.005 | 2.032 | 1.975 | 1.297 | 0.368 | 0.309 | 162 | 98 | 53 | -28 | -39 | 1.08E-6 | 4.51E-6 | >1.00E-4 |
| Non-Small Cell Lung Cancer | | | | | | | | | | | | | | | |
| A549/ATCC | 0.518 | 2.528 | 2.351 | 2.454 | 2.362 | 0.305 | 0.246 | 91 | 96 | 92 | -41 | -53 | 2.06E-6 | 4.90E-6 | 5.93E-5 |
| HOP-92 | 1.360 | 1.823 | 1.704 | 1.688 | 1.547 | 0.120 | 0.038 | 74 | 71 | 40 | -91 | -97 | 4.80E-7 | 2.02E-6 | 4.66E-6 |
| NCI-H226 | 1.108 | 2.794 | 2.654 | 2.595 | 2.384 | 0.303 | 0.327 | 92 | 88 | 74 | -73 | -71 | 1.47E-6 | 3.21E-6 | 7.01E-6 |
| NCI-H23 | 0.480 | 1.444 | 1.419 | 1.410 | 1.297 | 0.158 | 0.075 | 96 | 96 | 85 | -67 | -84 | 1.69E-6 | 3.62E-6 | 7.72E-6 |
| NCI-H322M | 0.727 | 1.832 | 1.623 | 1.784 | 1.702 | 0.129 | 0.079 | 81 | 95 | 88 | -82 | -89 | 1.68E-6 | 3.29E-6 | 6.47E-6 |
| NCI-H460 | 0.247 | 2.228 | 2.347 | 2.253 | 1.958 | 0.682 | 0.061 | 166 | 101 | 86 | -67 | -75 | 1.73E-6 | 3.66E-6 | 7.75E-6 |
| NCI-H522 | 0.874 | 1.733 | 1.589 | 1.774 | 1.239 | 0.269 | 0.246 | 83 | 104 | 43 | -69 | -72 | 7.57E-7 | 2.40E-6 | 6.72E-6 |
| Colon Cancer | | | | | | | | | | | | | | | |
| COLO 205 | 0.471 | 1.595 | 0.773 | 1.150 | 0.906 | 0.183 | 0.474 | 27 | 60 | 39 | -61 | -63 | | 2.44E-6 | 7.73E-6 |
| HCC-2998 | 0.724 | 2.399 | 2.446 | 2.473 | 2.467 | 0.295 | 9.114 | 103 | 104 | 104 | -59 | -84 | 2.14E-6 | 4.33E-6 | 8.77E-6 |
| HCT-116 | 0.282 | 1.699 | 1.653 | 1.645 | 0.108 | 0.017 | 0.026 | 97 | 96 | -62 | -94 | -91 | 1.96E-7 | 4.06E-7 | 8.41E-7 |
| HCT-15 | 0.282 | 1.758 | 1.660 | 1.667 | 0.166 | 0.102 | 0.651 | 93 | 94 | -41 | -64 | -82 | 2.11E-7 | 4.95E-7 | 2.43E-6 |
| HT29 | 0.194 | 0.934 | 0.955 | 1.002 | 0.146 | 0.083 | 0.040 | 103 | 109 | -25 | -57 | -80 | 2.76E-7 | 6.51E-7 | 5.97E-4 |
| KM12 | 0.542 | 2.550 | 2.413 | 2.472 | 2.390 | 0.343 | 0.098 | 93 | 96 | 92 | -42 | -82 | 2.05E-6 | 4.84E-6 | 1.56E-5 |
| SW-620 | 0.272 | 1.849 | 1.741 | 1.811 | 0.221 | 0.091 | 0.067 | 93 | 98 | -19 | -67 | -75 | 2.56E-7 | 8.88E-7 | 4.47E-6 |
| CNS Cancer | | | | | | | | | | | | | | | |
| SF-268 | 0.559 | 1.876 | 1.649 | 1.823 | 1.654 | 0.108 | 0.107 | 98 | 96 | 83 | -81 | -85 | 1.59E-6 | 3.22E-6 | 6.50E-8 |
| SF-295 | 0.685 | 2.629 | 2.341 | 2.411 | 2.227 | 0.369 | 0.035 | 85 | 89 | 79 | .46 | -95 | 1.71E-6 | 4.28E-6 | 1.20E-5 |
| SF-539 | 0.726 | 1.866 | 1.752 | 1.788 | 1.520 | 0.062 | 0.089 | 90 | 93 | 70 | -91 | -91 | 1.32E-6 | 2.71E-4 | 6.53E-6 |
| SNB-19 | 0.467 | 1.820 | 1.776 | 1.718 | 4.562 | 0.138 | 0.166 | 57 | 92 | 81 | -70 | -64 | 1.60E-6 | 3.93E-6 | 7.33E-6 |
| SNB-75 | 0.725 | 1.535 | 1.308 | 1.352 | 1.133 | 0.011 | 0.013 | 72 | 77 | 50 | -98 | -58 | 1.01E-6 | 2.19E-6 | 4.72E-6 |
| U251 | 0.544 | 2.552 | 2.519 | 2.469 | 2.391 | 0.222 | 0.157 | 98 | 96 | 92 | -59 | -74 | 1.69E-6 | 4.06E-6 | 8.68E-6 |
| Melanoma | | | | | | | | | | | | | | | |
| LOX IMVI | 0.192 | 1.520 | 1.438 | 1.432 | 0.053 | 0.023 | 0.037 | 93 | 93 | -72 | -88 | -81 | 1.82E-7 | 3.65E-7 | 7.32E-7 |
| MALME-3M | 0.677 | 1.241 | 1.193 | 1.190 | 1.142 | 0.090 | 0.122 | 91 | 91 | 82 | -87 | -82 | 1.56E-6 | 3.07E-6 | 6.07E-6 |
| M14 | 0.494 | 1.525 | 1.398 | 1.393 | 0.972 | 0.097 | 0.041 | 88 | 87 | 46 | -80 | -92 | 8.14E-7 | 2.32E-6 | 5.76E-6 |
| MDA-MB-435 | 0.452 | 2.211 | 2.161 | 2.175 | 1.220 | 0.093 | 0.020 | 97 | 98 | 44 | -76 | -96 | 7.63E-7 | 2.28E-6 | 5.85E-6 |
| SK-MEL-2 | 1.110 | 2.038 | 2.064 | 2.158 | 2.004 | 0.362 | 0.153 | 103 | 113 | 96 | -67 | -88 | 1.92E6 | 3.88E-6 | 7.83E-6 |
| SK-MEL-28 | 0.692 | 1.900 | 1.778 | 1.915 | 4.500 | 0.090 | 0.046 | 90 | 101 | 67 | 47 | -93 | 1.28E-6 | 2.72E-6 | 5.74E-6 |
| SK-MEL-5 | 0.665 | 2.523 | 2.727 | 2.657 | 2.404 | 0.014 | 0.035 | 96 | 92 | 67 | -98 | -95 | 1.26E-6 | 2.54E-6 | 5.12E-6 |
| UACC-257 | 1.139 | 2.637 | 2.606 | 2.535 | 2.377 | 0.290 | 0.246 | 98 | 93 | 53 | -75 | -78 | 1.61E-6 | 3.36E-6 | 6.98E-6 |
| UACC-62 | 0.675 | 2.350 | 2.294 | 2.198 | 1.930 | 0.162 | 0.166 | 97 | 91 | 75 | -73 | -15 | 1.47E-6 | 3.21E-6 | 6.98E-6 |
| Ovarian Cancer | | | | | | | | | | | | | | | |
| OVCAR-3 | 0.484 | 1.460 | 0.670 | 0.973 | 0.413 | 0.039 | 0.023 | 19 | 50 | -15 | -92 | -95 | | 5.92E-7 | 2.66E-6 |
| OVCAR-4 | 0.649 | 1.385 | 0.678 | 1.299 | 1.004 | 0.274 | 0.105 | 4 | 88 | 48 | -58 | -84 | | 2-85E-6 | 8.43E-6 |
| OVCAR-5 | 0.561 | 1.603 | 1.444 | 1.561 | 1.149 | 0.228 | 0.069 | 85 | 96 | 57 | -59 | -88 | 1.14E-6 | 3.07E-6 | 8.22E-6 |
| OVCAR-8 | 0.546 | 2.552 | 1.719 | 2.207 | 1.932 | 0.648 | 0.203 | 58 | 63 | 69 | 5 | -63 | 1.99E-6 | 1.19E-4 | 6.46E-5 |

TABLE 3-continued

NCI five dose result for BS-1-28

| Panel/Cell | Time | | Mean Opitical Densities | | | | | Percent Growth | | | | | GI50 | TGI | LC50 |
|---|---|---|---|---|---|---|---|---|---|---|---|---|---|---|---|
| | Zero | Ctrl | −8.0 | −7.0 | −6.0 | −5.0 | −4.0 | −8.0 | −7.0 | −6.0 | −5.0 | −4.0 | | | |
| NCI/ADR-RES | 0.509 | 1.708 | 1.695 | 1.712 | 4.434 | 0.499 | 0.291 | 99 | 100 | 77 | −2 | −43 | 2.20E−6 | 9.42E−6 | >1.00E−4 |
| SK-OV-3 | 0.932 | 1.391 | 1.309 | 1.347 | 1.288 | 0.491 | 0.134 | 82 | 90 | 77 | −47 | −86 | 1.65E−6 | 4.47E−6 | 1.17E−5 |
| Renal Cancer | | | | | | | | | | | | | | | |
| 786-0 | 0.732 | 2.126 | 2.075 | 2.149 | 0.884 | 0.073 | 0.045 | 96 | 102 | 11 | −90 | −94 | 3.71E−7 | 1.28E−6 | 9.01E−6 |
| A498 | 1.215 | 2.022 | 2.105 | 2.037 | 2.000 | 0.012 | 0.065 | 110 | 102 | 97 | −99 | −95 | 1.74E−6 | 3.43E−6 | 5.63E−6 |
| ACHN | 0.576 | 1.704 | 1.429 | 1.540 | 0.792 | 0.049 | 0.030 | 76 | 55 | 19 | −91 | −95 | 3.42E−7 | 1.49E−6 | 4.22E−6 |
| CAKI-1 | 0.575 | 2.762 | 2.466 | 2.539 | 1.764 | 0.007 | −0.001 | 86 | 90 | 55 | −99 | −100 | 1.08E−6 | 2.18E−6 | 4.82E−6 |
| RXF 393 | 0.893 | 1.288 | 1.129 | 1.201 | 1.012 | 0.161 | 0.245 | 73 | 85 | 54 | −77 | −65 | 1.07E−6 | 2.58E−6 | 6.23E−6 |
| SN12C | 0.727 | 2.414 | 1.743 | 1.918 | 2.025 | 0.469 | 0.296 | 60 | 71 | 77 | −35 | −59 | 1.14E−6 | 4.83E−6 | 9.05E−5 |
| TK-10 | 0.969 | 1.838 | 1.798 | 1.983 | 1.613 | 0.044 | 0.024 | 95 | 117 | 74 | −96 | −98 | 1.39E−6 | 2.73E−6 | 5.39E−6 |
| UO-31 | 0.802 | 2.408 | 1.965 | 1.990 | 1.584 | 0.061 | 0.092 | 72 | 74 | 49 | −92 | −89 | 8.87E−4 | 2.21E−6 | 5.00E−6 |
| Prostate Cancer | | | | | | | | | | | | | | | |
| PC-3 | 0.614 | 2.481 | 2.212 | 2.234 | 1.075 | 0.130 | 0.039 | 88 | 87 | 73 | −79 | −94 | 1.42E−6 | 3.62E−4 | 6.45E−6 |
| DU-145 | 0.370 | 1.647 | 1.530 | 1.618 | 1.179 | 0.019 | 0.009 | 91 | 98 | 63 | −95 | −98 | 1.21E−6 | 2.51E−6 | 5.20E−6 |
| Breast Cancer | | | | | | | | | | | | | | | |
| MCF7 | 0.348 | 1.951 | 1.365 | 1.732 | 0.517 | 0.130 | 0.154 | 63 | 88 | 11 | −63 | −56 | 3.02E−7 | 1.39E−6 | 6.69E−6 |
| MDA-MB-231/ATCC | 0.538 | 1.667 | 1.546 | 1.515 | 1.174 | 0.228 | 0.193 | 89 | 87 | 56 | −58 | −73 | 1.14E−6 | 3.12E−6 | 8.56E−6 |
| HS 57BT | 1.120 | 2.299 | 1.676 | 2.106 | 2.035 | 1.065 | 0.901 | 47 | 84 | 78 | −5 | −20 | | 8.71E−6 | >1.00E−4 |
| BT-549 | 1.331 | 1.928 | 0.926 | 1.417 | 1.034 | 0.159 | 0.019 | −30 | 14 | −22 | −88 | −99 | <1.00E−8 | | 2.64E−6 |
| T-47D | 0.637 | 1.368 | 0.523 | 0.930 | 0.897 | 0.362 | 0.428 | −2 | 40 | 35 | −43 | −33 | <1.00E−8 | | >1.00E−4 |
| MDA-MB-468 | 0.761 | 1.596 | 1.396 | 1.550 | 0.787 | 0.219 | 0.286 | 76 | 95 | 3 | −71 | −52 | 3.07E−7 | 1.10E−6 | 5.17E−6 |

Example 22

(1aR,7aS,10aS,10bS,E)-1a-methyl-8-methylene-N-(5-(methylthio)-1H-1,2,4-triazol-3-yl)-9-oxo-1a,2,3,6,7,7a,8,9,10a,10b-decahydrooxireno[2',3':9,10]cyclodeca[1,2-b]furan-5-carboxamide (JVM 3-53)

To melampomagnolic acid (30 mg, 0.107 mmol in dichloromethane, was added EDC (30 mg, 0.161 mmol), HOBt (21.7 mg, 0.161 mmol), triethylamine (32.6 mg, 0.323 mmol) and 5-(methylthio)-1H-1,2,4-triazol-3-amine (13.9 mg, 0.107 mmol) at ambient temperature. The reaction mixture was stirred for 3 h at ambient temperature. When the reaction was complete (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-53 as a white solid (yield: 51%).

NMR ($CDCl_3$, 400 MHz): δ 6.58 (t, J=8 Hz, 1H), 6.34 (s, 2H), 6.20 (d, J=3.2 Hz, 1H), 5.44 (d, J=3.2 Hz, 1H), 3.83 (t, J=9.6 Hz, 1H), 3.28 (d, J=9.2 Hz, 1H), 3.01 (dd, J=15.2, 6.4 Hz, 1H), 2.91-2.85 (m, 1H), 2.54-2.26 (m, 8H), 1.70-1.63 (m, 1H), 1.58 (s, 3H), 1.29-1.2 (m, 1H). $^{13}C$ NMR ($CDCl_3$, 100 MHz): δ 169.3, 168.6, 163.4, 158.0, 141.8, 138.9, 134.9, 120.4, 81.2, 62.4, 59.6, 42.5, 36.1, 25.6, 24.6, 24.4, 18.1, 13.9 ppm.

Example 23

((1aR,7aS,10aS,10bS,E)-1a-methyl-8-methylene-9-oxo-1a,2,3,6,7,7a,8,9,10a,10b-decahydrooxireno[2',3':9,10]cycodeca[1,2-b]furan-5-yl)methyl 2-naphthoate (JVM 3-36)

To MMB (50 mg, 0.189 mmol) in dichloromethane (2 mL), was added 2-naphthoyl chloride (35.9 mg, 0.189 mmol) and triethylamine (28.6 mg, 0.283 mmol) at 0° C. The reaction mixture was stirred for 8 h at ambient temperature. When the reaction was complete (monitored by TLC), water was added and the resulting aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-36 as white solid (yield: 68%).

$^1H$ NMR ($CDCl_3$, 400 MHz): δ 8.58 (s, 1H), 8.04 (d, J=7.6 Hz, 1H), 7.96 (d, J=8.0 Hz, 1H), 7.90 (d, J=8.4 Hz, 2H), 7.63-7.54 (m, 2H), 6.23 (s, 1H), 5.83 (t, J=8.4 Hz, 1H), 5.54 (s, 1H), 5.0 (d, J=12.8 Hz, 1H), 4.79 (d, J=12.4 Hz, 1H), 3.89 (t, J=9.2 Hz, 1H), 3.05-2.99 (m, 1H), 2.94 (d, J=9.6 Hz, 1H), 2.55-2.17 (m, 7H), 1.73 (t, J=7.2 Hz, 111), 1.57 (s, 3H), 1.15 (t, I=13.2 Hz, 1H).

References for Example 21-23

1. Guzman M L, Rossi R M, Karnischky L, Li X, Peterson D R, Howard D S et al. The sesquiterpene lactone parthenolide induces apoptosis of human acute myelogenous leukemia stem and progenitor cells. Blood 2005; 105: 4163-4169.
2. Heptinstall, S.; Groenewegen, W. A.; Spangenberg, P.; Losche, W. Folia Haematol. Int. Mag. KIM. Morphol. Blutforsch. 1988, 115, 447.

3. Hall, 1. H.; Lee, K. H.; Starnes, C. O.; Sumida, Y.; Wu, R. Y.; Waddell, T. G.; Cochran, J. W.; Gerhart, K. G. J. Pharm. Sci. 1979, 68, 537.
4. Pfaffenrath, V.; Diener, H. C.; Fischer, M.; Henneicke-Von, Z. H. H. Cephalalgia 2002, 22, 523.
5. Bork, P. M.; Schmitz, M. L.; Kulmt, M.; Escher, C.; Heinrich, M. FEES Lett. 1997, 402, 85.
6. (a) Gopal, Y. V.; Arora, T. S.; Van Dyke, M. W. Chem. Biol. 2007, 14, 813-823. (b) Kim, Y. J.; Choi, M. H.; Hong, S. T.; Bae, Y. M. Parasitol. Res. 2009, 104, 1011-1016. (c) Riganti, C.; Doublier, S.; Viarisio, D.; Miraglia, E.; Pescarmona, G.; Ghigo, D.; Bosia, A. Br. J. Pharmacol. 2009, 156, 1054-1066. (d) Dell'Agli, M.; Galli, G. V.; Bosisio, E.; Dambrosi, M. Bioorg. Med. Chem. Lett. 2009, 19, 1858-1860.
7. Guzman, M. L., Karnischky, L., Li, X. J., Neering, S. J., Rossi, R. M., and Jordan, C. T.; Selective induction of apoptosis in acute myelogenous leukemia stem cells by the novel agent parthenolide. Blood 104, 2004, 697a-697a.
8. Guzman, M. L., Rossi, R. M., Li, X. J., Corbett, C., Hassane, D. C., Bushnell, T., Carroll, M., Sullivan, E., Neelakantan, S., Crooks, P. A., and Jordan, C. T.; A novel orally available parthenolide analog selectively eradicates AML stem and progenitor cells. Blood 108, 2006, 74a-74a.
9. Hassane, D. C.; Sen, S.; Minhajuddin, M.; Rossi, R. M.; Corbett, C. A.; Balys, M.; Wei, L.; Crooks, P. A.; Guzman, M. L.; Jordan, C. T. Chemical Genomic Screening Reveals Synergism between Parthenolide and Inhibitors of the PI-3 Kinase and mTOR Pathways. Blood 2010, 116, 5983-5990.
10. Guzman, M. L.; Rossi, R. M.; Neelakantan, S.; Li, X.; Corbett, C. A.; Hassane, D. C.; Becker, M. W.; Bennett, J. M.; Sullivan, E.; Lachowicz, J. L.; Vaughan, A.; Sweeney, C. J.; Matthews, W.; Carroll, M.; Liesveld, J. L.; Crooks, P. A.; Jordan, C. T. An Orally Bioavailable Parthenolide Analog Selectively Eradicates Acute Myelogenous Leukemia Stem and Progenitor Cells. Blood 2007, 110, 4427-4435.
11. Ghantous, A.; Gali-Muhtasib, H.; Vuorela, H.; Saliba, N. A.; Darwiche, N. What Made Sesquiterpene Lactones Reach Cancer Clinical Trials? Drug Discovery Today 2010, 15, 668-678.
12. Ralstin, M. C.; Gage, E. A.; Yip-Schneider, M. T.; Klein, P. J.; Wiebke, E. A.; Schmidt, C. M. Mol. Cancer Res. 2006, 4, 387.
13. Won, Y. K.; Ong, C. N.; Shen, H. M. Carcinogenesis 2005, 26, 2149.
14. Oka, D.; Nishimura, K.; Shiba, M.; Nakai, Y.; Arai, Y.; Nakayama, M.; Takayama, H.; Inoue, H.; Okuyama, A.; Nonomura, N. Int. J. Cancer 2007, 120, 2576.
15. Joshua N. K., Kristen M. O., Craig T. J., and Rudi F.; Discovery of Potent Parthenolide-Based Antileukemic Agents Enabled by Late-Stage P450-Mediated C-H Functionalization; ACS Chem. Biol. 2014, 9, 164-173.
16. N. R. Penthala, S. Bommagani, V. Janganati, K. B. MacNicol, C. E. Cragle, N. R. Madadi, L. L. Hardy, A. M. MacNicol and P. A. Crooks, European Journal of Medicinal Chemisity, 2014, 85, 517-525.
17. El-Feraly, F. S. Phytochemistry 1984, 23, 2372.
18. Shama N., ShanShan P., Fred K. H., Craig T. J., Peter A C.; Melampomagnolide B: A new antileukemic sesquiterpene; Bioorg. Aled. Chem. 19, 2011, 1515-1519.

What is claimed is:

1. A compound comprising Formula (I):

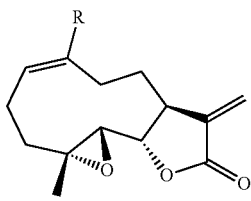

wherein:
R is selected from the group consisting of

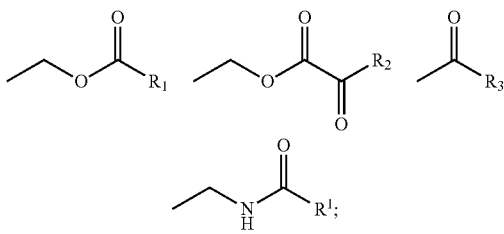

wherein:
$R_1$ is selected from the group consisting of substituted indoles, substituted heterocyclic aromatic, and substituted aromatic derivatives;
$R_2$ is selected from the group consisting of substituted indoles; and
$R_3$ is selected from the group consisting of substituted amines.

2. The compound of claim 1, wherein Formula (I) comprises:

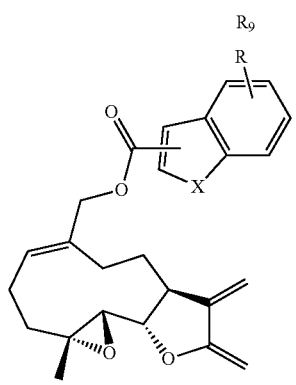

wherein:
X is selected from the group consisting of S, O, NH, $NR_{10}$;
$R_9$ is selected from the group consisting of OMe, Cl, Br and F; and
$R_{10}$ is selected from the group consisting of H, $CH_3$, benzyl, substituted benzyl, benzoyl, substituted benzoyl, and benzylsulfonyl and substituted benzylsulfonyl.

3. The compound of claim 1, wherein Formula (I) comprises:

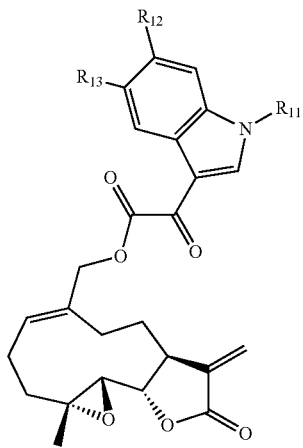

(V)

wherein:
$R_{11}$ is selected from the group consisting of H, $CH_3$, benzyl, substituted benzyl, benzoyl, substituted benzoyl, and benzylsulfonyl and substituted benzylsulfonyl; and
$R_{12}$ and $R_{13}$ are independently selected from the group consisting of H, F, Cl, Br, $OCH_3$, CN, $CH_3$, $NO_2$ and $COOCH_3$.

4. The compound of claim 1, wherein Formula (I) comprises:

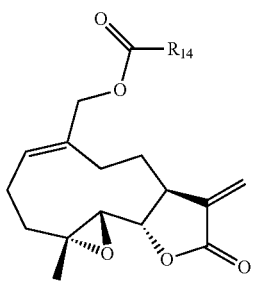

(VI)

wherein:
$R_{14}$ is selected from the group consisting of 2-thiophenyl, 3-thiophenyl, 2-pyrazine, 3-pyrazine, 2-amino nicotinic acid, indole-3-acetic acid, indole-3-acrylic acid.

5. The compound of claim 1, wherein Formula (I) comprises:

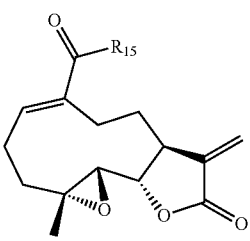

(VII)

wherein:
$R_{15}$ is selected from the group consisting of:

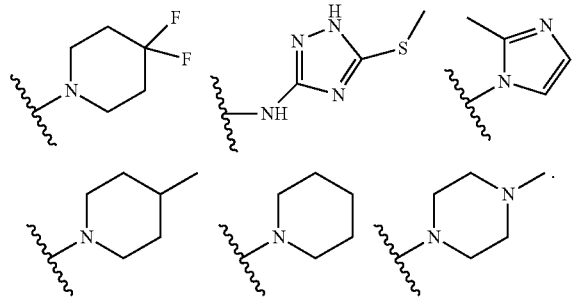

6. The compound of claim 1, wherein Formula (I) comprises:

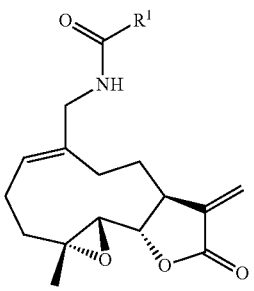

(VIII)

wherein:
$R_1$ is selected from the group consisting of substituted indoles, substituted heterocyclic aromatic, aromatic and aliphatic derivatives.

7. A pharmaceutically acceptable salt comprising a compound of claim 1.

* * * * *